United States Patent
Jacobson et al.

(10) Patent No.: US 8,518,957 B2
(45) Date of Patent: Aug. 27, 2013

(54) METHANOCARBA ADENOSINE DERIVATIVES, PHARMACEUTICAL COMPOSITIONS, AND METHOD OF REDUCING INTRAOCULAR PRESSURE

(75) Inventors: Kenneth A. Jacobson, Silver Spring, MD (US); Dilip K. Tosh, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/512,681

(22) PCT Filed: Dec. 2, 2010

(86) PCT No.: PCT/US2010/058746
§ 371 (c)(1),
(2), (4) Date: Jun. 21, 2012

(87) PCT Pub. No.: WO2011/068978
PCT Pub. Date: Jun. 9, 2011

(65) Prior Publication Data
US 2012/0264769 A1    Oct. 18, 2012

Related U.S. Application Data

(60) Provisional application No. 61/266,084, filed on Dec. 2, 2009, provisional application No. 61/313,961, filed on Mar. 15, 2010.

(51) Int. Cl.
*A61K 31/52* (2006.01)
*C07D 473/00* (2006.01)

(52) U.S. Cl.
USPC ........................................ 514/263.2; 544/277

(58) Field of Classification Search
USPC ....................................................... 544/277
See application file for complete search history.

(56) References Cited

U.S. PATENT DOCUMENTS

| | | |
|---|---|---|
| 2,577,706 A | 12/1951 | Hotten |
| 3,146,211 A | 8/1964 | Errede |
| 3,984,406 A | 10/1976 | Quadbeck-Seeger et al. |
| 4,048,171 A | 9/1977 | Bossert et al. |
| 4,072,633 A | 2/1978 | Hermans |
| 4,548,818 A | 10/1985 | Kjellin et al. |
| 4,659,717 A | 4/1987 | Wikel |
| 4,672,068 A | 6/1987 | Kutsuma et al. |
| 4,772,607 A | 9/1988 | Badger et al. |
| 4,866,072 A | 9/1989 | Edwards et al. |
| 4,954,504 A | 9/1990 | Chen et al. |
| 4,966,848 A * | 10/1990 | Smith et al. ............. 435/193 |
| 5,032,593 A | 7/1991 | Rzeszotarski et al. |
| 5,063,233 A | 11/1991 | Chen et al. |
| 5,096,916 A | 3/1992 | Skupin |
| 5,140,015 A | 8/1992 | Olsson et al. |
| 5,270,316 A | 12/1993 | Suzuki et al. |
| 5,280,015 A | 1/1994 | Jacobson et al. |
| 5,284,834 A | 2/1994 | Jacobson et al. |
| 5,310,731 A | 5/1994 | Olsson et al. |
| 5,366,977 A | 11/1994 | Pollard et al. |
| 5,443,836 A | 8/1995 | Downey et al. |
| 5,498,605 A | 3/1996 | Jacobson et al. |
| 5,620,676 A | 4/1997 | Jacobson et al. |
| 5,629,454 A | 5/1997 | Marquez et al. |
| 5,688,774 A | 11/1997 | Jacobson et al. |
| 5,773,423 A | 6/1998 | Jacobson et al. |

(Continued)

FOREIGN PATENT DOCUMENTS

| | | |
|---|---|---|
| DE | 4325254 A1 | 2/1994 |
| EP | 0374808 A2 | 6/1990 |

(Continued)

OTHER PUBLICATIONS

Tosh et. al. J. Med. Chem. (2009) 52, 7580-7592.*

(Continued)

*Primary Examiner* — Noble Jarrell
*Assistant Examiner* — Laura Daniel
(74) *Attorney, Agent, or Firm* — Leydig, Voit & Mayer, Ltd.

(57) ABSTRACT

Disclosed are (N)-methanocarba adenine nucleosides, e.g., of the formula (I): as $A_3$ adenosine receptor agonists, pharmaceutical compositions comprising such nucleosides, and a method of use of these nucleosides, wherein A, a, $R^2$, and $R^3$ are as defined in the specification. These nucleosides are contemplated for use in the treatment a number of diseases, for example, inflammation, cardiac ischemia, stroke, asthma, diabetes, and cardiac arrhythmias. Also disclosed are conjugates comprising a dendrimer and one or more ligands, which are functionalized congeners of an agonist or antagonist of a receptor of the G-protein coupled receptor (GPCR) superfamily. Such conjugates are have the potential of being used as dual agonists, dual antagonists, or agonist/antagonist combinations.

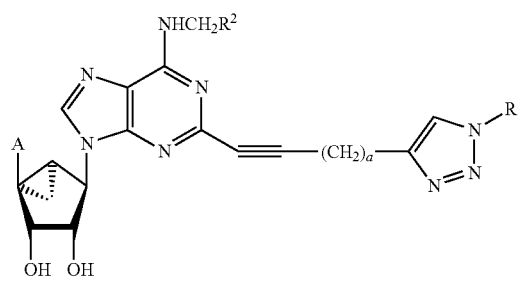

(I)

19 Claims, 29 Drawing Sheets

(56) References Cited

U.S. PATENT DOCUMENTS

| | | | |
|---|---|---|---|
| 5,840,728 A | 11/1998 | Marquez et al. |
| 5,877,179 A | 3/1999 | Pollard et al. |
| 6,066,642 A | 5/2000 | Jacobson et al. |
| 6,211,165 B1 | 4/2001 | Liang et al. |
| 6,316,423 B1 | 11/2001 | Von Lubitz et al. |
| 6,376,521 B1 | 4/2002 | Jacobson et al. |
| 6,586,413 B2 | 7/2003 | Liang et al. |
| 7,009,050 B2 | 3/2006 | Marquez et al. |
| 7,087,589 B2 | 8/2006 | Jacobson et al. |
| 7,199,127 B2 | 4/2007 | Jeong et al. |
| 7,790,735 B2 | 9/2010 | Jacobson et al. |
| 8,153,781 B2 | 4/2012 | Jacobson et al. |
| 2003/0216412 A1 | 11/2003 | Jacobson et al. |
| 2004/0142946 A1 | 7/2004 | Chattopadhyaya |
| 2007/0232626 A1 | 10/2007 | Jacobson et al. |
| 2007/0265223 A1 | 11/2007 | Tomaselli et al. |

FOREIGN PATENT DOCUMENTS

| | | |
|---|---|---|
| EP | 0577558 A2 | 1/1994 |
| EP | 0 217 530 | 4/1997 |
| WO | 94/03456 A1 | 2/1994 |
| WO | 94/25605 A1 | 11/1994 |
| WO | 94/25607 A1 | 11/1994 |
| WO | 95/03304 A1 | 2/1995 |
| WO | 95/08541 A1 | 3/1995 |
| WO | 96/02553 A2 | 2/1996 |
| WO | 96/16084 A2 | 5/1996 |
| WO | 97/27177 A2 | 7/1997 |
| WO | 98/05662 A1 | 2/1998 |
| WO | 01/51490 A1 | 7/2001 |
| WO | 2006/031505 A1 | 3/2006 |
| WO | 2006/113204 A2 | 10/2006 |
| WO | 2006/128159 A2 | 11/2006 |
| WO | 2008/006369 A1 | 1/2008 |
| WO | 2009/123881 A1 | 10/2009 |

OTHER PUBLICATIONS

Melman et al. Bioorganic & Medicinal Chemistry Letters 18 (2008) 2813-2819.*

Bock et al. Org. Biomol. Chem. (2007) 5, 971-975.*

Abbracchio et al., "International Union of Pharmacology LVIII: Update on the P2Y G Protein-Coupled Nucleotide Receptors: From Molecular Mechanisms and Pathophysiology to Therapy," *Pharmacol. Rev.*, 58 (8), 281-341 (2006).

Abdelmoez et al., "Synthesis of New Polymer-Bound Adenine Nucleotides Using Starburst PAMAM Dendrimers," *Biotechnology Progress*, 18 (4), 706-712 (Jul. 2002).

Ali et al., "Sustained activation of phospholipase D via adenosine $A_3$ receptors is associated with enhancement of antigen- and Ca(2+)-ionophore-induced secretion in a rat mast cell line," *JPET-Abstracts*, 276 (2), 837-845 (1996).

Altmann et al., "4'6'-Methano Carbocyclic Thymidine: A Conformationally, Constrained Building Block for Oligonucleotides." *Tetrahedron Letters*, 35 (15), 2331-2334 (1994).

Altmann et al., "1',6'-Methano Carbocyclic Thymidine: Synthesis, X-ray Crystal Structure and Effect on Nucleic Acid Duplex Stability," *Tetrahedron Letters*, 35 (41), 7625-7628 (1994).

Alzheimer et al., "Transient and selective blockade of adenosine $A_1$-receptors by 8-cyclopentyl-1,3-dipropylaxanthine (DPCPX) causes sustained epileptiform activity in hippocampal CA3 neurons of guinea pigs," *Neuroscience Letters*, 99 (1,2), 107-112 (1989).

Baraldi et al., "Pyrazolo-triazolo-pyrimidine derivatives as adenosine receptor antagonists: a possible template for adenosine receptor subtypes?", *Current Pharamaceutical Design*, 8 (26), 2299-2332 (2002).

Beach et al., "Effects of adenosine on ion transport in rat medullary thick ascending limb," *Am. J. Physiol.*, 263 (3), 3pages, including abstract (1992).

Bowler et al., "Ribose-Modified N-Methoxyadenosine Analogues Controlling Cytokines," *Drug Devel. Res.*, 43, 26 (1998).

Brackett et al., "Activities of Caffeine, Theophylline, and Enprofylline Analogs as Tracheal Relaxants," *Biochemical Pharmacology*, 39 (12), 1897-1904 (1990).

Bruns et al., Adenosine receptors in brain membranes: Binding of $N^6$-cyclohexyl[$^3$H]adenosine and 1,3-diethyl-8-[$^3$H]phenylxanthine, *Proc. Natl. Acad. Sci.*, 77 (9), 5547-5551 (1980).

Bruns et al., "Characterization of the $A_2$ Adenosine Receptor Labeled by $^3$H]NECA in Rat Striatal Membranes," *Molecular Pharmacology*, 2, 331-346 (1986).

Bruns et al., "Role of Adenosine in Energy Supply/Demand Balance," *Nucleosides & Nucleotides*, 10 (5), 931-943 (1991).

Carruthers et al., "Adenosine $A_3$ receptors: two into one won't go," *Reprinted from Trends in Pharmacological Sciences*, 14 (8), 290-291 (1993).

Chao et al., "Synthesis of Bicarbocyclic Dideoxynucleosides as Potential Antiviral Agents," *Tetrahedron*, 53 (6), 1957-1970 (1997).

Daly, "Mechanism of Action of Caffenine," *Caffeine, Coffee, and Health*, edited by S. Garatini, Published by Raven Press, Ltd., New York, 97-150 (1993).

Damasio et al., "Alzheimer's Disease and related dementias," *Cecil Textbook of Medicine, 20$^{th}$ Edition*, 2, 1992-1996 (1996).

De et al., "Differential Distribution of $A_3$ Receptor in Rat Brain," *Society for Neuroscience Abstracts*, 19 (1993).

Dyatkina et al., "Modified Triphosphates of Carbocyclic Nucleoside Analogues: Synthesis, Stability towards Alkaline Phosphatase and Substrate Properties for Some DNA Plymerases," *Bioorganic & Medicinal Letters*, 6 (22), 2639-2642 (1996).

Eidelman et al., "$A_1$ adenosine-receptor antagonists activate chloride efflux from cystic fibrosis cells," *Proc. Natl. Acad. Sci.*, 89, 5562-5566, (1992).

Ezzitouni et al., "A Simple Approach to 1',1'a-Methano Carbocyclic Thymidine," *J. Chem. Soc., Chem. Commun.*, 1345-1346 (1995).

Ezzitouni et al., "Conformationally locked carbocyclic nucleosides built on a bicyolo[3.1.0]hexane template with a fixed Southern conformation. Synthesis and antiviral activity," *J. Chem. Soc., Perkin Trans.*, 1, 1073-1078 (1997).

Ezzitouni et al., "(1s,2R)-[(Benzyloxy)methyl]cyclopent-3-enol. A Versatile Synthon for the Preparation of 4',1'a-Methano- and 1',1'a-Methanocarbocylclic Nucleosides," *J. Org. Chem.*, 62, 4870-4873 (1997).

Feoktistov et al., "Adenosine A2B receptors," *Pharmacological Reviews*, 49 (4), 381-402 (1997).

Fischer et al., "Adenosine 5'-Phosphorothioate -2-Thioether and 5'Boranophosphate -2-Thioeter Derivatives as Potential Antidiabetic Drugs," *Drug Devel. Res.*, 43, 28 (1998).

Fozard et al., "Adenosine $A_3$ receptors mediate hypotension in the angiotensin II-supported circulation and the pithed rat," *Br. J. Pharmacol.*, 109, 3-5 (1993).

Gong, "A Convenient Synthesis of 5-(O,O-Dialkylphosphoryl)-4-aryl-3,4-dihydropyrimidin-2(1$H$)-ones," *Heteroatom Chemistry*, 14 (1), 13-17 (2003).

Hackh'S Chemical Dictionary, "phosphate," 5$^{th}$ edition, 444 (1987).

Hechler et al., ÁTP Derivatives Are Antagonists of the $P2Y_1$ Receptor: Similarities to the Platelet ADP Receptor, *Molecular Pharmacology*, 53, 727-733 (1998).

Jacobson et al., "Molecular Recognition at Adenine Nucleotide (P2) Receptors in Platelets," *Seminars in Thrombosis and Hemostasis*, 31 (2), 205-216 (2005).

Jacobson et al., "Functionalized Congeners of Adenosine: Preparation of Analogues with High Affinity for $A_1$-Adenosine Receptors," *J. Med. Chem.*, 28, 1341-1346 (1985).

Jacobson et al., "A Functionalized Congener Approach to Adenosine Receptor Antagonists: Amino Acid Conjugates of 1,3-Dipropylxanthine," *Mol. Pharmacol.*, 29, 126-133 (1986).

Jacobson et al., "A Novel Pharmacological Approach to Treating Cardiac Ischemia," *J. Biol. Chem.*, 275 (39), 30272-30279 (2000).

Jacobson et al., "Functionalized congeners of 1,3-dialkylxanthines: Preparation of Analogues with High Affinity for Adenosine Receptors," *J. Med. Chem.*, 28,1334-1340 (1985).

Jacobson et al., "$N^6$-Functionalized Congeners of Adenosine with High Potency at $A_2$-Adenosine Receptors: Potential Ligands for Affinity Chromatography," *Biochem. Biophys. Res. Commun.*, 136 (3), 1097-1102 (1986).

Jacobson et al., "Xanthine Functionalized Congeners as Potent Ligands at $A_2$-Adenosine Receptors," *J. Med. Chem.*, 30, 211-214 (1987).

Jacobson et al., "Purine Functionalized Congeners as Molecular Probes for Adenosine Receptors," *Nucleos. Nucleotid.*, 10 (5), 1029-1038 (1991).

Jacobson et al., "Adenosine receptors as therapeutic targets," Nature Reviews Drug Discovery, 5 (3), 247-264 (2006).

Jacobson et al., "Novel Selective Non-Xanthine $A_3$ Adenosine Receptor Antagonists", *Abstract from Purines*, (1996).

Jacobson et al., "Stimulation by Alkylxanthines of Chloride Efflux in DFPAC-1 Cells does not Involve $A_1$ Adenosine Receptors," *Biochemistry*, 34, 9088-9094 (1995).

Jacobson et al., "8-(3-Chlorostyryl)caffeine (CSC) is a selective $A_2$-adenosine antagonists in vitro and in vivo," *FEBS Letters*, 323 (1,2), 141-144 (1993).

Jacobson et al., "Synthesis and Biological Activity of $N^6$-(p-Sulfophenyl)alkyl and $N^6$-Sulfoalkyl Derivatives of Adenosine: Water-soluble and Peripherally Selective Adenosine Agonists," *J. Med. Chem.*, 35 (22), 4143-4149 (1992).

Jacobson et al., "Adenosine Receptors: Pharmacology, Structure-Activity Relationships, and Therapeutic Potential," *J. Med. Chem.*, 35 (3), 407-422 (1992).

Jacobson et al., "Development of Selective Purinoceptor Agonists and Antagonists," *Purinergic Approaches in Experimental Therapeutics*, Chapter 6, 101-128 (1997).

Jacobson et al., "Structure Activity Relationships of P2 Receptor Agonists and Antagonists," *The P2 Nucleotide Receptors, Eds.*, Chap. 4, 81-107 (1998).

Jacobson, "Adenosine ($P_1$) and ATP ($P_2$) Receptors," Ed., Pergamon Press: Oxford, UK, 3 (10 12), 601-642 (1990).

Jeong et al., "Synthesis and Anti-HIV Activity of Carboxyclic Ring-enlarged 4',1'a-Methano Oxetanocin Analogues," *Nucleosides & Nucleotides*, 16 (7-9), 1059-1062 (1997).

Jeong et al., "Use of Cyclic Sulfite as an Epoxide Surrogate in the Regioselective Synthesis of a Carbocyclic Ring-Englarged 4',1'a-Methano Oxetanocin Analogue," *Tetrahedron Letters*, 37 (14), 2353-2356 (1996).

Jevprasesphant et al., "The influence of surface modification on the cytotoxicity of PAMAM dendrimers," *Int'l J. Pharma.*, 252 (1-2), 263-266 (2003).

Ji et al., "Flavonoid Derivatives as $A_3$ Adenosine Receptor Antagonists", *Abstract from Purines*, (1996).

Ji et al., "A selective agonists affinity label for $A_3$ adenosine receptors," *Biochem. Biophys. Res. Comm.*, 203 (1), 570-576 (1994).

Ji et al., "Species Differences in Ligand Affinity at Central $A_3$-Adenosine Receptors," *Drug Development Research*, 33:00-00, 11 pages (1994).

Jiang et al., "6-Phenyl-1,4-dihydropyridine Derivatives as Potent and Selective $A_3$ Adenosine Receptor Antagonists," *J. Med. Chem.*, 39, 4667-4675 (1996).

Jiang et al., "Structre-Activity Relationships of 4-(Phenylethyny1-6-pheny1-1,4-dihydropyridines as Highly Selective $A_3$ Adenosine Receptor Antagonists," *Med. Chem.*, 40, 2596-2608 (1997).

Karton et al., "Synthesis and Biological Activities of Flavonoid Derivatives as $A_3$ Adenosine Receptor Antagonists," *J. Med. Chem.*, 39, 2293-2301 (1996).

Katagiri et al., "The first synthesis of 2'3'-methanocarbocyclic nucleoside," *Tetrathedron Letters*, 40, 9069-9072 (1999).

Kim et al., "Toward Multivalent Signaling across G Protein-Coupled Receptors from Poly(amidoamine) Dendrimers," *Bioconjugate Chemistry*, 19 (2), 406-411 (2008).

Kim et al., "Derivatives of the Triazoloquinazoline Adenosine Antagonists (CGS15943) Are Selective for the Human $A_3$ Receptor Subtype," *J. Med. Chem.*, 39, 4141-4148 (1996).

Kim et al., "Methanocarba modification of uracil and adenine nucleotides: high potency of Northern ring conformation at P2Y1, P2Y2, P2Y4, and P2Y11 but not P2Y6 receptors," *Journal of Medicinal Chemistry*, 45 (1), 208-218 (2002).

Knoblauch et al., "UTP Derivatives and Analogs as P2Y2 (P2u) Receptor Agonists," *Drug Devel. Res.*, 43, 34 (1998).

Knutsen et al., "New Adenosine $A_1$ and $A_3$ Selective N-Alkoxypurines," *Drug Devel. Res.*, 43, 25 (1998).

Kononova, "Phosphonates and Their Degradation by Microorganisms," *Biochemistry* (Moscow), 67 (2), 184-195 (2002).

Layzer, "Degenerative Diseases of the Nervous System," *Cecil Textbook of Medicine, 20th Edition*, 2, 2050-2057 (1996).

Li et al., "Structure-Activity Relationships and Molecular Modeling of 3,5-Diacy1-2,4-dialkylpyridine Derivatives as Selective $A_3$ Adenosine Receptor Antagonists," *J. Med. Chem.*, 41, 3186-3201 (1998).

Lopin, "Phosphonyl, phosphonothioyl, phosphaonodithioyl, and phosphonotrithioyl radicals: generation and study of their addition onto alkenes," *J. Org. Chem.*, 68 (26), 9916-9923 (2003).

Marquez et al., "Synthesis of Conformationally Restricted Carbocyclic Nucleosides: The Role of the O(4')-Atom in the Key Hydration Step of Adenosine Deaminase," *Helvetica Chimica Acta*, 82, 2119-2139 (1999).

Marquez et al., "HIV-1 Reverse Transcriptase Can Discriminate between two Conformationally Locked Carbocylic AZT Triphospate Analogues," *J. Am. Chem. Soc.*, 120, 2780-2789 (1998).

Marquez et al., "Nucleosides with a Twist. Can Fixed Forms of Sugar Ring Pucker Influence Biological Activity in Nucleosides and Oligonucleotides," *J. Med. Chem.*, 39, 3739-3747 (1996).

Marquez et al., "Conformational Analysis of Nucleosides Constructed on a Bicyclo[3.1.0]Hexane Template, Structure-Antiviral Activity Analysis for the Northern and Southern Hemispheres of the Pseudorotational Cycle," *Nucleosides & Nucleotides*, 16 (7-9), 1431-1434 (1997).

Marquez et al., "Conformationally Restricted Nucleosides, The Reaction of Adenosine Deaminase with Substrates Built on a Bicyclo[3.1.0]Hexane Template." *Nucleosides & Nucleotides*, 18 (4 & 5), 521-530 (1999).

Miriam Webster Online Dictionary definition for phosphoryl <http://www.m-w.com/cgi-bin/dictionary?book=Dictionary&va=phosphoryl> downloaded from the Internet Feb. 23, 2004.

Moon et al., "Synthesis of Cyclopropyl-Fused Carbocyiclic Nucleosides via the Regioselective Opening of Cyclic Sulfites," *J. Org. Chem.*, 64, 4733-4741 (1999).

Nair et al., "C-2 Functionalized $N^6$-Cyclosubstituted Adenosines: Highly Selective Agonists for the Adenosine $A_1$ Receptor," *Tetrahedron*, 49 (11), 2169-2184 (1993).

Online Source "phosphonic acids" http://www.chemsoc.org/chembytes/goldbook/P04560.PDF downloaded from the Internet May 31, 2005.

PCT/US08/67683 International Search Report dated Oct. 17, 2008.

PCT/US08/67683 International Preliminary Report on Patentability dated Jan. 14, 2010.

Ravi et al., "Potent $P2X_7$ Receptor Antagonists: Tyrosyl Derivatives Synthesized Using a Sequential Parallel Synthetic Approach," *Drug Development Research*, 54, 75-87 (2001).

Registry File for RN 129687-40-7.

Registry File for RN 146038-94-0.

Registry File for RN 159967-50-7.

Rodriguez et al., "Conformationally Locked Nucleoside Analogues. Synthesis of Dideoxycarbocyclic Nucleoside Analogues Structurally Related to Neplanocin C," *J. Med. Chem.*, 37, 3389-3399 (1994).

Rodriguez et al., "Synthesis of Cyclopropane-fused Dideoxycarbocyclic Nucleosides Structurally Related to Neplanocin C," *Tetrahedron Letters*, 34 (39), 6233-6236 (1993).

Ruan, "Synthesis of Superabsorbent Resin by Ultraviolet Photopolymerization," *J. Appl. Polym. Sci.*, 92 (3), 1618-1624 (2004).

Shin et al., "Construction of the Bicyclo[3.1.0]hexane Template of a conformationally Locked Carbocyclic Adenosine via an Olefin Keto-Carbene Cycloaddition,"*J. Org. Chem.*, 65, 2172-2178 (2000).

Shuto et al., "Nucleosides and Nucleotides. 173. Synthesis of Cyclic IDP-carbocyclic-ribose, a Stable Mimic' of Cyclic ADP-ribose. Significant Facilitation of the Intramolecular Condensation Reaction of N-1-(Carbocyclic-ribosel)inosine 5',6"-Diphosphate Derivatives by an 8-Bromo-Substitution at the Hypoxanthine Moiety," *J. Org. Chem.*, 63, 1986-1994 (1998).

Siddiqui et al., "Synthesis, Conformational Analysis, and Biological Activity of a Rigid Carbocyclic Analogue of 2'-Deoxyaristeromycin Built on a Bicylclo[3.1.0]Hexane Template," *Nucleosides & Nucleotides*, 15 (1-3), 235-250 (1996).

Simone, "Oncology: Introduction," *Cecil Textbook of Medicine*, 20th Edition, 1, 1004-1010 (1996).

Sluggett, "(2,4,6-Trimethylbenzoyl)diphenylphosphine Oxide Phtochemistry, A Direct Time-Resolved Spectroscopic Study of Both Radical Fragments," *J. Amer. Chem. Soc.*, 117, 5148-5153 (1995).

Snowdy et al., "The Pharmaceutical Characterization of N6-((S))-3-Tretrahydrofuranyl) Adenosine, A Novel Adenosine Receptor Agonist," *Drug Devel. Res.*, 43, 30 (1998).

Spalluto et al., "Design, Synthesis and Biological Studies of a New Series of $N_6$-Arylcarbamoyl or $N_6$-Carboxamido-Adenosine-5'-Uronamindes as $A_3$ Adenosine Receptor Agonists," *Drug Devel. Res.*, 43, 30 (1998).

Sumiyoshi, "On the reactivity of phosphonyl radicals towards olefinic compounds," *Die Makromolekulare Chemie*, 186 (9), 1811-1823 (1985).

Suzuki et al., "7,8-Dihydro-8-ethyl-2-(3-noradamantyl)-4-propyl-1H-imidazo[2,1-1-1]purin-5(4H)-one: A Potent and Water-Soluble Adenosine $A_1$ Antagonist," *J. Med. Chem.* 35 (19), 3578-3581 (1992).

Theil et al., "Chemoenzymatic synthesis of carbocyclic nucleoside analogues with bicycle[3.1.0]hexyl residues," *J. Chem. Soc., Perkin Trans.* 1, 255-258 (1996).

Turro, "Single-phase primary electron spin polarization transfer in spin-trapping reactions," *Chemical Physics Letter*, 193, 546 (1992).

Van Bergen et al., "$A_3$ Receptors: Structure-Activity Relationships and Molecular Modeling," *Abstract of American Chemical Society Meeting*, Chicago, Illinois (Aug. 25, 1993).

Van Galen et al., "Xanthine-7-Ribosides as Adenosine Receptor Antagonists: Further Evidence for Adenosine's Anti Mode of Binding," *Cleosides & Nucleotides*, 10(5), 1191-1193 (1991).

Van Rhee et al., "Development of 1,4-Dyhydropyridines as Selective A.sub.3 Adenosine Receptor Antagonists" *Abstract from Purines*, (1996).

Van Rhee et al., "Interaction of 1,4-Dihydropyridine and Pyridine Derivatives with Adenosine Receptors: Selectivity for $A_3$ Receptors," *J. Med. Chem.*, 39, 2980-2989 (1996).

Volpini et al., "Potent and Selective Adenotin Agonists:2' and 3'-Deoxy Derivatives of 5'-N-Methylcarboxamidoadenosine (MECA)", *Abstract from Purines*, (1996).

Von Lubitz et al., "Reduction of postischemic brain damage and memory deficits following treatment with the selective adenosine $A_1$ receptor agonists," *European Journal of Pharmacology*, 54886, 1-6 (1996).

Ward et al., *48th Annual Meeting—Society of General Physiologist*, Abstract 33a (1994).

Williams et al., *6th International Symposium of Adenosine and Adenine Nucleotides New Frontiers in the 3rd Millennium*, Ferrara, Italy, May 19-24 *Drug Development Research*, 43 (1), 5 pages (25, 26, 28, 30, 34), (1998).

Zhou et al., "Molecular cloning and characterization of an adenosine receptor: The $A_3$ adenosine receptor," *Proc. Natl. Acad. Sci.*, 89, 7432-7436 (1992).

Fishman et al., "An agonist to the A3 adenosine receptor inhibits colon carcinoma growth in mice via modulation of GSK-3 beta and NF-kappa B," *Oncogene*, 23, 2465-2471 (2004).

Fredholm et al., "International Union of Pharmacology. XXV. Nomenclature and classification of adenosine receptors," *Pharmacol. Rev.*, 53 (4), 527-552 (2001).

Greenwald et al., "Poly(ethylene glycol) conjugated drugs and prodrugs: a comprehensive review," *Crit. Rev. Ther. Drug Carrier Syst.*, 17 (2), 101-161 (2000).

International Search Report, Application No. PCT/US2010/058746, dated Feb. 10, 2011.

Kim et al., "Toward multivalent signaling across G protein-coupled receptors from poly(amidoamine) dendrimers," *BioConjug. Chem.*, 19 (2), 406-411 (2008).

Klotz et al., "2-Chloro-$N^6$-[$^3$H]cyclopentyladenosine ([$^3$H]CCPA)—a high affinity agonist radioligand for $A_1$ adenosine receptors," *Naunyn Schmiedegergs. Arch. Pharmacol.*, 340 (6), 679-683 (1989).

Klutz et al., "Enhanced A3 adenosine receptor selectivity of multivalent nucleoside-dendrimer conjugates," *J. Nanobiotechnology*, 6 (1), 12 (2008).

Liu et al., "Evidence that the adenosine A3 receptor may mediate the protection afforded by preconditioning in the isolated rabbit heart," *Cardiovasc. Res.*, 28 (7), 1057-1061 (1994).

Melman et al., "Design of (N)-methanocarba adenosine 5'-uronamides as species-independent $A_3$ receptor-selective agonists," *Bioorganic & Med. Chem. Lett.*, 18 (9), 2813-2819 (2008).

Nordstedt et al., "A modification of a protein-binding method for rapid quantification of cAMP in cell-culture supernatants and body fluid," *Anal. Biochem.*, 189 (2), 231-234 (1990).

Ohta et al., "Role of G-protein-coupled adenosine receptors in downregulation of inflammation and protection from tissue damage," *Nature*, 414 (6866), 916-920 (2001).

Post et al., "Biochemical methods for detection and measurement of cyclic AMP and adenylyl cyclase activity," *Methods Mol. Biol.*, 126, 363-374 (2000).

Ramkumar et al., "The A3 adenosine receptor is the unique adenosine receptor which facilitates release of allergic mediators in mast cells," *J. Biol. Chem.*, 268 (23), 16887-16890 (1993).

Satija et al., "Pharmaceutical and biomedical potential of surface engineered dendrimers," *Crit. Rev. Ther. Drug Carrier Syst.*, 24 (3), 257-306 (2007).

Strickler et al., "Direct preconditioning of cultured chick ventricular myocytes. Novel functions of cardiac adenosine A2a and A3 receptors," *J. Clin. Invest.*, 98 (8), 1773-1779 (1996).

Tosh et al., "Polyamidoamine (PAMAM) Dendrimer Conjugates of "Clickable" Agonists of the A3 Adnosine Receptor and Coactivation of the $P2Y_{14}$ Receptor by a Tetheared Nucleotide," *Bioorg. Chem.*, 21, 372-384 (2010).

Tosh, et al., "2-Dialkynyl derivatives of (N)-methanocarba nucleosides: "Clickable" $A_3$ adenosine receptor-selective agonists," *Bioorg. Med. Chem.*, 18 (2), 508-517 (2009).

Tosh, et al., "Functionalized congeners of $A_3$ adenosine receptor-selective nucleosides containing a bicycle[3.1.0]hexane ring system," *J. Med. Chem.*, 52 (23), 7580-7592 (2009).

Tsolomitis et al., "Synthesis of 2-Substituted 3(2H)-Isothiazolones from 2-Substituted 5-Aroyl-3(2H)-Isothiazolones," *Heterocycles*, 25, 569-575 (1987).

Von Lubitz et al., "Adenosine A3 receptor stimulation and cerebral ischemia," *Eur. J. Pharmacol.*, 263 (1-2), 59-67 (1994).

Yang et al., "Dendrimers for pharmaceutical and biomedical applications," *J. Biomater. Sci. Polymer Edn.*, 17 (1-2), 3-19 (2006).

* cited by examiner

Reagents and Conditions: (i) diynes, PdCl2(Ph3P)2, CuI, Et3N, DMF, rt; (ii) FNPA, sodium ascorbate, CuSO$_4$·5H$_2$O, BuOH-CH$_2$Cl$_2$-H$_2$O, rt

METHANOCARBA ADENOSINE DERIVATIVES, PHARMACEUTICAL COMPOSITIONS, AND METHOD OF REDUCING INTRAOCULAR PRESSURE

CROSS-REFERENCE TO RELATED APPLICATIONS

This patent application is a U.S. National Phase of International Patent Application No. PCT/US10/58746, filed Dec. 2, 2010, which claims the benefit of U.S. Provisional Patent Application No. 61/266,084, filed Dec. 2, 2009, and U.S. Provisional Patent Application No. 61/313,961, filed Mar. 15, 2010, which are each incorporated by reference.

BACKGROUND OF THE INVENTION

Extracellular adenosine acts as a local modulator at four subtypes of adenosine receptors, namely, $A_1$, $A_{2A}$, $A_{2B}$, and $A_3$, which are involved in numerous physiological and pathophysiological processes. Fredholm et al., *Pharmacol. Rev.* 2001; 53:527-52. For example, adenosine attenuates the effects of ischemia in the heart and brain. Acting through the $A_{2A}$ adenosine receptor, it suppresses prolonged inflammation; Ohta et al., *Nature* 2001; 414:916-920; and causes vasodilation and inhibits platelet aggregation, thus increasing the amount of oxygen available to an organ under stress. Adenosine agonists selective for the $A_3$ adenosine receptor are of interest as cerebroprotective, cardioprotective, and anticancer agents. von Lubitz et al., *Eur. J. Pharmacol.,* 1994, 263:59-67; Liu et al., *Cardiovasc Res.,* 1994, 28:1057-61; Strickler et al., *J. Clin. Invest.,* 1996, 98:1773-9; Fishman et al., *Oncogene,* 2004, 23:2465-71.

The potential utility of $A_1$ and $A_2$-selective agents in therapeutic applications has been limited by accompanying side effects, given the ubiquitous nature of the $A_1$ and $A_2$ receptors. The distribution of the $A_3$ adenosine receptor, by contrast, is fairly limited, being found primarily in the CNS, brain, testes, and immune system, where it appears to be involved in the modulation of release from mast cells of mediators of the immediate hypersensitivity reaction (Ramkumar et al., *J. Biol. Chem.,* 268, 16887-16890 (1993)). The limited distribution of the $A_3$ adenosine receptor provides a basis for predicting that $A_3$-selective compounds may be more useful than $A_1$- and $A_2$-selective compounds as potential therapeutic agents.

Accordingly, there is a great interest for finding $A_3$ adenosine receptor agonists, as shown by the patenting activity in this area; see, for example, U.S. Pat. Nos. 5,773,423 and 5,688,774; and U.S. Published Patent Application No. 2003/0216412 A1. Therefore, there is a desire for $A_3$ adenosine receptor agonists, especially those that are selective to $A_3$ adenosine receptor over the $A_1$ and $A_2$ adenosine receptors.

Attempts have been made to covalently link certain drugs, for example, taxol, cisplatin, methotrexate, and ibuprofen, to dendrimers, which are polymers made from branched monomers through the iterative organic synthesis by adding one layer (i.e., generation) at each step to provide a symmetrical structure. Such dendrimer conjugates have one or more advantages, for example, altered pharmacokinetics, decreased toxicity, and increased solubility. Agonists and antagonists of the receptors of the G-protein coupled receptor (GPCR) superfamily are useful in the treatment of a number of diseases, for example, the agonist of one member of the GPCR superfamily, the $A_3$ adenosine receptor, is useful for treating a number of diseases as set forth in the above patents and published application. There is a desire to obtain dendrimer conjugates of agonists and antagonists of the GPCR superfamily of receptors.

BRIEF SUMMARY OF THE INVENTION

The invention provides a compound of the formula (I):

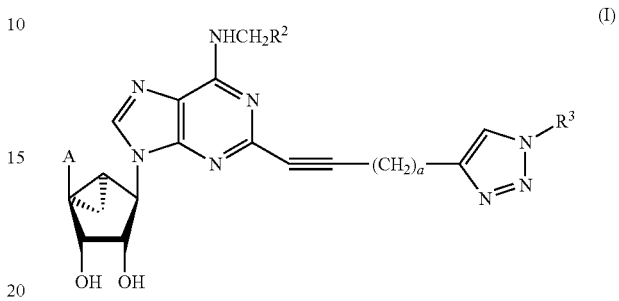

wherein A is hydrogen or —CONHR$^1$, wherein R$^1$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, R$^2$ is a phenyl group optionally substituted with one or more halogen atoms, a is an integer of 2 to 10, R$^3$ is selected from the group consisting of phenyl optionally substituted with 1, 2, 3, 4, or 5 substituents selected from the group consisting of halogen, NO$_2$, NR$^4$R$^5$, COOH, COR$^7$, $C_1$-$C_6$ alkyl, $C_3$-$C_8$ cycloalkyl, adamantyl, $C_6$-$C_{10}$ aryl, isothiocyanato, heteroaryl, and heterocyclyl, benzyl optionally substituted with 1, 2, 3, 4, or 5 substituents selected from the group consisting of halogen, NO$_2$, NR$^4$R$^5$, COR$^E$, $C_1$-$C_6$ alkyl, $C_3$-$C_8$ cycloalkyl, adamantyl, $C_6$-$C_{10}$ aryl, heteroaryl, and heterocyclyl, and a group of the structure: —(CH$_2$)$_b$NR$^7$R$^8$, wherein b is 1 to 6, R$^4$ and R$^5$ are independently hydrogen or $C_1$-$C_6$ alkyl, R$^6$ is $C_1$-$C_6$ alkyl optionally substituted with halogen, and R$^7$ and R$^8$ are independently selected from the group consisting of hydrogen, $C_1$-$C_6$ alkyl, and $C_2$-$C_6$ acyl, or a pharmaceutically acceptable salt thereof.

The invention also provides a compound of the formula (II):

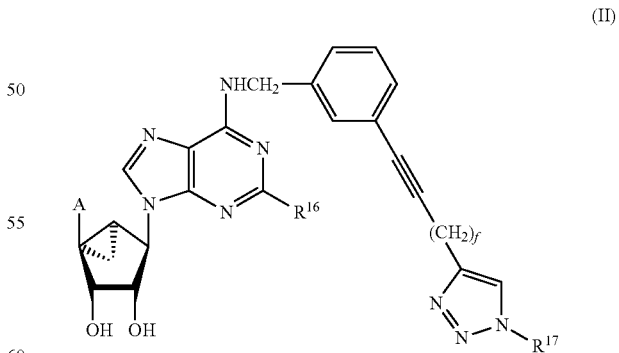

wherein A is hydrogen or —CONHR$^{15}$,

R$^{15}$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, R$^{16}$ is hydrogen, halo, or $C_1$-$C_6$ alkyl, f is an integer of 2 to 10, $R^{17}$ is selected from the group consisting of phenyl optionally substituted with 1, 2, 3, 4, or 5 substituents selected from the group consisting of halogen, $NO_2$, $NR^{18}R^{19}$, COOH, $COR^{20}$, $C_1$-$C_6$ alkyl, $C_3$-$C_8$ cycloalkyl, adamantyl, $C_6$-$C_{10}$ aryl, isothiocyanato, heteroaryl, and heterocyclyl, benzyl optionally substituted with 1, 2, 3, 4, or 5 substituents selected from the group consisting of halogen, $NO_2$, $NR^{18}R^{19}$, $COR^{20}$, $C_1$-$C_6$ alkyl, $C_3$-$C_8$ cycloalkyl, adamantyl, $C_6$-$C_{10}$ aryl, heteroaryl, and heterocyclyl, and a group of the structure: —$(CH_2)_b NR^{21}R^{22}$, $R^{18}$ and $R^{19}$ are independently hydrogen or $C_1$-$C_6$ alkyl, $R^{20}$ is $C_1$-$C_6$ alkyl optionally substituted with halogen, and $R^{21}$ and $R^{22}$ are independently selected from the group consisting of hydrogen, $C_1$-$C_6$ alkyl, and $C_2$-$C_6$ acyl, or a pharmaceutically acceptable salt thereof.

The invention further provides a compound of the formula (I'):

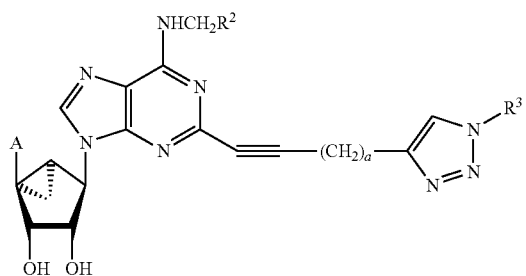

wherein A is hydrogen or —$CONHR^1$, $R^1$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, $R^2$ is a phenyl group optionally substituted with one or more halogen atoms, a is an integer of 2 to 10, $R^3$ is a group of the formula L-$R^9$, wherein L is a $C_2$-$C_{20}$ alkylene chain optionally including in the chain one or more oxygen atoms, nitrogen atoms, or a combination of oxygen and nitrogen atoms, and further optionally including one or more carbonyl groups, and $R^9$ is a biotinylated, chemically reactive, or fluorescent moiety.

The invention additionally provides a compound of the formula (II'):

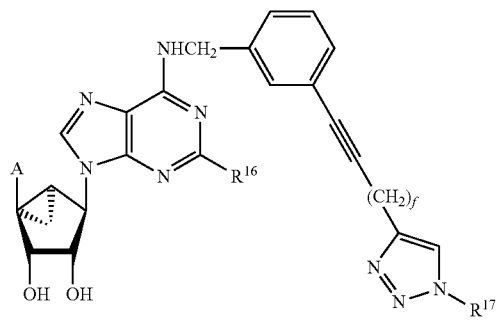

wherein A is hydrogen or —$CONHR^{15}$, $R^{15}$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, f is an integer of 2 to 10, $R^{16}$ is hydrogen, halo, or $C_1$-$C_6$ alkyl, $R^{17}$ is a group of the formula L-$R^{23}$, wherein L is a $C_2$-$C_{20}$ alkylene chain optionally including in the chain one or more oxygen atoms, nitrogen atoms, or a combination of oxygen and nitrogen atoms, and further optionally including one or more carbonyl groups, and $R^{23}$ is a biotinylated, chemically reactive, or fluorescent moiety.

The invention further provides a compound of the formula (V):

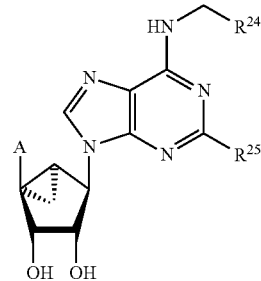

wherein A is hydrogen or —$CONHR^{26}$, $R^{26}$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, $R^{25}$ is hydrogen, halo, or $C_1$-$C_6$ alkyl,

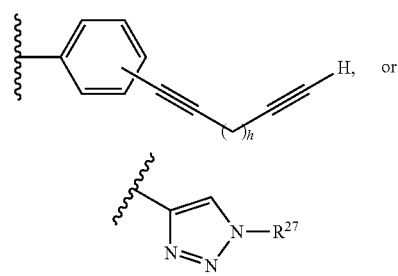

$R^{24}$ is C≡CH, C≡C—$(CH_2)_g$—C≡CH, wherein $R^{27}$ is selected from the group consisting of phenyl optionally substituted with 1, 2, 3, 4, or 5 substituents selected from the group consisting of halogen, $NO_2$, $NR^{28}R^{29}$, COOH, $COR^{30}$, $C_1$-$C_6$ alkyl, $C_3$-$C_8$ cycloalkyl, adamantyl, $C_6$-$C_{10}$ aryl, isothiocyanato, heteroaryl, and heterocyclyl, benzyl optionally substituted with 1, 2, 3, 4, or 5 substituents selected from the group consisting of halogen, $NO_2$, $NR^{28}R^{29}$, $COR^{30}$, $C_1$-$C_6$ alkyl, $C_3$-$C_8$ cycloalkyl, adamantyl, $C_6$-$C_{10}$ aryl, heteroaryl, and heterocyclyl, and a group of the structure:

—$(CH_2)_b NR^{31}R^{32}$, wherein b is an integer of 1 to 6, g is an integer of 1 to 10, h is an integer of 1 to 10, $R^{28}$ and $R^{29}$ are independently hydrogen or $C_1$-$C_6$ alkyl, $R^{30}$ is $C_1$-$C_6$ alkyl optionally substituted with halogen, and $R^{31}$ and $R^{32}$ are independently selected from the group consisting of hydrogen, $C_1$-$C_6$ alkyl, and $C_2$-$C_6$ acyl, or a pharmaceutically acceptable salt thereof.

The invention also provides a pharmaceutical composition comprising a compound or salt of the invention and a pharmaceutically acceptable carrier.

The invention further provides a method of treating or preventing a disease or adverse condition which is treatable or preventable by agonizing or antagonizing a receptor of the GPCR superfamily in a mammal comprising administering to the mammal an effective amount of the compound or salt of the invention.

The invention additionally provides a conjugate comprising a dendrimer, at least one GPCR ligand covalently linked to the dendrimer, and optionally one or more surface modifying moieties covalently linked to the dendrimer, wherein the at least one ligand is a functionalized congener of an agonist of an adenosine receptor.

The invention also provides a pharmaceutical composition comprising a conjugate of the invention and a pharmaceutically acceptable carrier.

The invention further provides a method of treating a disease which is treatable by agonizing or antagonizing a receptor of the GPCR superfamily in a mammal comprising administering to the mammal an effective amount of the conjugate of the invention.

The invention additionally provides a method of preparing a dendrimer conjugate comprising a $A_3AR$ receptor antagonist and a dendrimer that is covalently linked to the $A_3AR$ receptor antagonist through a triazole moiety.

DETAILED DESCRIPTION OF THE INVENTION

Figure 1:
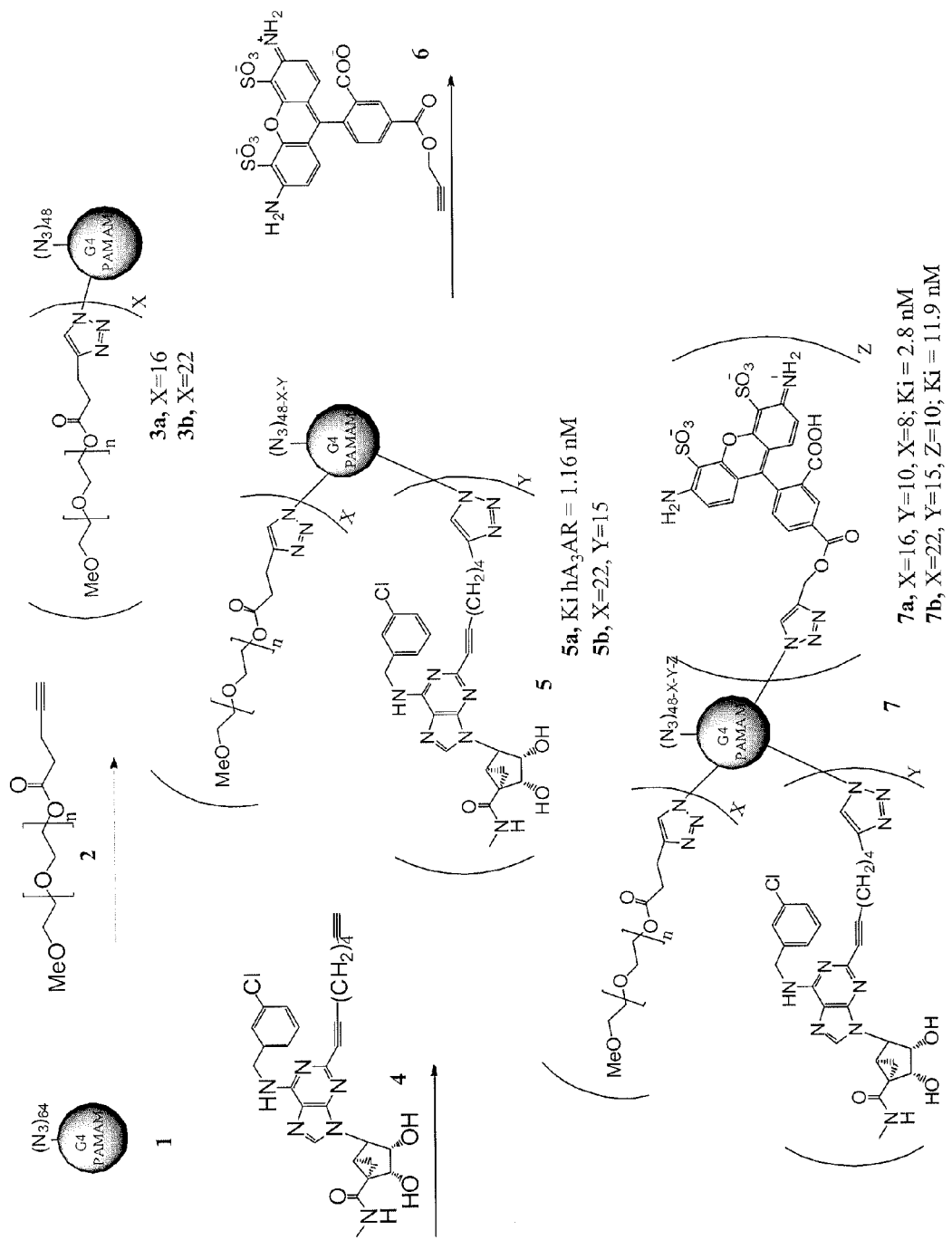
FIG. 1 illustrates synthetic scheme to prepare dendrimer conjugates 3, 5a, 5b, 7a, and 7b in accordance with an embodiment of the invention.
Figure 2:
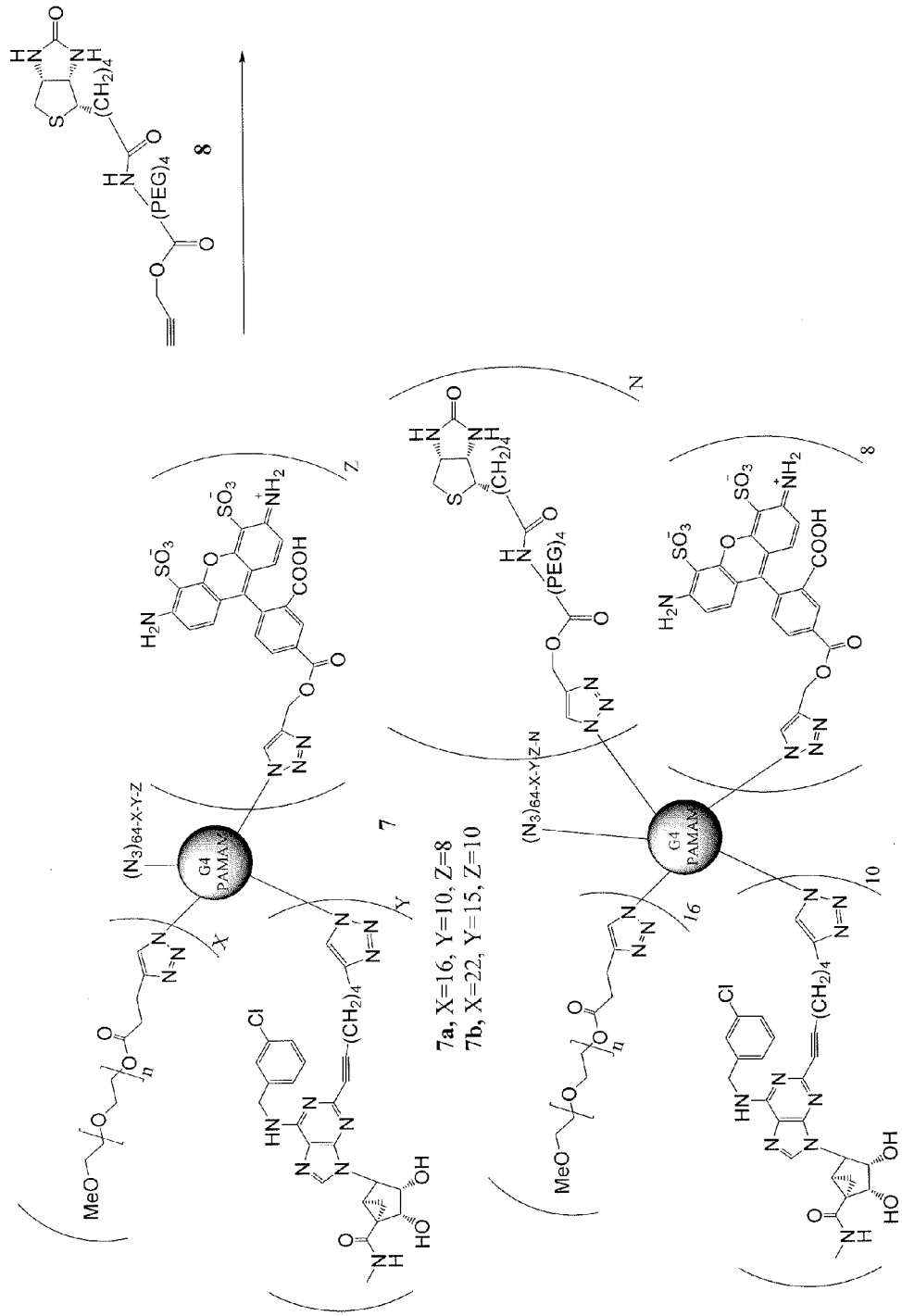
FIG. 2 illustrates a synthetic scheme to prepare dendrimer conjugates 9a and 9b in accordance with an embodiment of the invention.
Figure 3:
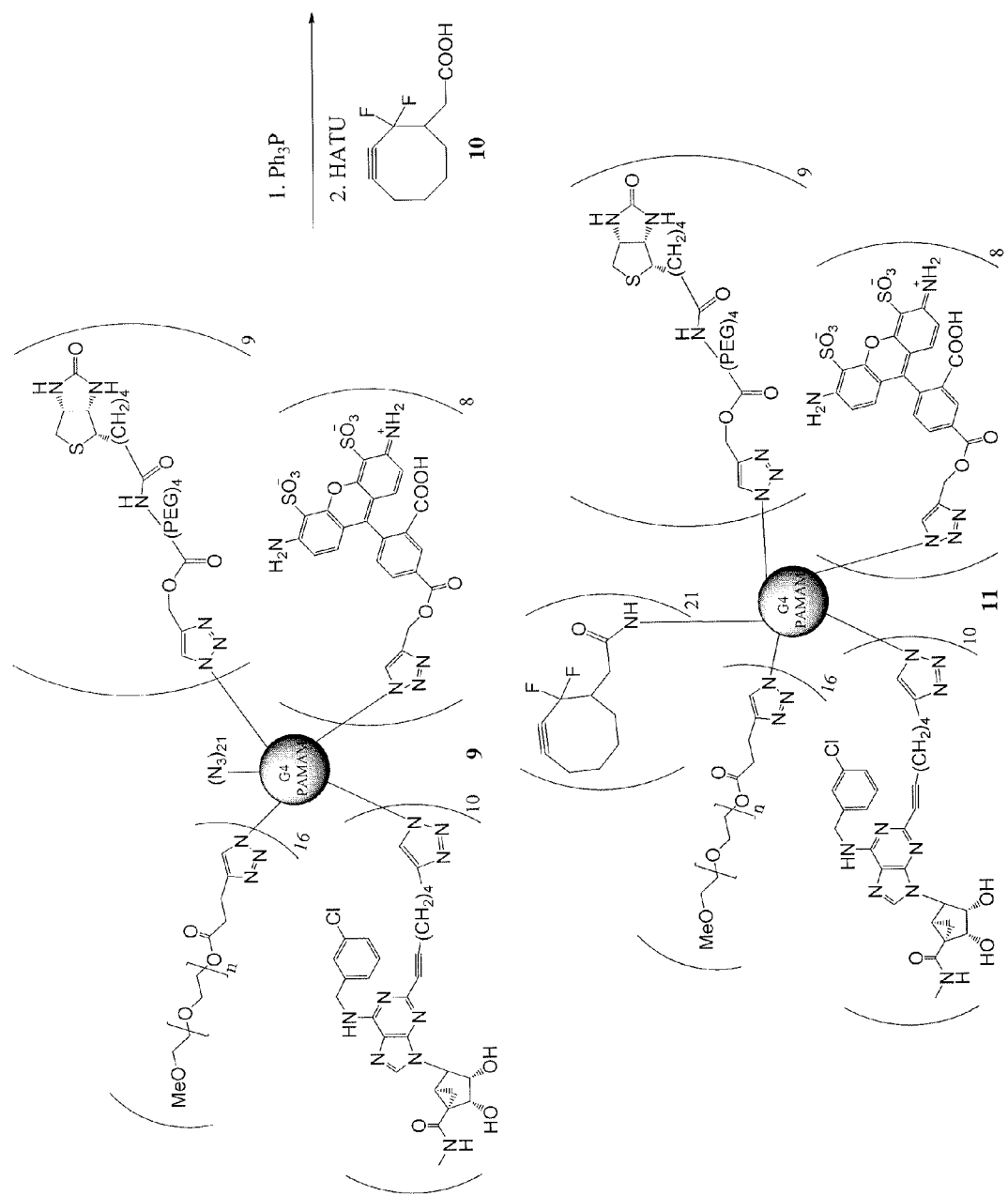
FIG. 3 illustrates a synthetic scheme to prepare dendrimer conjugate 11 in accordance with an embodiment of the invention.
Figure 4:
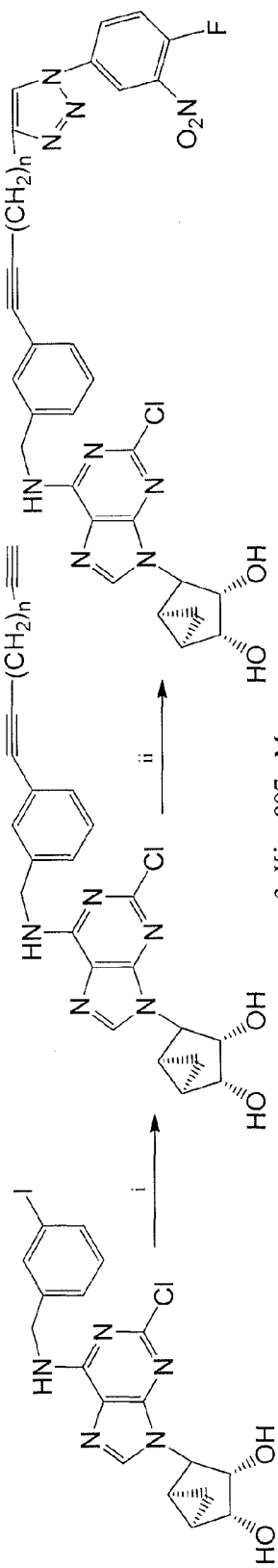
FIG. 4 illustrates a synthetic scheme to prepare $N^6$-benzyl compounds in accordance with an embodiment of the invention.
Figure 5:
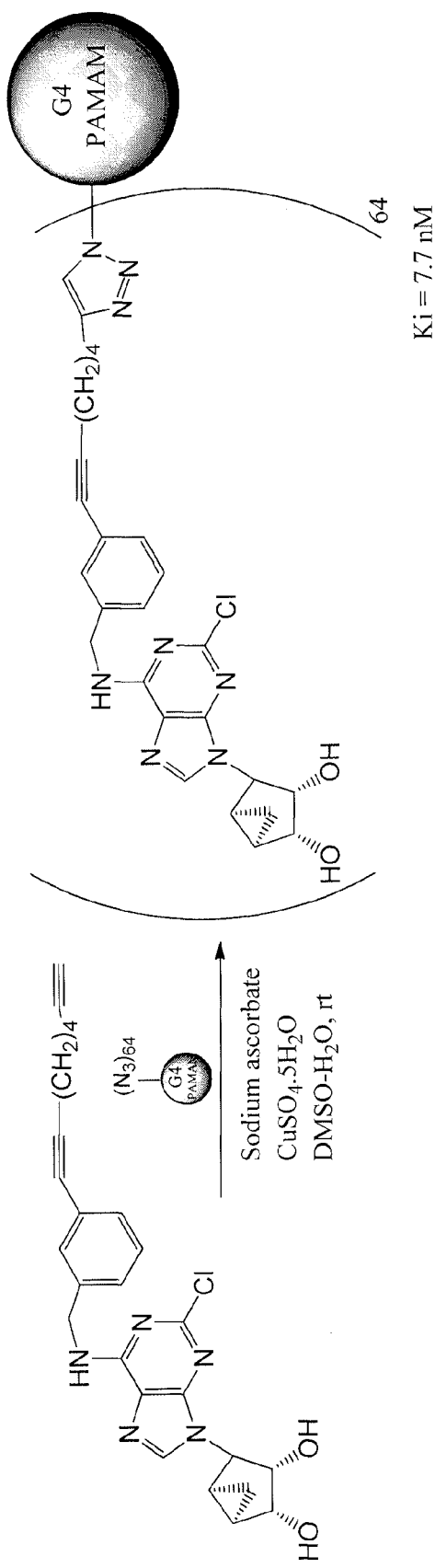
FIG. 5 illustrates another synthetic scheme to prepare dendrimer conjugates in accordance with an embodiment of the invention.
Figure 6A:
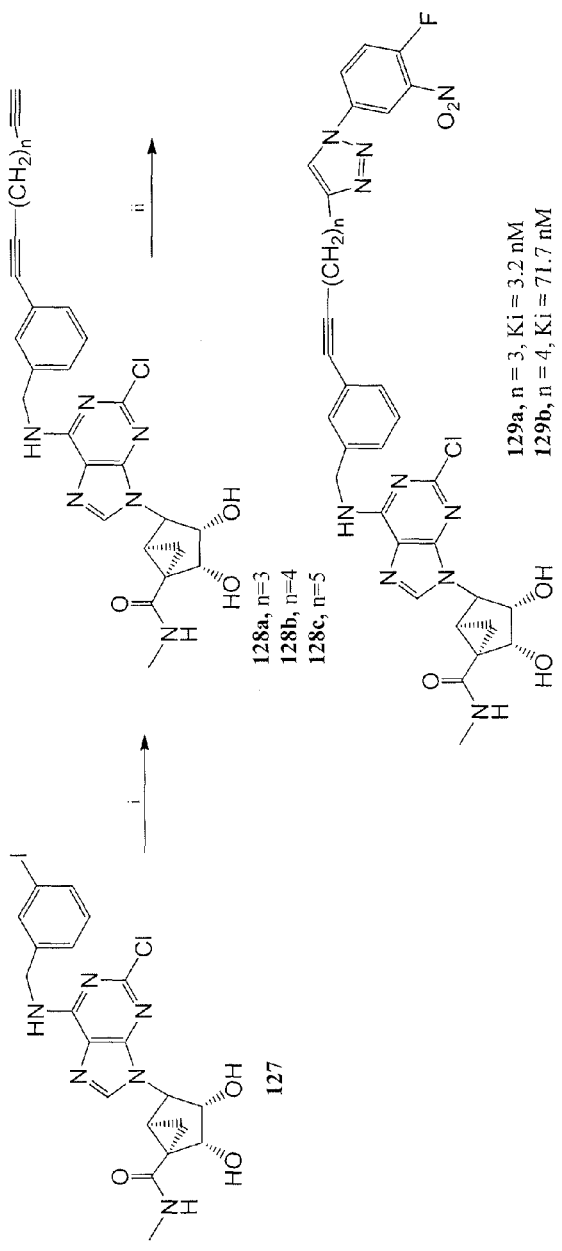
FIG. 6A illustrates a synthetic scheme to prepare compounds 129a-c in accordance with an embodiment of the invention.
Figure 6B:
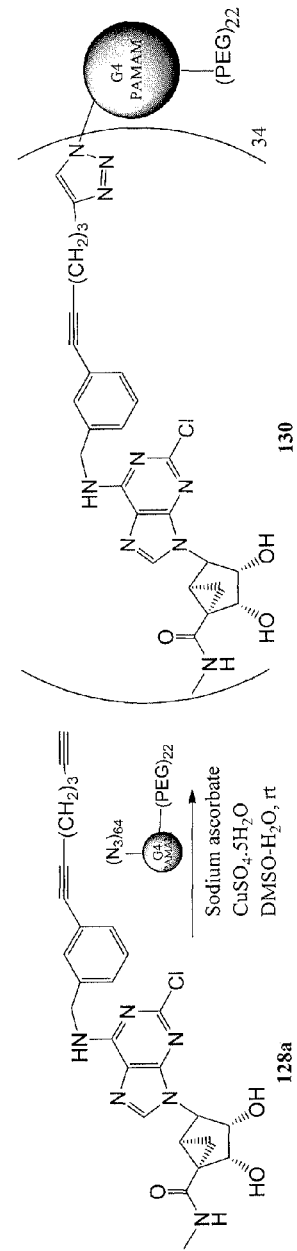
FIG. 6B illustrates a synthetic scheme to prepare dendrimer conjugate 130 in accordance with an embodiment of the invention.
Figure 7:
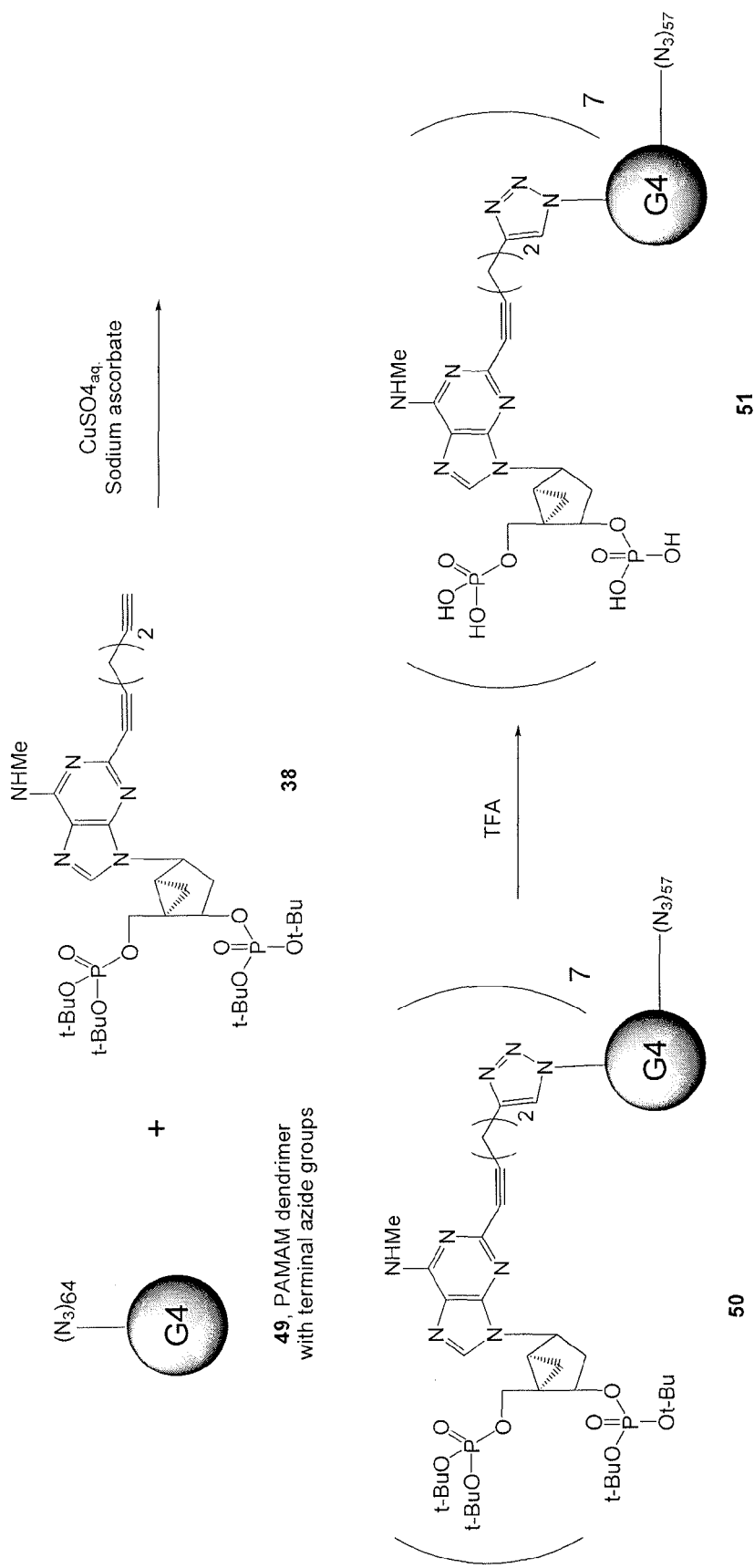
FIG. 7 illustrates a synthetic scheme to prepare dendrimer conjugates 50 and 51 in accordance with an embodiment of the invention.

In accordance with an embodiment, the invention provides a compound of the

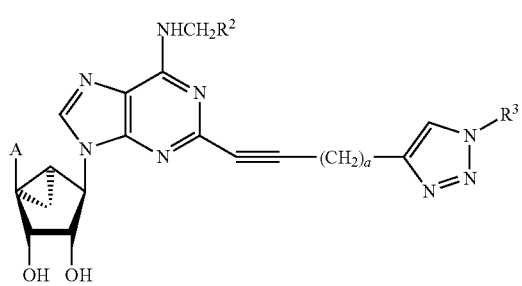

(I)

wherein A is hydrogen or —CONHR$^1$, wherein R$^1$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, R$^2$ is a phenyl group optionally substituted with one or more halogen atoms, a is an integer of 2 to 10, R$^3$ is selected from the group consisting of phenyl optionally substituted with 1, 2, 3, 4, or 5 substituents selected from the group consisting of halogen, NO$_2$, NR$^4$R$^5$, COOH, COR$^7$, C$_1$-C$_6$ alkyl, C$_3$-C$_8$ cycloalkyl, adamantyl, C$_6$-C$_{10}$ aryl, isothiocyanato, heteroaryl, and heterocyclyl, benzyl optionally substituted with 1, 2, 3, 4, or 5 substituents selected from the group consisting of halogen, NO$_2$, NR$^4$R$^5$, COR$^6$, C$_1$-C$_6$ alkyl, C$_3$-C$_8$ cycloalkyl, adamantyl, C$_6$-C$_{10}$ aryl, heteroaryl, and heterocyclyl, and a group of the structure: —(CH$_2$)$_b$NR$^7$R$^8$, R$^4$ and R$^5$ are independently hydrogen or C$_1$-C$_6$ alkyl, R$^6$ is C$_1$-C$_6$ alkyl optionally substituted with halogen, and R$^7$ and R$^8$ are independently selected from the group consisting of hydrogen, C$_1$-C$_6$ alkyl, and C$_2$-C$_6$ acyl, or a pharmaceutically acceptable salt thereof.

The invention, in accordance with an embodiment, further provides a compound of the formula (I'):

(I')

wherein A is hydrogen or —CONHR$^1$,

R$^1$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, R$^2$ is a phenyl group optionally substituted with one or more halogen atoms, a is an integer of 2 to 10, R$^3$ is a group of the formula L-R$^9$, wherein L is a C$_2$-C$_{20}$ alkylene chain optionally including in the chain one or more oxygen atoms, nitrogen atoms, or a combination of oxygen and nitrogen atoms, and further optionally including one or more carbonyl groups, and R$^9$ is a biotinylated, chemically reactive, or fluorescent moiety.

In accordance with an embodiment, the invention provides a compound of the (II)

wherein A is hydrogen or —CONHR$^{15}$,

R$^{15}$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, R$^{16}$ is hydrogen, halo, or C$_1$-C$_6$ alkyl, f is an integer of 2 to 10, R$^{17}$ is selected from the group consisting of phenyl optionally substituted with 1, 2, 3, 4, or 5 substituents selected from the group consisting of halogen, NO$_2$, NR$^{18}$R$^{19}$, COOH, COR$^{20}$, C$_1$-C$_6$ alkyl, C$_3$-C$_8$ cycloalkyl, adamantyl, C$_6$-C$_{10}$ aryl, isothiocyanato, heteroaryl, and heterocyclyl, benzyl optionally substituted with 1, 2, 3, 4, or 5 substituents selected from the group consisting of halogen, NO$_2$, NR$^{18}$R$^{19}$, COR$^{20}$, C$_1$-C$_6$ alkyl, C$_3$-C$_8$ cycloalkyl, C$_6$-C$_{10}$ aryl, heteroaryl, and heterocyclyl, and a group of the structure: —(CH$_2$)$_b$NR$^{21}$R$^{22}$, R$^{18}$ and R$^{19}$ are independently hydrogen or C$_1$-C$_6$ alkyl, R$^{20}$ is C$_1$-C$_6$ alkyl optionally substituted with halogen, and R$^{21}$ and R$^{22}$ are independently selected from the group consisting of hydrogen, C$_1$-C$_6$ alkyl, and C$_2$-C$_6$ acyl, or a pharmaceutically acceptable salt thereof.

The invention further provides a compound of the formula (II'):

(II')

wherein A is hydrogen or —CONHR$^{15}$,

R$^{15}$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, f is an integer of 2 to 10, R$^{16}$ is hydrogen, halo, or C$_1$-C$_6$ alkyl, R$^{17}$ is a group of the formula L-R$^{23}$, wherein L is a C$_2$-C$_{20}$ alkylene chain optionally including in the chain one or more oxygen atoms, nitrogen atoms, or a combination of oxygen and nitrogen atoms, and further optionally including one or more carbonyl groups, and R$^{23}$ is a biotinylated, chemically reactive, or fluorescent moiety.

In accordance with an embodiment, the invention provides a compound of the formula (V):

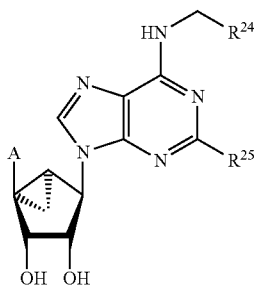

wherein A is hydrogen or —CONHR$^{26}$,

R$^{26}$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, R$^{25}$ is hydrogen, halo, or C$_1$-C$_6$ alkyl,

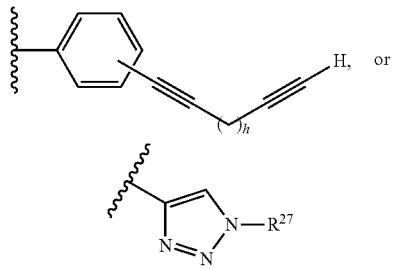

R$^{24}$ is C≡CH, C≡C—(CH$_2$)$_g$—C≡CH, wherein R$^{27}$ is selected from the group consisting of phenyl optionally substituted with 1, 2, 3, 4, or 5 substituents selected from the group consisting of halogen, NO$_2$, NR$^{28}$R$^{29}$, COOH, COR$^{30}$, C$_1$-C$_6$ alkyl, C$_3$-C$_8$ cycloalkyl, adamantyl, C$_6$-C$_{10}$ aryl, isothiocyanato, heteroaryl, and heterocyclyl, benzyl optionally substituted with 1, 2, 3, 4, or 5 substituents selected from the group consisting of halogen, NO$_2$, NR$^{28}$R$^{29}$, COR$^{30}$, C$_1$-C$_6$ alkyl, C$_3$-C$_8$ cycloalkyl, adamantyl, C$_6$-C$_{10}$ aryl, heteroaryl, and heterocyclyl, and a group of the structure:

—(CH$_2$)$_b$NR$^{31}$R$^{32}$, wherein b is an integer of 1 to 6, g is an integer of 1 to 10, h is an integer of 1 to 10, R$^{28}$ and R$^{29}$ are independently hydrogen or C$_1$-C$_6$ alkyl, R$^{31}$ is C$_1$-C$_6$ alkyl optionally substituted with halogen, and R$^{31}$ and R$^{32}$ are independently selected from the group consisting of hydrogen, C$_1$-C$_6$ alkyl, and C$_2$-C$_6$ acyl, or a pharmaceutically acceptable salt thereof.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkylene," as used herein, means a straight-chain or branched alkyl substituent containing from, for example, 1 to about 6 carbon atoms, preferably from 1 to about 4 carbon atoms, and is connected to two or more substituents at two or more different positions on the alkylene group.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "alkenylene," as used herein, means a straight-chain or branched alkenyl substituent containing from, for example, 2 to about 6 carbon atoms, preferably from 2 to about 4 carbon atoms, and is connected to two or more substituents at two or more different positions on the alkenylene group.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "alkynylene," as used herein, means a straight-chain or branched alkynyl substituent containing from, for example, 2 to about 6 carbon atoms, preferably from 2 to about 4 carbon atoms, and is connected to two or more substituents at two or more different positions on the alkynylene group.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The term "cycloalkenyl," as used herein, means the same as the term "cycloalkyl," however one or more double bonds are present. Examples of such substituents include cyclopentenyl and cyclohexenyl. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocylic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Preferably, the heterocyclyl group is an aromatic heterocyclyl group. Non-limiting examples of suitable heterocyclyl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, and quinazolinyl. The heterocyclyl group is optionally substituted with 1, 2, 3, 4, or 5 substituents as recited herein, wherein the optional substituent can be present at any open position on the heterocyclyl group.

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule.

The term "arylene" refers to an unsubstituted or substituted aromatic carbocyclic substituent as defined herein, wherein the arylene substituent is connected to two or more substituents at two or more different positions on the arylene group. For example, 1,2-dichlorobenzene can be considered to be a phenylene (arylene) group substituted with two chlorine atoms.

The term "heteroaryl" refers to an unsubstituted or substituted aromatic heterocyclic substituent, as commonly understood in the art. It is understood that the term heteroaryl applies to cyclic heterocyclic substituents that are planar and comprise 4n+2 π electrons, according to Hacker s Rule.

In accordance with a preferred embodiment, $R^1$ is methyl.

In accordance with a preferred embodiment, $R^2$ is 3-chlorophenyl.

In accordance with an embodiment, a is 3 or 4.

In certain embodiments, $R^3$ is phenyl substituted with 1, 2, 3, 4, or 5 substituents selected from the group consisting of halogen, $NO_2$, $NR^4R^5$, COOH, $COR^7$, $C_1$-$C_6$ alkyl, $C_3$-$C_8$ cycloalkyl, adamantyl, $C_6$-$C_{10}$ aryl, 4-isothiocyanato, heteroaryl, and heterocyclyl.

In certain preferred embodiments, $R^3$ is selected from the group consisting of 3-nitro-4-fluoro, 4-amino, 4-carboxy, 4-bromoacetyl, adamantyl, and 4-isothiocyanato.

In certain embodiments, $R^3$ is selected from the group consisting of benzyl substituted with 1, 2, 3, 4, or 5 substituents selected from the group consisting of halogen, $NO_2$, $NR^4R^5$, $COR^6$, $C_1$-$C_6$ alkyl, $C_3$-$C_8$ cycloalkyl, adamantyl, $C_6$-$C_{10}$ aryl, heteroaryl, and heterocyclyl.

In certain preferred embodiments, $R^3$ is benzyl substituted with heterocyclyl.

In accordance with a preferred embodiment, $R^3$ is 4-(3-oxoisothiazol-2(3h)-yl)benzyl.

In certain embodiments, $R^3$ is —$(CH_2)_b NR^7R^8$.

In certain preferred embodiments, b is 2, 3, or 4.

In certain preferred embodiments, $R^7$ and $R^8$ are both hydrogen.

In certain preferred embodiments, $R^7$ is hydrogen and $R^8$ is acetyl.

In certain embodiments, $R^3$ is L-$R^9$.

In certain preferred embodiments, L is —$(CH_2)_6 NHCO(CH_2)_4$—.

In certain preferred embodiments, L is —$CONH(CH_2)_2[O(CH_2)_2]_4 NH$—.

In accordance with a preferred embodiment, $R^9$ is (5-(3aS, 4S, 6aR)-oxohexahydro-1H-thieno[3,4-d]imidazol-4-yl.

In certain embodiments, $R^9$ is a rotaxane derivative.

In certain embodiments, $R^9$ is a fluorescent marker.

In accordance with a preferred embodiment, $R^{15}$ is methyl.

In certain preferred embodiments, $R^{16}$ is hydrogen, halo, or $C_1$-$C_6$ alkyl.

In accordance with an embodiment, f is 3 or 4.

In certain embodiments, $R^{17}$ is phenyl substituted with 1, 2, 3, 4, or 5 substituents selected from the group consisting of halogen, $NO_2$, $NR^{18}R^{19}$, COOH, $COR^{20}$, $C_1$-$C_6$ alkyl, $C_3$-$C_8$ cycloalkyl, adamantyl, $C_6$-$C_{10}$ aryl, 4-isothiocyanato, heteroaryl, and heterocyclyl.

In certain preferred embodiments, $R^{17}$ is selected from the group consisting of 3-nitro-4-fluoro, 4-amino, 4-carboxy, 4-bromoacetyl, adamantyl, and 4-isothiocyanato.

In certain embodiments, $R^{17}$ is selected from the group consisting of benzyl substituted with 1, 2, 3, 4, or 5 substituents selected from the group consisting of halogen, $NO_2$, $NR^{18}R^{19}$, $COR^{20}$, $C_1$-$C_6$ alkyl, $C_3$-$C_8$ cycloalkyl, adamantyl, $C_6$-$C_{10}$ aryl, heteroaryl, and heterocyclyl.

In certain preferred embodiments, $R^{17}$ is benzyl substituted with heterocyclyl.

In accordance with a preferred embodiment, $R^{17}$ is 4-(3-oxoisothiazol-2(3h)-yl)benzyl.

In certain embodiments, $R^{17}$ is —$(CH_2)_b NR^{21}R^{22}$.

In certain preferred embodiments, b is 2, 3, or 4.

In certain preferred embodiments, $R^{21}$ and $R^{22}$ are both hydrogen.

In certain preferred embodiments, $R^{21}$ is hydrogen and $R^{22}$ is acetyl.

In certain embodiments, $R^{17}$ is L-$R^{23}$.

In certain preferred embodiments, L is —(CH$_2$)$_6$NHCO(CH$_2$)$_4$—.

In certain preferred embodiments, L is —CONH(CH$_2$)$_2$[O(CH$_2$)$_2$]$_4$NH—.

In accordance with a preferred embodiment, $R^{23}$ is (5-(3aS, 4S, 6aR)-oxohexahydro-1H-thieno[3,4-d]imidazol-4-yl.

In certain embodiments, $R^{23}$ is a rotaxane derivative.

In certain embodiments, $R^{23}$ is a fluorescent marker.

In certain embodiments, $R^{24}$ is C≡CH.

In certain embodiments, $R^{24}$ is C≡C—(CH$_2$)$_g$C≡CH. In certain embodiments, g is an interger of 1 to 10. In certain preferred embodiments, g is an integer of 3 to 5.

In certain embodiments, $R^{24}$ is

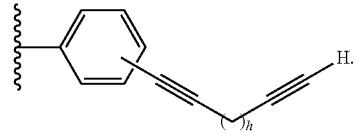

In certain embodiments, h is an integer of 1 to 10. In certain preferred embodiments, h is an integer of 3 to 5.

In certain embodiments, $R^{24}$ is

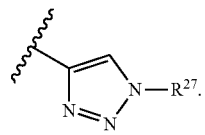

In certain preferred embodiments, b is 3 or 4.

In certain embodiments, $R^{27}$ is phenyl substituted with 1, 2, 3, 4, or 5 substituents selected from the group consisting of halogen, NO$_2$, NR$^{28}$R$^{29}$, COOH, COR$^{30}$, C$_1$-C$_6$ alkyl, C$_3$-C$_8$ cycloalkyl, adamantyl, C$_6$-C$_{10}$ aryl, 4-isothiocyanato, heteroaryl, and heterocyclyl.

In certain embodiments, $R^{27}$ is phenyl substituted with a substituent or substituents selected from the group consisting of 3-nitro-4-fluoro, 4-amino, 4-carboxy, 4-bromoacetyl, adamantyl, and 4-isothiocyanato.

In certain preferred embodiments, $R^{27}$ is benzyl substituted with 1, 2, 3, 4, or 5 substituents selected from the group consisting of halogen, NO$_2$, NR$^{18}$R$^{19}$, COR$^N$, C$_1$-C$_6$ alkyl, C$_3$-C$_8$ cycloalkyl, adamantyl, C$_6$-C$_{10}$ aryl, heteroaryl, and heterocyclyl.

In accordance with a preferred embodiment, $R^{27}$ is benzyl substituted with heterocyclyl.

In certain embodiments, $R^{27}$ is —(CH$_2$)$_b$NR$^{31}$R$^{32}$.

In certain preferred embodiments, b is 2, 3, or 4.

In certain embodiments, $R^{31}$ and $R^{32}$ are both hydrogen.

In certain embodiments, $R^{31}$ is hydrogen and $R^{32}$ is acetyl.

The invention also provides a conjugate comprising a dendrimer, at least one GPCR ligand covalently linked to the dendrimer, and optionally one or more surface modifying moieties covalently linked to the dendrimer, wherein the at least one ligand is a functionalized congener of GPCR.

In accordance with a preferred embodiment, the at least one ligand is a functionalized congener of an agonist of an A$_3$ adenosine receptor.

In certain preferred embodiments, the dendrimer is a poly(amidoamine) (PAMAM) dendrimer.

In certain preferred embodiments, the PAMAM dendrimer is of generation 2 to 10.

In certain preferred embodiments, the PAMAM dendrimer is of generation 2 to 6.

In certain more preferred embodiments, the PAMAM dendrimer is of generation 2, 2.5, 3, or 4.

In certain embodiments, the A$_3$ adenosine receptor agonist is of the formula (III):

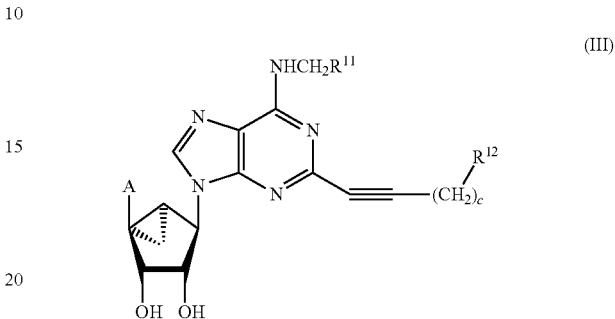

wherein A is hydrogen or —CONHR$^{10}$, wherein R$^{10}$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, R$^{11}$ is a phenyl group optionally substituted with halogen, R$^{12}$ is selected from the group consisting of —C≡CH, —CONH(CH$_2$)$_d$NH$_2$, and —COOH, and c and d are independently integers of 2 to 10.

In accordance with a preferred embodiment, A is —CONHR$^{10}$, R$^{11}$ is 3-chlorophenyl, and R$^{12}$ is —C≡CH.

In accordance with a preferred embodiment, c is 4.

In accordance with a preferred embodiment, A is —CONHR$^{10}$, R$^{11}$ is 3-chlorophenyl, R$^3$ is —CONH(CH$_2$)$_d$NH$_2$, c is 2 or 3, and d is 2.

In accordance with a preferred embodiment, A is —CONHR$^{10}$, R$^{11}$ is 3-chlorophenyl, R$^{12}$ is —COOH, and c is 3.

In certain embodiments, the A$_3$ adenosine receptor agonist is of the formula (IV):

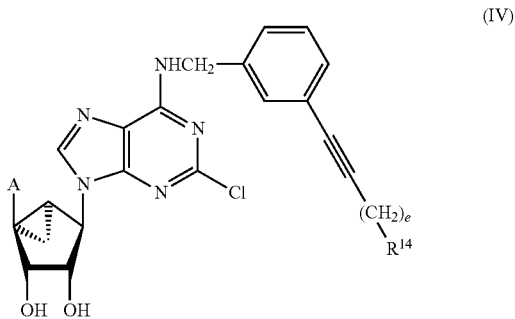

wherein A is hydrogen or —CONHR$^{13}$, wherein R$^{13}$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, wherein R$^{14}$ is —CONH(CH$_2$)$_d$NH$_2$ or —COOH, and d and e are integers of 2 to 10.

In accordance with a preferred embodiment, R$^{14}$ is —CONH(CH$_2$)$_d$NH$_2$.

In accordance with a preferred embodiment, e is 3 and d is 2.

In accordance with a preferred embodiment, $R^{14}$ is —COOH.

In accordance with a preferred embodiment, e is 3.

In certain embodiments, the $A_3$ adenosine receptor agonist is of the formula (V):

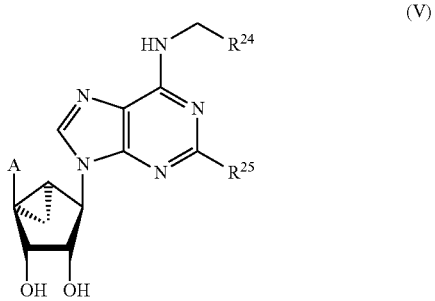

(V)

wherein A is hydrogen or —CONHR$^{26}$, $R^{26}$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, $R^{25}$ is hydrogen, halo, or $C_1$-$C_6$ alkyl, and

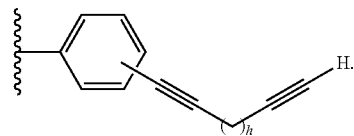

$R^{24}$ is C≡CH, C≡C—(CH$_2$)$_g$—C≡CH, or

In a preferred embodiment, A is —CONHR$^{26}$ and $R^{25}$ is halo.

The definitions of the various terms provided above are applicable to compounds of formulas III and IV also.

In certain embodiments, the $A_3$ adenosine receptor agonist is covalently liked to the dendrimer via a triazole moiety to form the conjugate. An $A_3$ adenosine receptor agonist bearing a terminal acetylene moiety can react with a dendrimer having one or more azido terminal groups to form a 1,2,3-triazole moiety that covalently links the $A_3$ adenosine receptor agonist with the dendrimer.

In certain embodiments, the conjugate includes one or more surface modifying moieties.

In certain preferred embodiments, the surface modifying moiety comprises a hydrophilic group.

In certain more preferred embodiments, the hydrophilic group comprises a polyethylene glycol moiety.

In certain preferred embodiments, the polyethylene glycol moiety is linked to the dendrimer through a bond selected from the group consisting of amide, hydrazide, ether, urethane, urea, thiourea, ester, carbonate, carbamate, hydrazone, carbazone, secondary amine, tertiary amine, and quaternary amine.

In certain embodiments, the conjugate includes one or more fluorescent marker.

In accordance with a preferred embodiment, the one or more fluorescent marker is a dye.

In accordance with a preferred embodiment, the conjugate includes one or more biotinylated moieties.

In accordance with a preferred embodiment, the one or more biotinylated moieties is a polyoxyethylenated biotin-containing moiety.

In certain embodiments, the conjugate includes two or more covalently bonded agonists or antagonists of at least two different G protein-coupled receptors.

In accordance with a preferred embodiment, the conjugate includes at least one agonist of the $A_3$ adenosine receptor.

In certain embodiments, the conjugate includes at least one agonist of the $P2Y_{14}$ receptor.

In certain embodiments, the conjugate includes at least one $P2Y_1$ receptor agonist.

In certain embodiments, the conjugate includes at least one xanthine amine congener. A description of a xanthine amine congener can be found in *Proc. Natl. Acad. Sci. USA* 83, 4089-4093 (June 1986).

Dendrimers are known materials and are classified as polymers. Sajita, J., et al., *Crit. Rev. Ther. Drug Carrier Syst.*, 2007, 24(3): 257-306; Yang, H., et al., *J. Biomater Sci Poly Ed.*, 2006, 17(1-2): 3-19. Dendrimers are made from branched monomers through the iterative organic synthesis by adding one layer (i.e., generation) at each step to provide a perfectly symmetrical structure. The solution conformation of higher generation dendrimers may closely mimic the size and shape of a protein. Furthermore, dendrimers possess favorable characteristics: structural integrity, control of component functional groups—and their physical properties—by chemical synthesis, feasibility to conjugate multiple functional units at the peripheries and interiors, and a low enzymatic degradation rate. Dendrimers possess numerous chain end groups, which can serve as multivalent binding sites for interaction with biological receptors and cell surfaces in the construction of targeted drug delivery systems. Dendritic architecture is characterized by unique properties for drug delivery such as structural uniformity, high purity, efficient membrane transport, high drug payload, targeting potential, and good colloidal, biological, and shelf stability.

The dendrimer can be of any suitable generation, e.g., from 2 to 10 or 2 to 6, or more, including fractional generations, particularly 2 to 8, e.g., 2, 2.5, 3, 3.5, 4, 4.5, 5, 5.5, 6, 6.5, 7, or 7.5. The dendrimer can be anionic or cationic. For example, the half generations are carboxyl terminated and full generations are amine terminated. The conjugate of the invention can include any suitable dendrimer, particularly a poly(amidoamine) (PAMAM) dendrimer. Examples of dendrimers include amine terminated dendrimers, polyester dendrimers, citric acid dendrimers, arginine dendrimers, and carbohydrate dendrimers.

The conjugate of the invention can contain any suitable degree of loading of the agonist or antagonist or both, e.g., a degree of loading greater than about 0.1%, about 10%, about 20%, about 30%, about 40%, about 50%, about 60%, about 70%, about 80%, about 90%, or more; or 100% or less, about 95% or less, about 85% or less, about 75% or less, about 65% or less, about 55% or less, about 45% or less, about 35% or less, about 25% or less, about 15% or less, or about 5% or less, for example, about 1% to about 99%, about 10% to about 90%, about 20% to about 80%, about 30% to about 70%, or about 40% to about 60%, of the theoretical capacity of the dendrimer.

The conjugates of the invention can optionally include one or more surface modifying moieties to modify one or more of the surface properties of the conjugate or a group that protects the surface functional groups such as amine or carboxylic functional groups. Thus, for example, the surface modifying moiety can be an amine protecting group. An example of an amine protecting group is $C_1$-$C_6$ alkyl carbonyl, preferably $C_1$-$C_3$ alkyl carbonyl, wherein the alkyl group is unsubstituted or substituted with a substituent selected from the group consisting of $C_1$-$C_6$ alkoxy, hydroxy, halo, nitro, cyano, amino, amido, and mercapto.

In accordance with an embodiment, the surface modifying moiety comprises a hydrophilic group, e.g., a polyethylene glycol moiety. The polyethylene glycol moiety can be linked to the dendrimer through any suitable bond, e.g., amide, hydrazide, ether, urethane, urea, thiourea, ester, carbonate, carbamate, hydrazone, carbazone, secondary amine, tertiary amine, and quaternary amine. The amine or carboxyl ends of a dendrimer could also be covalently linked to amino acids, peptides, nucleic acids, glycosides, and one or more small molecules. For PEG conjugates of drugs and methods of preparing such conjugates, see Poly(ethylene glycol) Conjugated Drugs and Prodrugs: A Comprehensive Review; Greenwald, R. B., et al., *Critical Reviews in Therapeutic Drug Carrier Systems*, 17(2):101-161 (2000).

In accordance with an embodiment, the conjugate includes one or more fluorescent marker. In accordance with a preferred embodiment, the fluorescent marker is a dye. The dye can be any suitable dye, many of which are well know to those of ordinary skill in the art.

In accordance with an embodiment, the conjugate includes one or more biotinylated moieties. In accordance with a preferred embodiment, the one or more biotinylated moieties is a polyoxyethylanted biotin-containing moiety.

In accordance with an embodiment, the conjugate includes two or more covalently bonded agonists or antagonists of at least two different G protein-coupled receptors. In accordance with a preferred embodiment, the conjugate includes at least one agonist of the $A_3$ adenosine receptor. In certain other embodiments, the conjugate includes at least one covalently bonded agonists or antagonists selected from the group consisting of an agonist of the $P2Y_{14}$ receptor, a $P2Y_1$ receptor antagonist, and a xanthine amine congener.

In accordance with an embodiment, the conjugate comprises a moiety of the formula (I″):

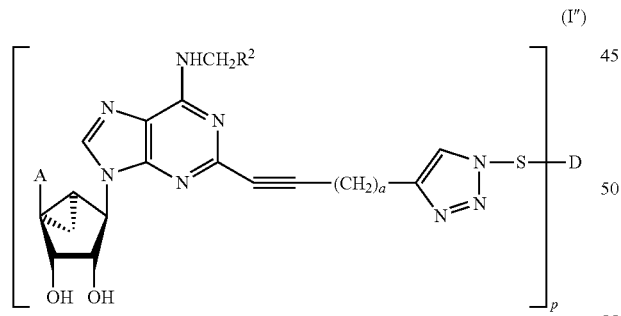

wherein A is hydrogen or —CONHR$^1$,

R$^1$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, R$^2$ is a phenyl group optionally substituted with one or more halogen atoms, S is a bond or a linking moiety, p is 1 to 200, and D comprises a dendrimer moiety.

In accordance with an embodiment, the conjugate comprises a moiety of the formula (II″):

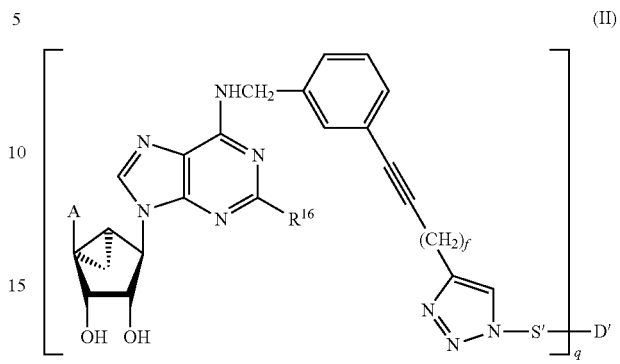

wherein A is hydrogen or —CONHR$^{15}$,

R$^{15}$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, S' is a bond or a linking moiety, q is 1 to 200, and D' comprises a dendrimer moiety.

In accordance with an embodiment, the conjugate comprises a moiety of the formula (V″):

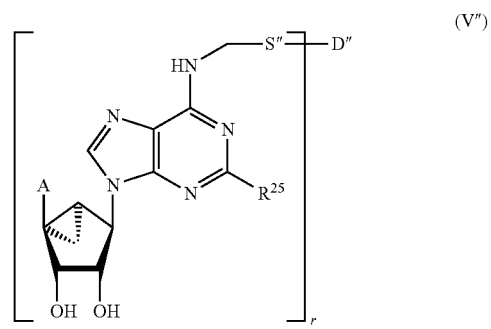

wherein A is hydrogen or —CONHR$^{26}$,

R$^{26}$ is selected from the group consisting of hydrogen, $C_1$-$C_6$ alkyl, $C_2$-$C_6$ alkenyl, $C_2$-$C_6$ alkynyl, $C_3$-$C_8$ cycloalkyl, and $C_6$-$C_{10}$ aryl, S″ is a bond or a linking moiety, r is 1 to 200, R$^{25}$ is hydrogen, halo, or $C_1$-$C_6$ alkyl, and D″ comprises a dendrimer moiety.

S, S' and S″ can comprise a bond or any suitable linking moiety. D, D', and D″ can comprise any suitable dendrimer moiety or derivative thereof. Typically, p, q, and r are 1 to 200 and can be integers or fractions. In a preferred embodiment, p, q, and r are 1 to 100, e.g., 1 to 80, or 1 to 64, or 50 to 100, or 50 to 64, or 25-100, or 50-100.

The invention further provides a pharmaceutical composition comprising a conjugate as described herein, and a pharmaceutically acceptable carrier. The pharmaceutically acceptable carrier can be any suitable pharmaceutically acceptable carrier as described herein.

The invention also provides a method of treating a disease which is treatable by agonizing or antagonizing a receptor of the GPCR superfamily in a mammal comprising administering to the mammal an effective amount of a conjugate. In certain embodiments, the disease is treatable by an $A_3$ adenosine receptor antagonist. In some embodiments, the method involves reducing intraocular pressure or inhibiting tumor growth.

In certain embodiments, the invention also provides a method of treating a disease, wherein the disease is treatable by a $P2Y_1$ receptor antagonist. In some embodiments, the method involves treating or preventing thrombosis.

The invention also provides a method of preparing a dendrimer conjugate comprising a $A_3AR$ receptor antagonist and a dendrimer that is covalently linked to the $A_3AR$ receptor antagonist through a triazole moiety, comprising: (a) providing a dendrimer having one or more azido terminal groups; (b) reacting the dendrimer of (a) with a $A_3AR$ receptor agonist having a terminal acetylenic group in the presence of a copper (I) catalyst; and (c) obtaining the dendrimer conjugate that is covalently linked to the $A_3AR$ receptor agonist through a triazole moiety. In some embodiments, the dendrimer conjugate further comprises an $P2Y_{14}$ receptor agonist covalently linked to the dendrimer and said method comprises (b) reacting the dendrimer of (a), in any order, with a $P2Y_{14}$ receptor agonist having a terminal acetylenic group and an $A_3$ adenosine receptor agonist, or a mixture thereof, in the presence of a copper (I) catalyst. In certain preferred embodiments, the copper (I) catalyst comprises $CuSO_4$ and sodium ascorbate.

The invention also provides a diagnostic method for determining a treatment of a patient for a possible agonist or antagonist of the GPCR superfamily or receptors, the treatment comprising: (a) administering a conjugate comprising a dendrimer, at least one ligand covalently linked to the dendrimer, a fluorescent marker covalently linked to the dendrimer, and optionally one or more surface modifying moieties covalently linked to the dendrimer, wherein the ligand is a functionalized congener of an agonist or antagonist of a receptor of the G-protein coupled receptor (GPCR) superfamily; (b) obtaining a biological sample from the patient; (c) determining the level of expression of at least one receptor; (d) comparing the level of expression of the receptor to that of a normal population; and (e) if the patient's level of expression is higher than that of the normal population, determining a treatment regimen comprising administering an agonist or antagonist of the receptor whose expression was higher in the patient than that of the normal population. In certain embodiments, the receptor is an $A_3$ adenosine receptor or a $P2Y_{14}$ receptor.

It is contemplated that the compounds of the present invention are useful in the treatment or prevention of various airway diseases (through $A_{2B}$, $A_3$, $P2Y_2$ receptors), cancer (through $A_3$, P2 receptors), cardiac arrhythmias (through $A_1$ receptors), cardiac ischemia (through $A_1$, $A_3$ receptors), epilepsy (through $A_1$, P2X receptors), Huntington's Disease (through $A_{2A}$ receptors), immunodeficient disorders (through $A_2$, $A_3$ receptors), inflammatory disorders (through $A_3$, P2 receptors), neonatal hypoxia (through $A_1$ receptors), neurodegenerative (through $A_1$, $A_3$, P2 receptors), pain (through $A_1$, $A_3$, P2X3 receptors), Parkinson's Disease (through $A_{2A}$ receptors), renal failure (through $A_1$ receptors), schizophrenia (through $A_{2A}$ receptors), sleep disorders (through $A_1$ receptors), stroke (through $A_1$, $A_3$, P2 receptors), thrombosis (through $P2Y_1$, $P2Y_{AC}$ receptors), urinary incontinence (through $P2X_1$ receptors), diabetes (through $A_1$ receptors), psoriasis (through P2X receptors), septic shock (through P2 receptors), brain trauma (through $A_1$ receptors), glaucoma (through $A_3$ receptors) and congestive heart failure (through P2 receptors).

Chemical Synthesis

Figure 8:
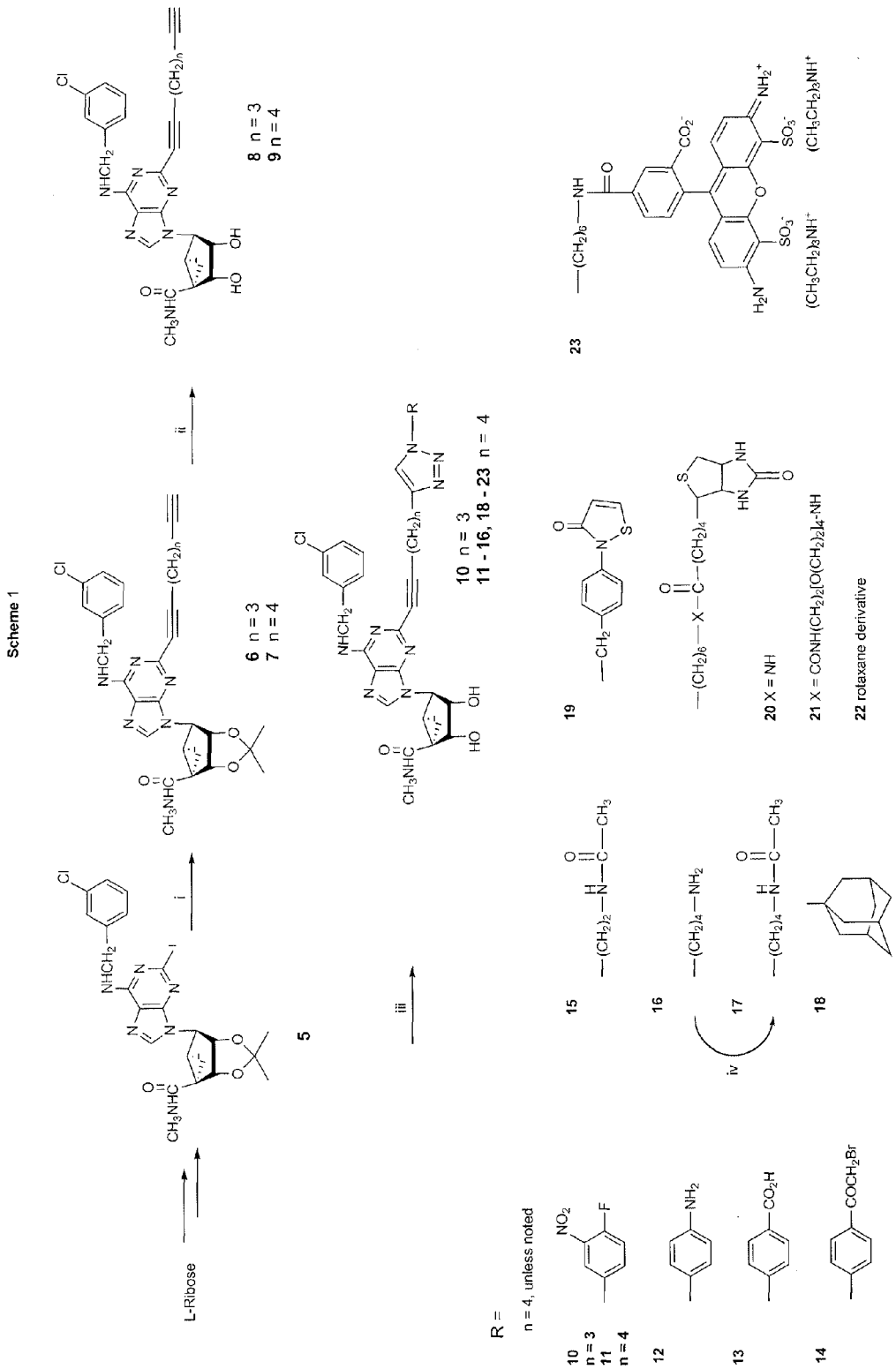
FIG. 8 illustrates a synthetic scheme to prepare compounds 10-23 in accordance with an embodiment of the invention.
Figure 9:
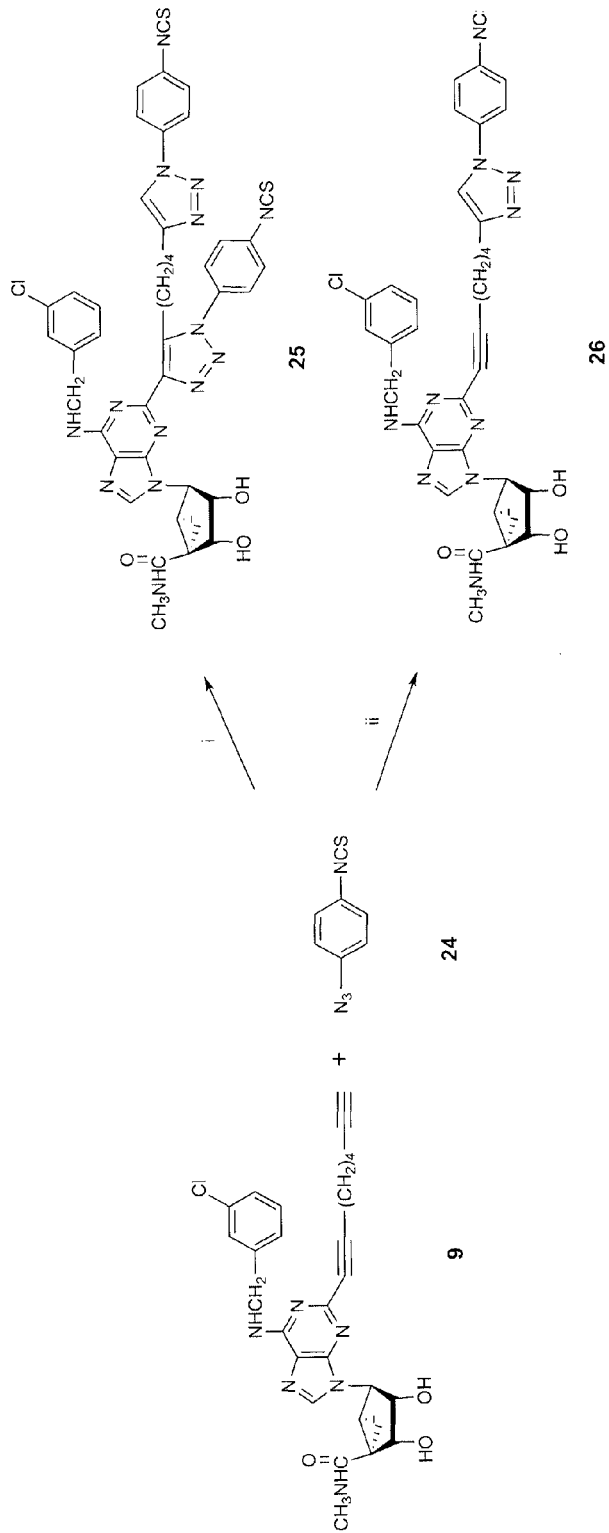
FIG. 9 illustrates a synthetic scheme to prepare compounds 25 and 26 in accordance with an embodiment of the invention.

The synthetic route to the small molecular 5'-N-methyluronamide (N)-methanocarba 2-alkynyl triazole-containing derivatives 10-23 is shown in FIG. 8. The synthesis of the 2',3'-protected dialkynyl intermediates 6 and 7 was performed using a Sonogashira coupling on the corresponding 2-iodo intermediate 5. After deprotection of the 2',3'-hydroxyl groups to provide nucleosides 8 and 9, compounds 10-23 were obtained using the Cu(I)-catalyzed 2+3 cyclization reaction of the terminal acetylene group with an appropriate azide. The reactions were generally selective for the terminal alkyne, but reaction with 4-isothiocyanatophenylazide 24 initially produced the disubstituted product 25 as the major product isolated (FIG. 9). Use of the Cu(I)-stabilizing catalyst tris[(1-benzyl-1H-1,2,3-triazol-4-yl)methyl]amine (TBTA) in this reaction provided the desired monosubstituted analogue 26.

The fluorescent rotaxane derivative 22 was prepared from a commercial reactive azide (SRfluor™ 680 Azide, Molecular Targeting Technologies, Inc. (West Chester, Pa.)), of undisclosed structure, which fluoresces strongly at 680 nm. Such rotaxane derivatives have the following advantages over other small fluorophores: improved chemical and photochemical stability, sharp absorption and emission bands, and stability over the pH range from 2-12. They are typically much brighter in fluorescence than the Alexa dyes. The elemental composition of this proprietary dye moiety, but not the full chemical structure, was revealed by the supplier, and the integrity of the synthetic product 22 was demonstrated by high resolution mass spectroscopy. The expected molecular weight of the click product of the 1:1 reaction with dialkyne 9 was obtained.

Figure 10:
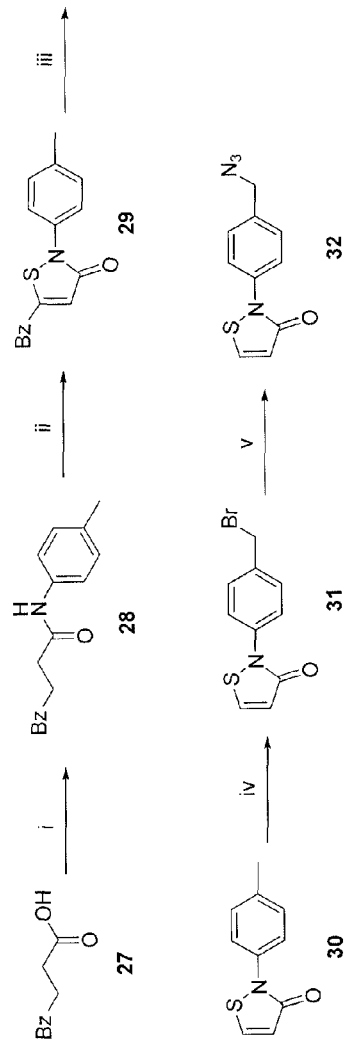
FIG. 10 illustrates a synthetic scheme to prepare a synthetic intermediate 32 in accordance with an embodiment of the invention.
Figure 11:
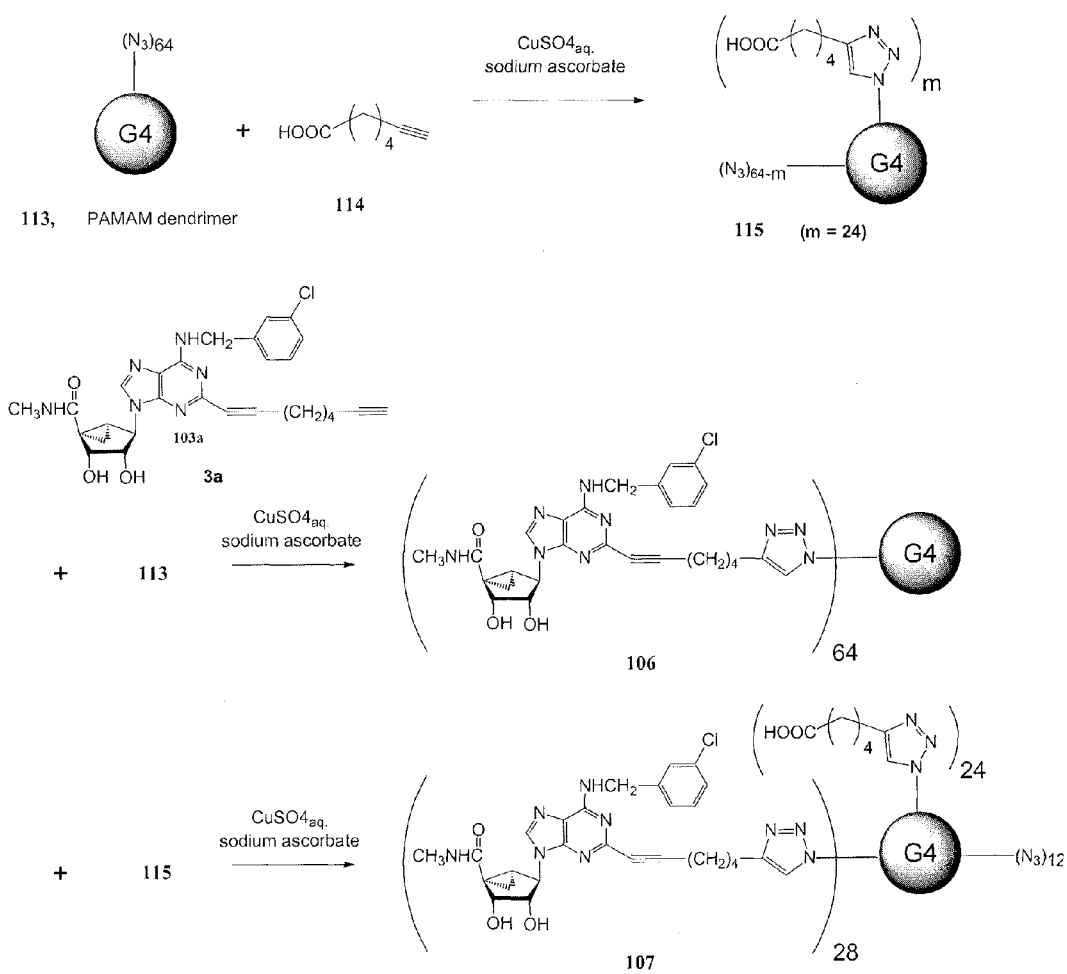
FIG. 11 illustrates the derivatives 106 and 107, containing a functionalized 2-alkynyl $A_3AR$ agonist. An optional water-solubilizing group was added to 107, in the form of an aliphatic carboxylic acid.
Figure 12:
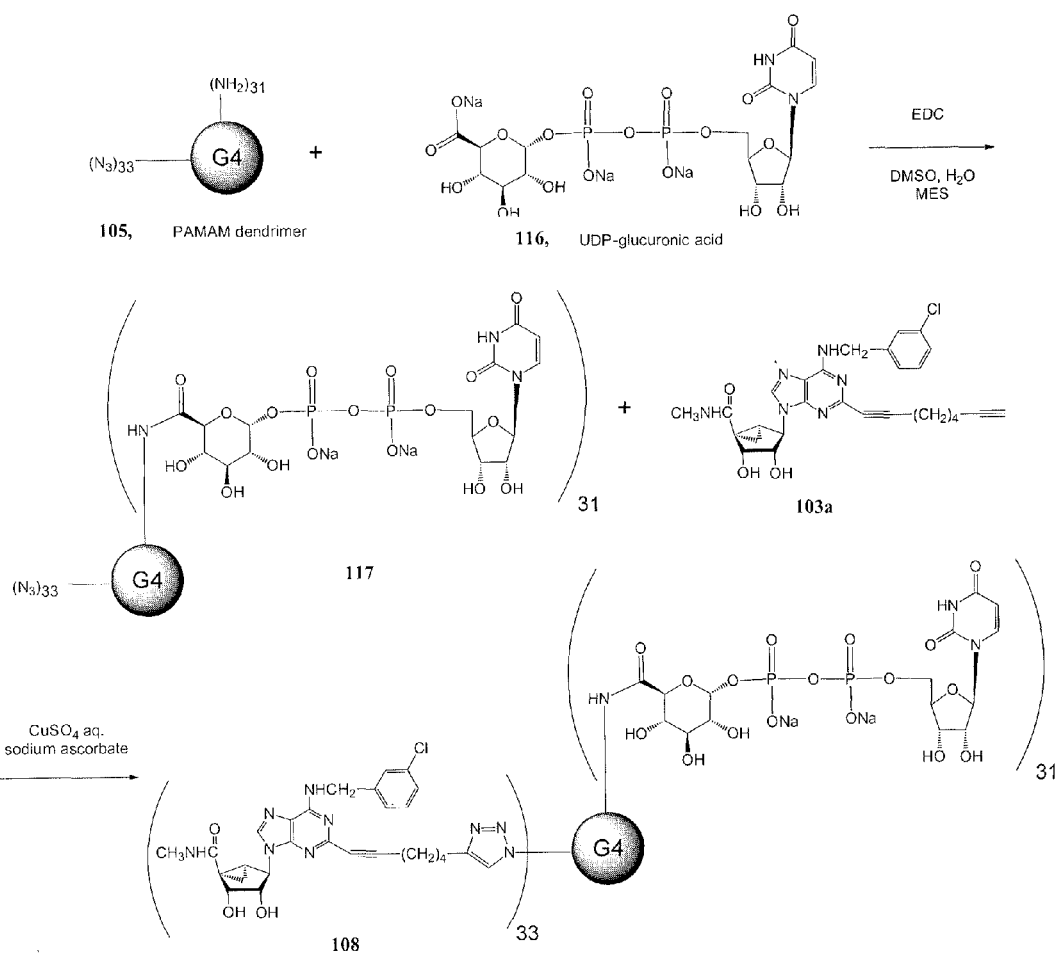
FIG. 12 illustrates synthesis of two PAMAM dendrimer containing a functionalized agonist of the $P2Y_{14}$ receptor derived by amide linkage of UDPGA 116. Conjugate 117 contains only the $P2Y_{14}$ receptor agonist; conjugate 108 contains an $A_3AR$ agonist linked through a click reaction of its 2-alkynyl functionalized chain. The dendrimer precursor 105 contained a random distribution of peripheral amino and azido groups in a ratio of ~33:31.
Figure 13:
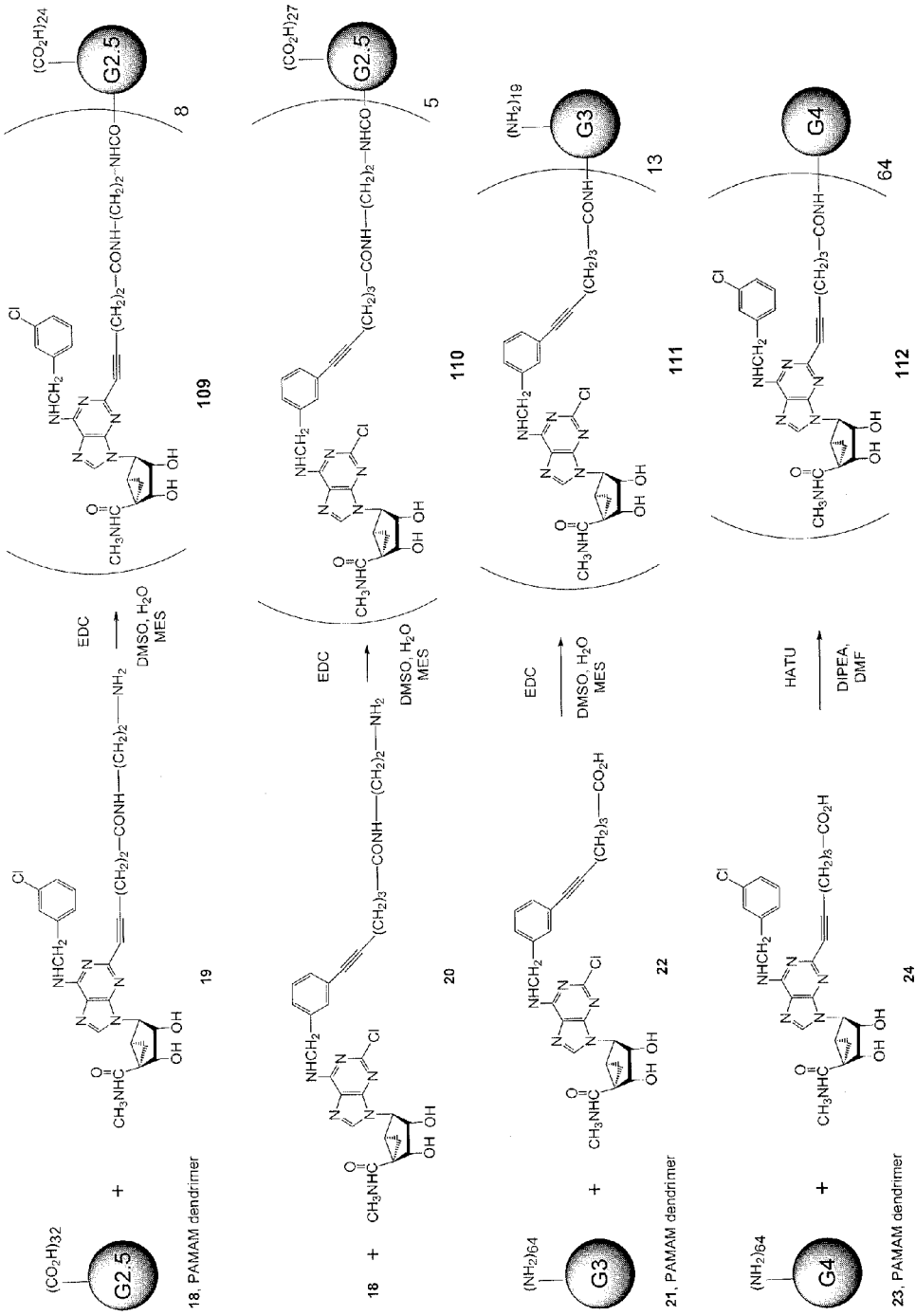
FIG. 13 illustrates a synthetic scheme to prepare dendrimer conjugates 109-112 in accordance with an embodiment of the invention.
Figure 14:
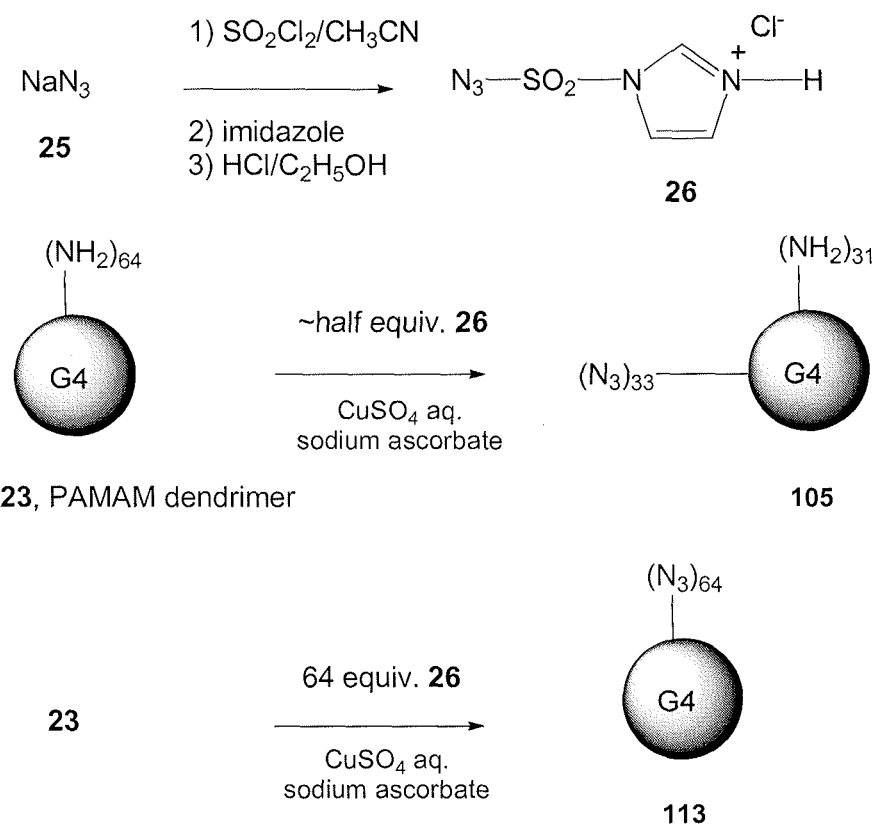
FIG. 14 illustrates a synthetic scheme to prepare reactive dendrimer 113 in accordance with an embodiment of the invention.
Figure 15A:
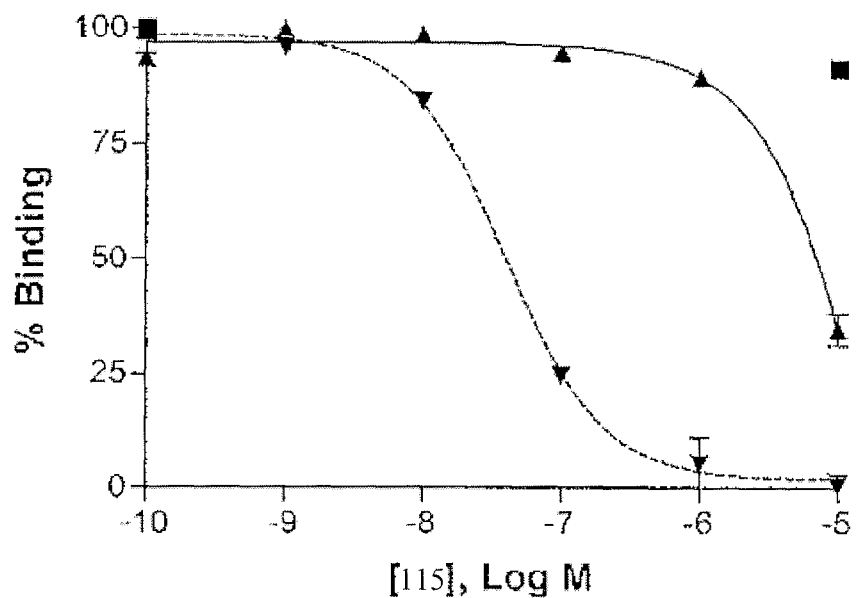
FIGS. 15 A-B illustrate the inhibition of radioligand binding by (N)-methanocarba nucleoside analogues in membranes of CHO cells expressing the human $A_1$ (0.1) and $A_{2A}$ (σ) and $A_3$ (∇) ARs. Inhibition curves are shown for the agonist analogues containing a triazole group, the adamantyl derivative 18, shown in FIG. 8, and the amide model compound for click linkage to carriers 115, shown in FIG. 11. Both of the analogues shown were highly selective for the $hA_3AR$ in comparison to the $A_1$ and $A_{2A}$ ARs.
Figure 15B:
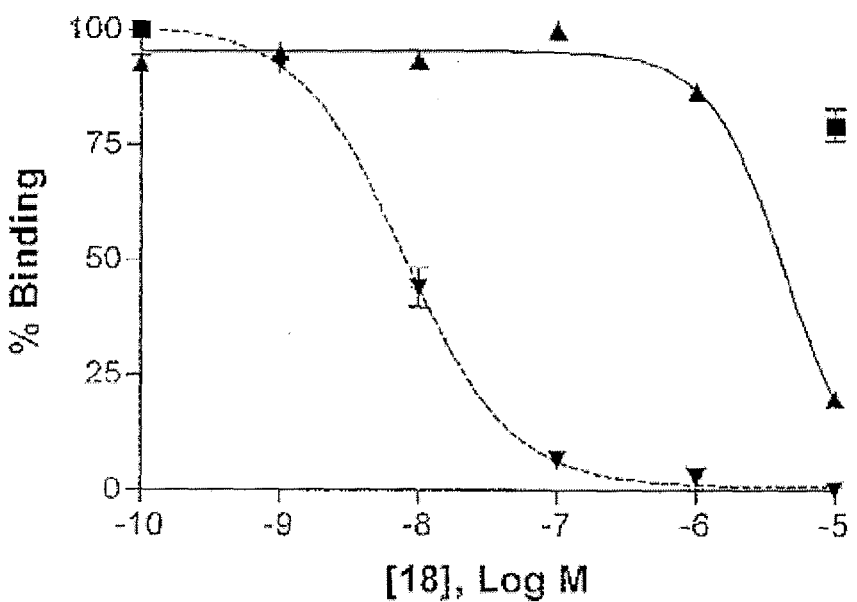
Figure 16:
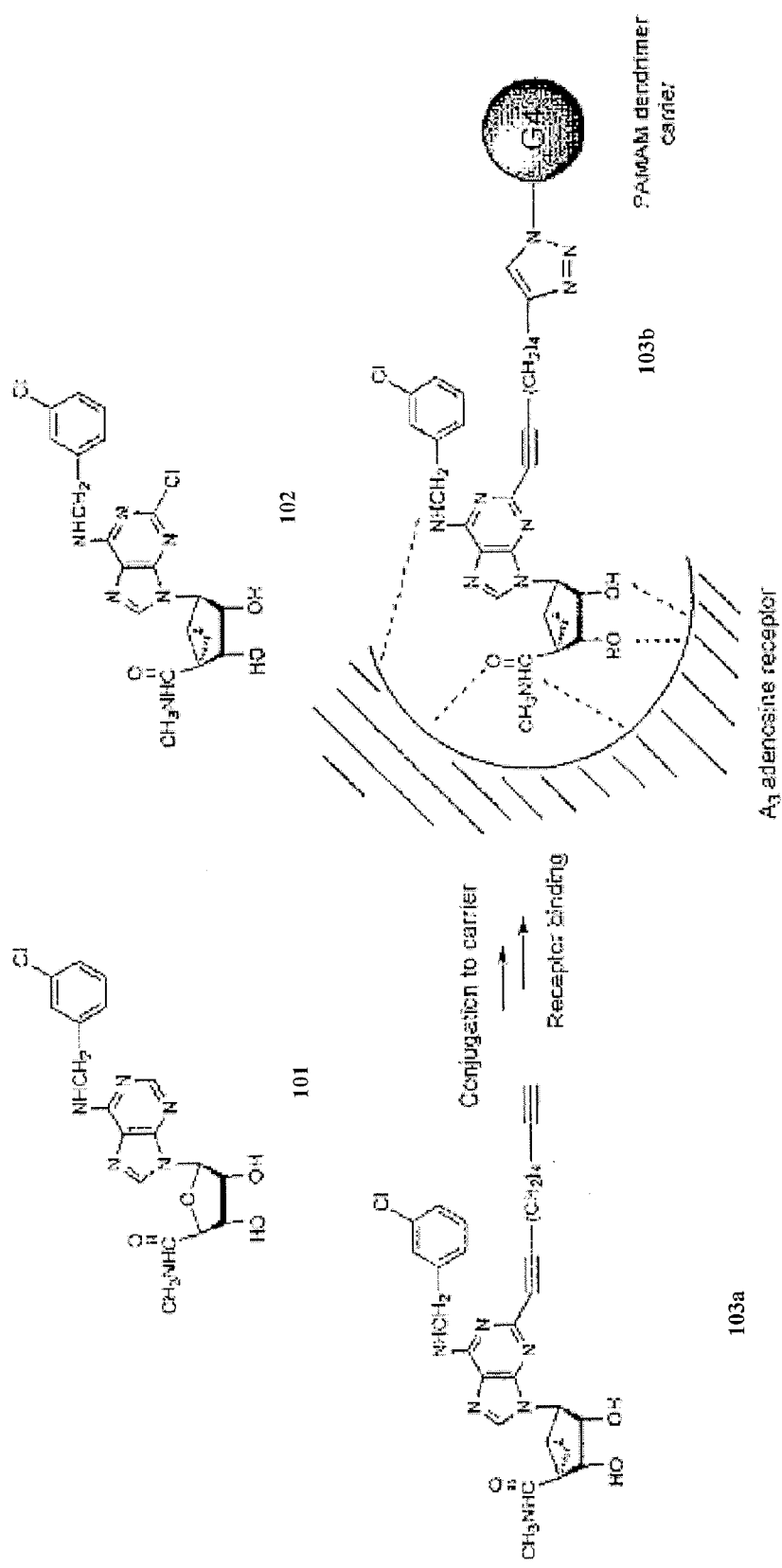
FIG. 16 illustrates structures of adenosine $A_3AR$ agonist monomers (101-103a,b) and the design of multivalent dendrimer conjugates in the (N)-methanocarba series in accordance with an embodiment of the invention.
Figure 17A:
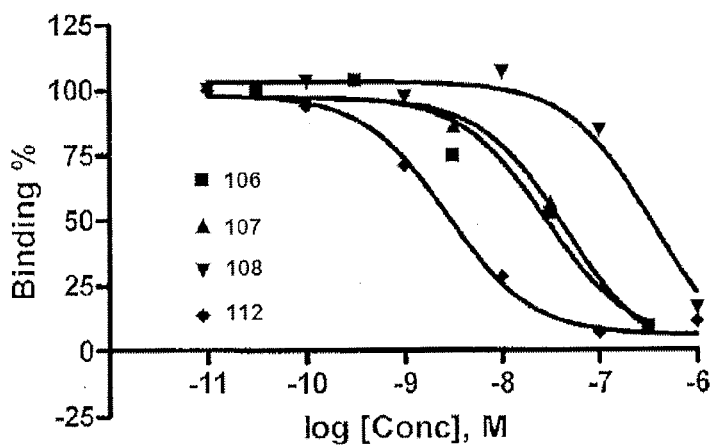
FIGS. 17 A-C illustrate the inhibition of radioligand binding by dendrimer nucleoside conjugates in membranes of CHO cells expressing the human $A_1$ (A) and $A_3$ (C) ARs and HEK-293 cells expressing the human $A_{2A}AR$ (B). Inhibition curves at three ARs are shown for the dendrimer-nucleoside conjugates 106 and 107, in which the linkage to an azide-derivatized dendrimer was formed by click cycloaddition, for the mixed nucleoside/nucleotide conjugate 108 and for the amide-linked nucleoside conjugate 112. Both 106 and 107 were highly selective for the $hA_3AR$ in comparison to the $hA_1$ and $hA_{2A}ARs$.
Figure 17B:
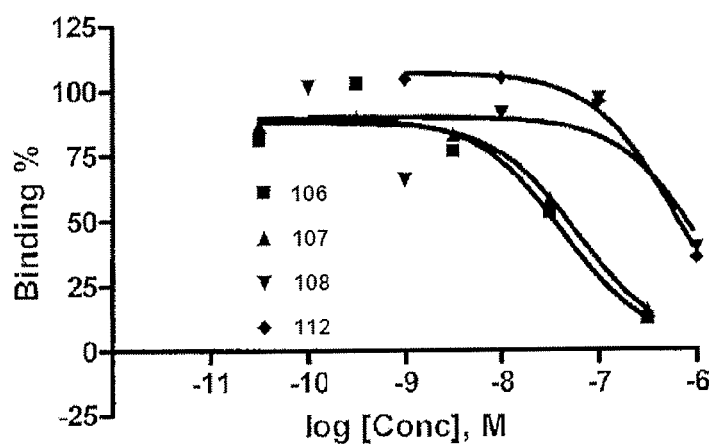
Figure 17C:
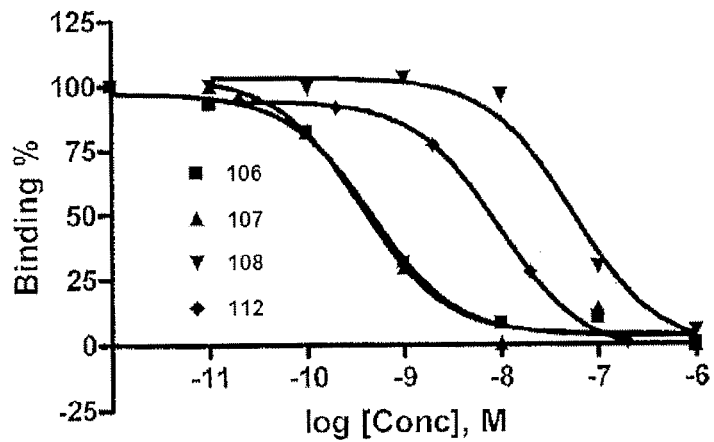
Figure 18:
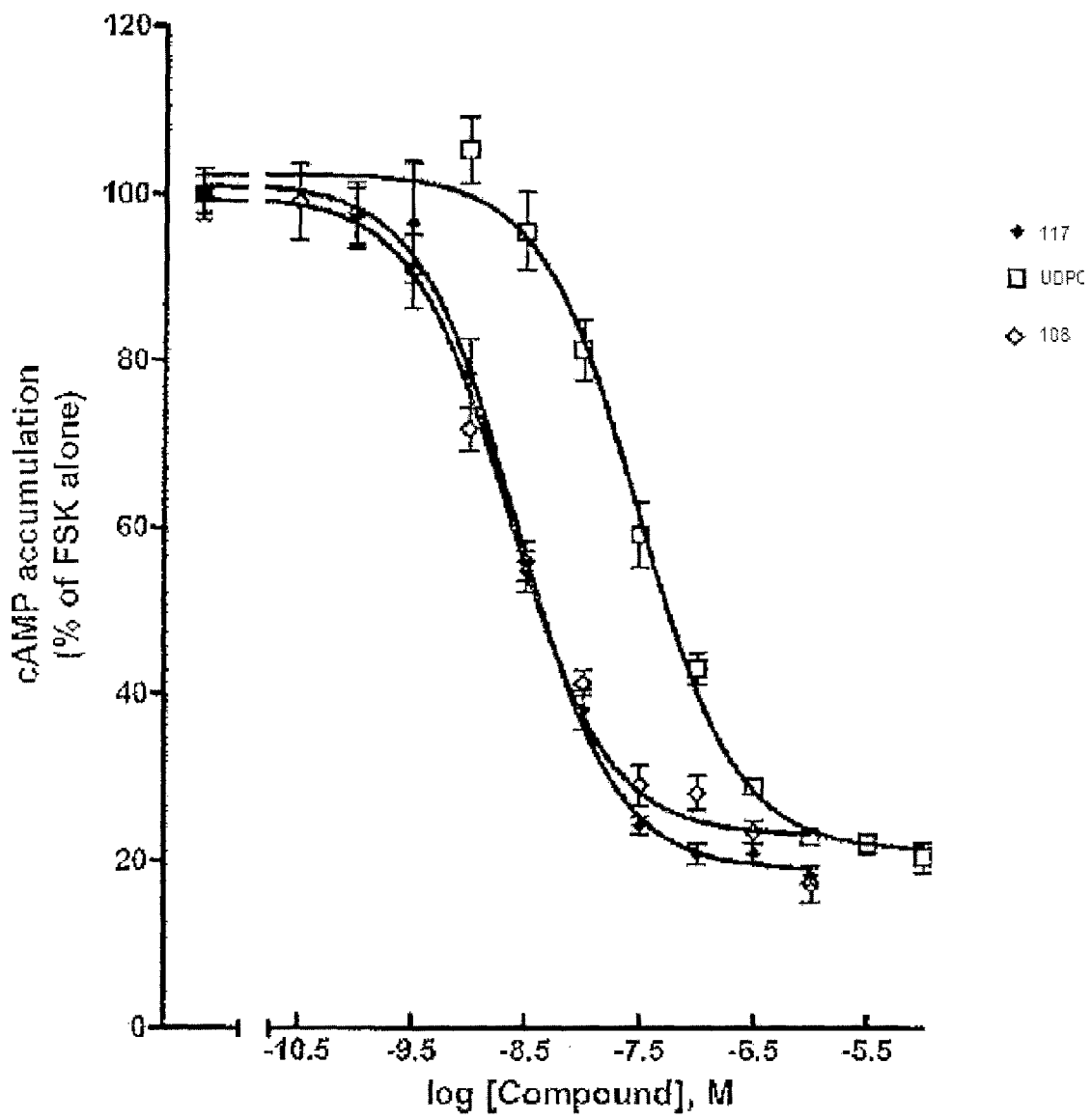
FIG. 18 illustrates activation of the $G_i$-coupled $P2Y_{14}$ receptor stably expressed in C6 cells by the mixed nucleoside/nucleotide G4 dendrimer conjugate 108 (MRS5259) and the nucleotide G4 dendrimer conjugate 117 (MRS2949). Inhibition of forskolin-stimulated cAMP is shown in comparison to the effects of UDPG (n=3).
Figure 19:
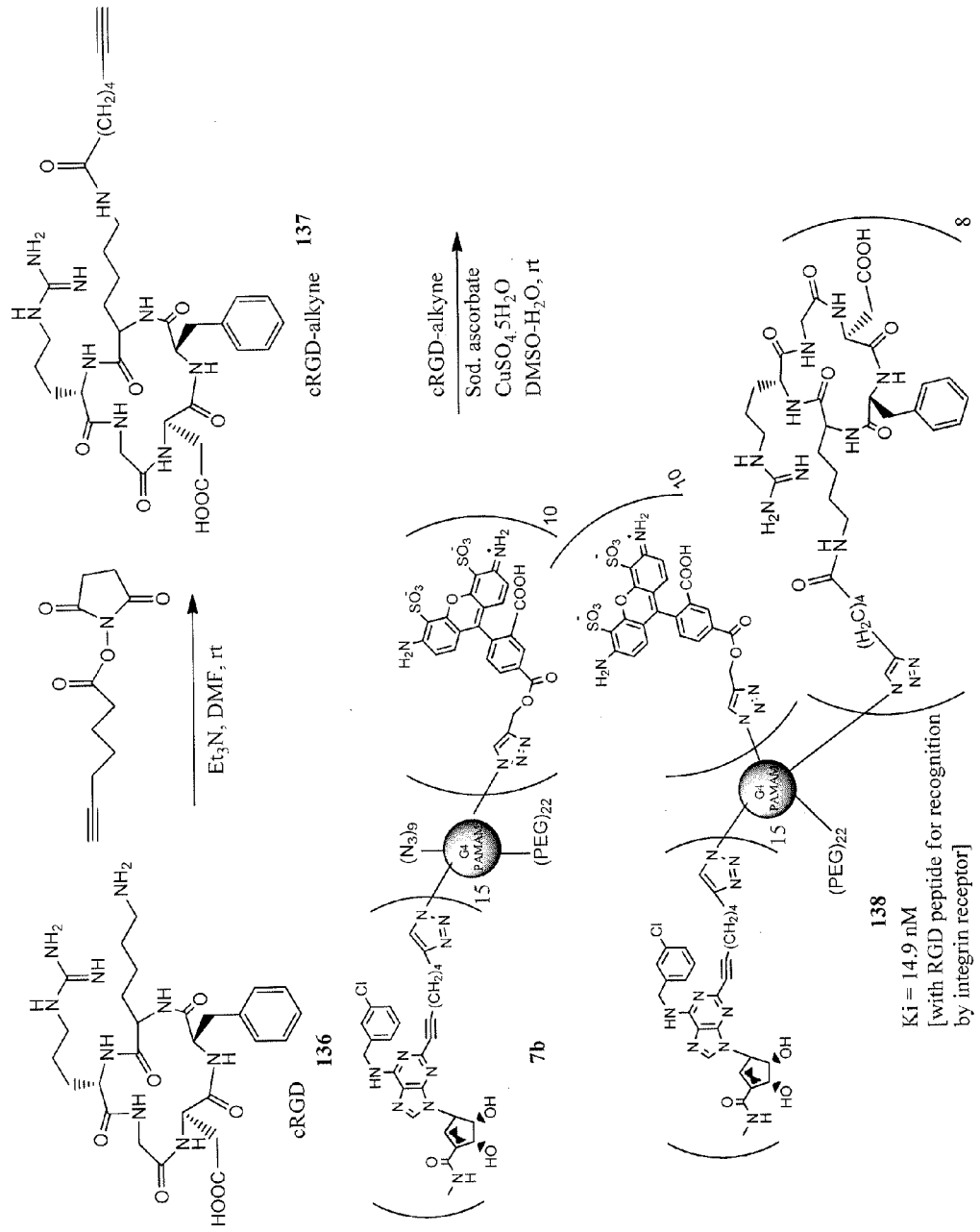
FIG. 19 illustrates a synthetic scheme to prepare dendrimer conjugate 138 in accordance with an embodiment of the invention.
Figure 20:
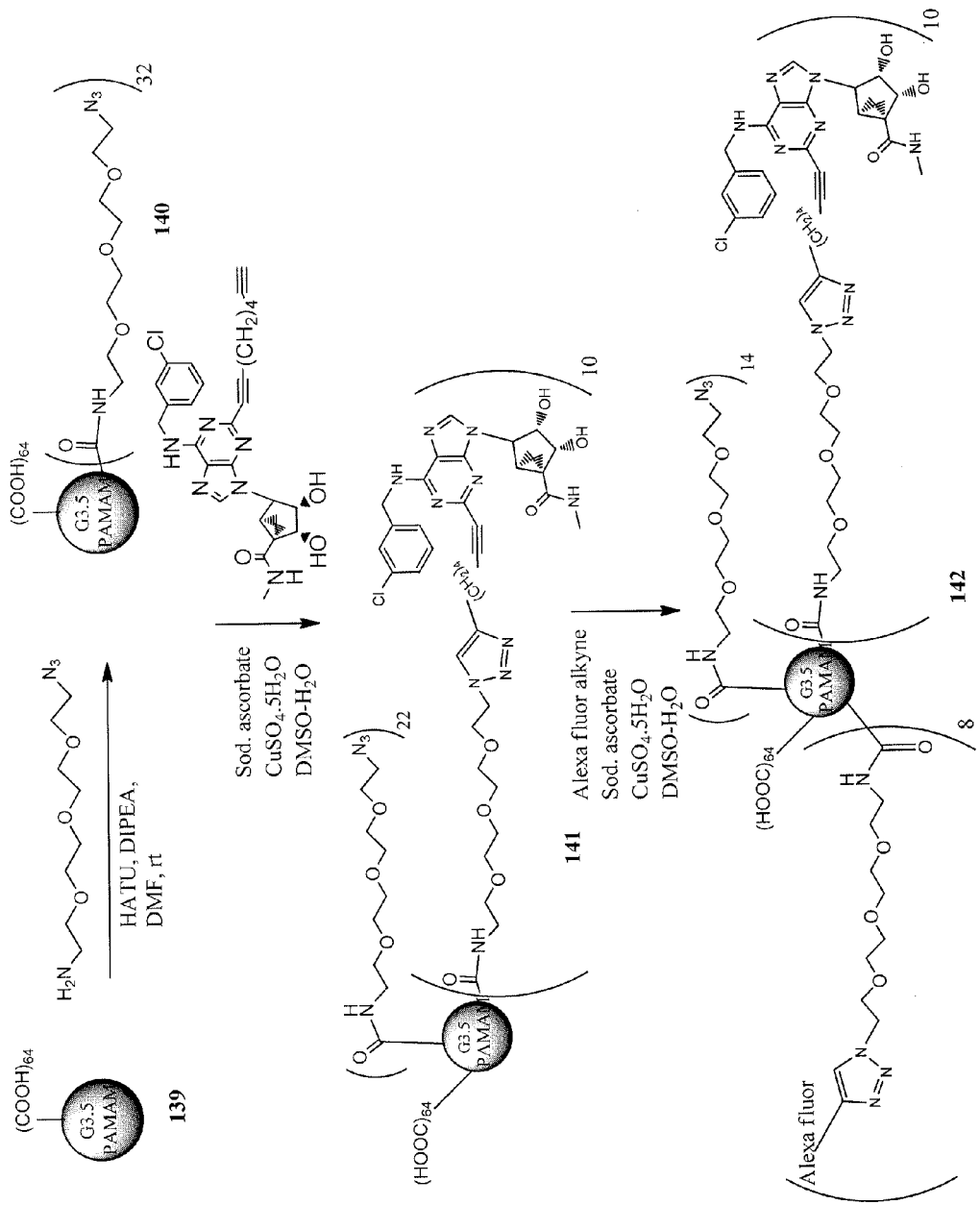
FIG. 20 illustrates a synthetic scheme to prepare dendrimer conjugate 142 in accordance with an embodiment of the invention.
Figure 21:
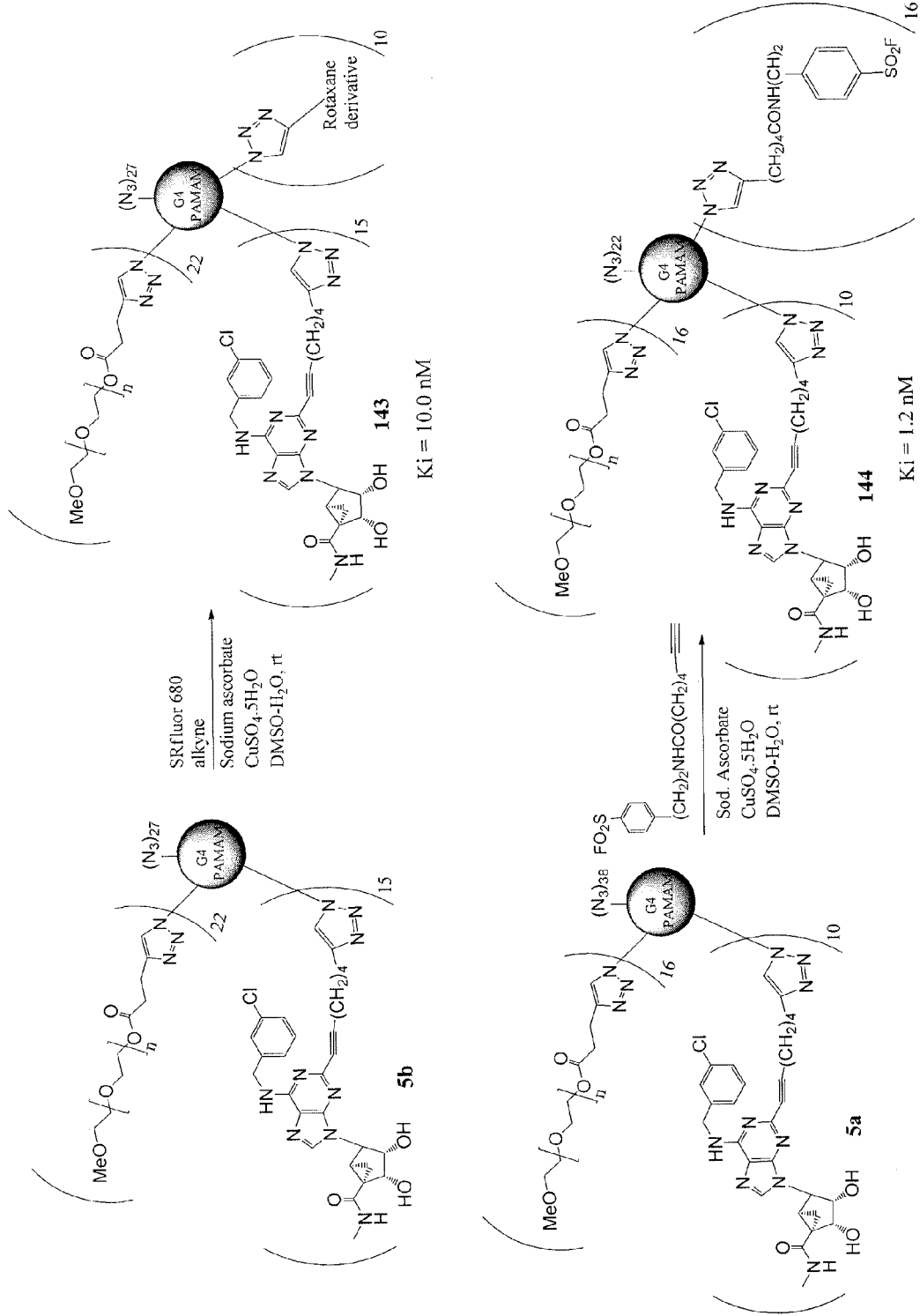
FIG. 21 illustrates a synthetic scheme to prepare dendrimer conjugate 144 in accordance with an embodiment of the invention.
Figure 22:
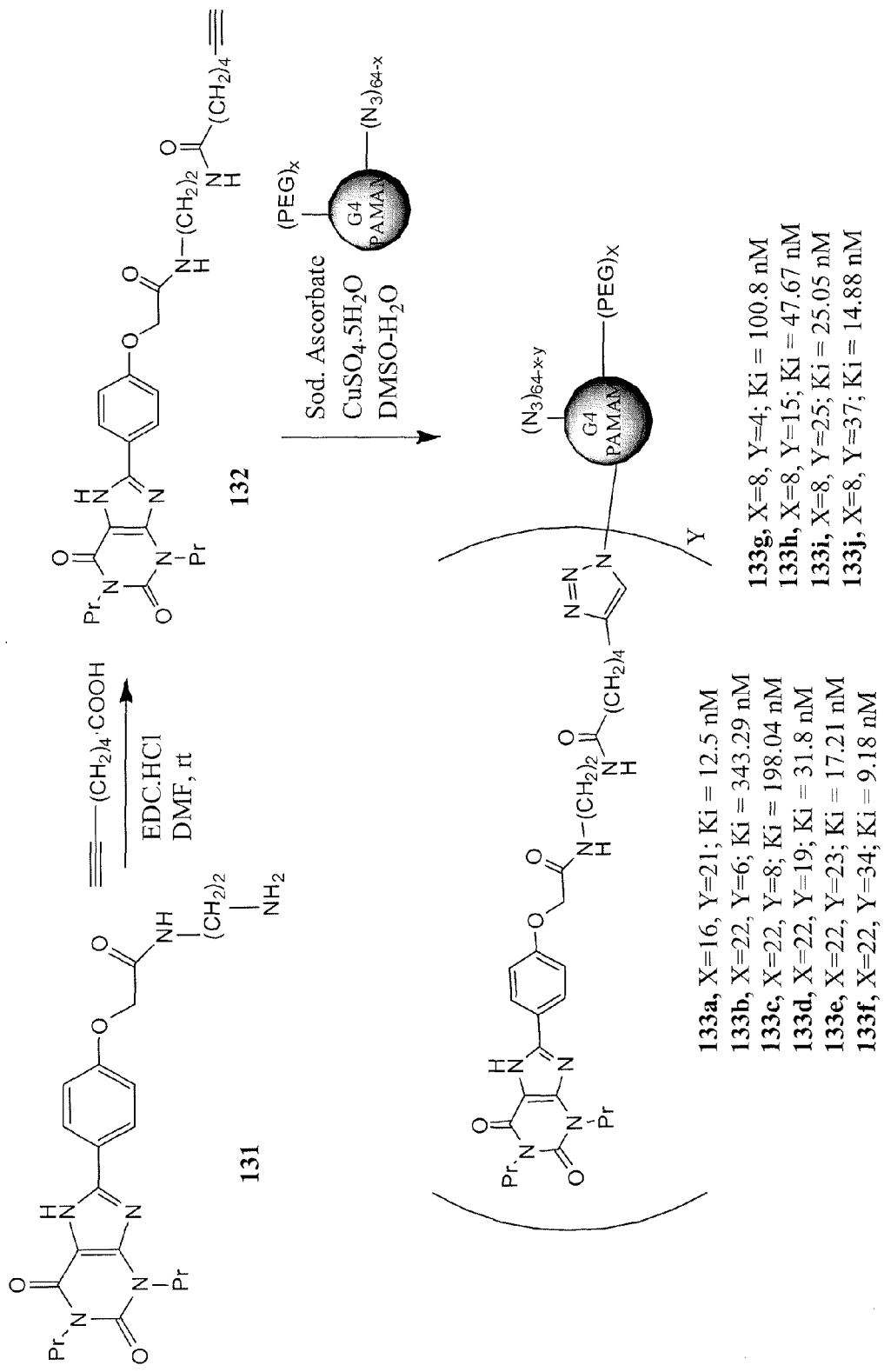
FIG. 22 illustrates a synthetic scheme to prepare dendrimer conjugates 133a-133j in accordance with an embodiment of the invention.
Figure 23:
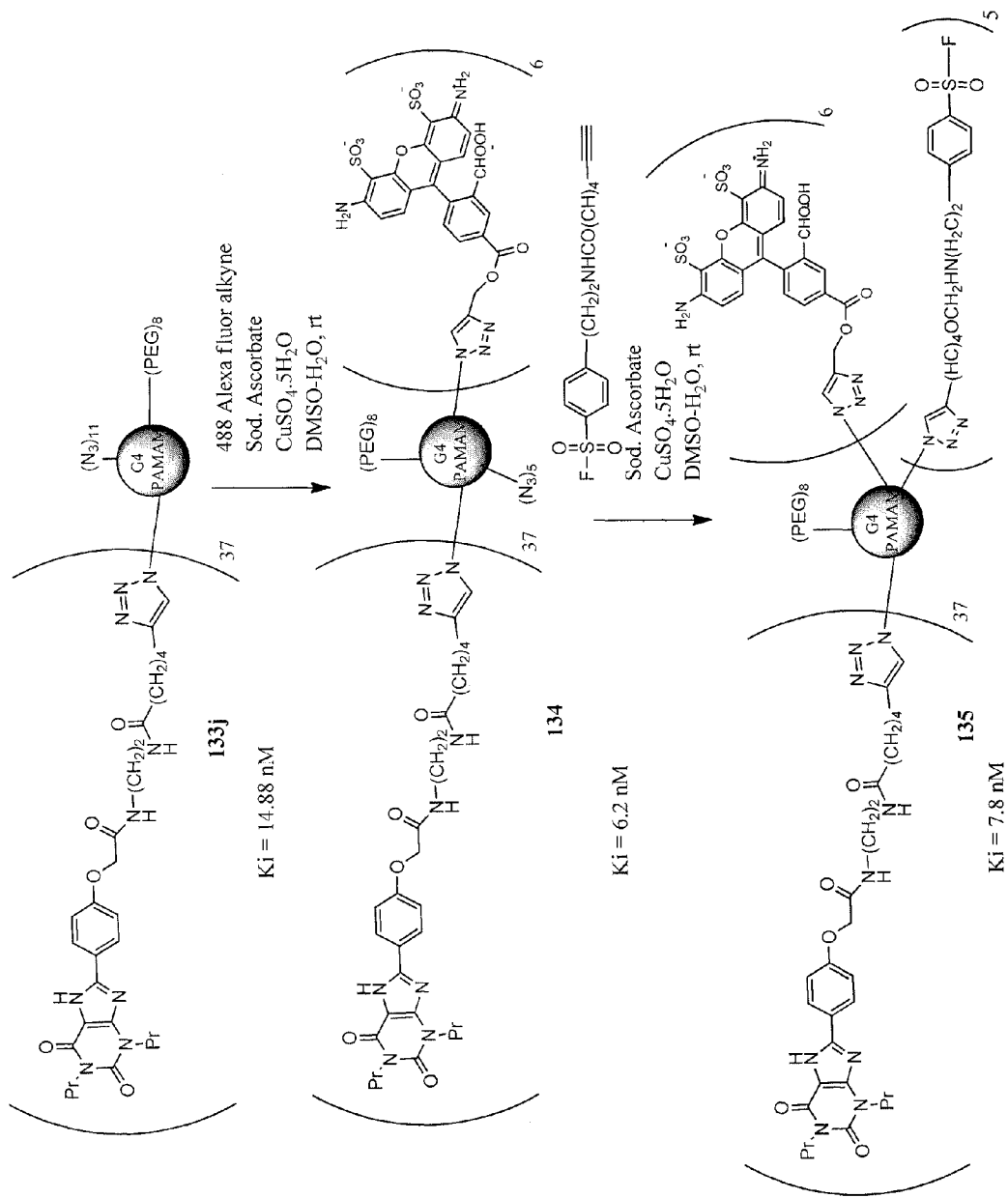
FIG. 23 illustrates a synthetic scheme to prepare dendrimer conjugate 135 in accordance with an embodiment of the invention.
Figure 24:
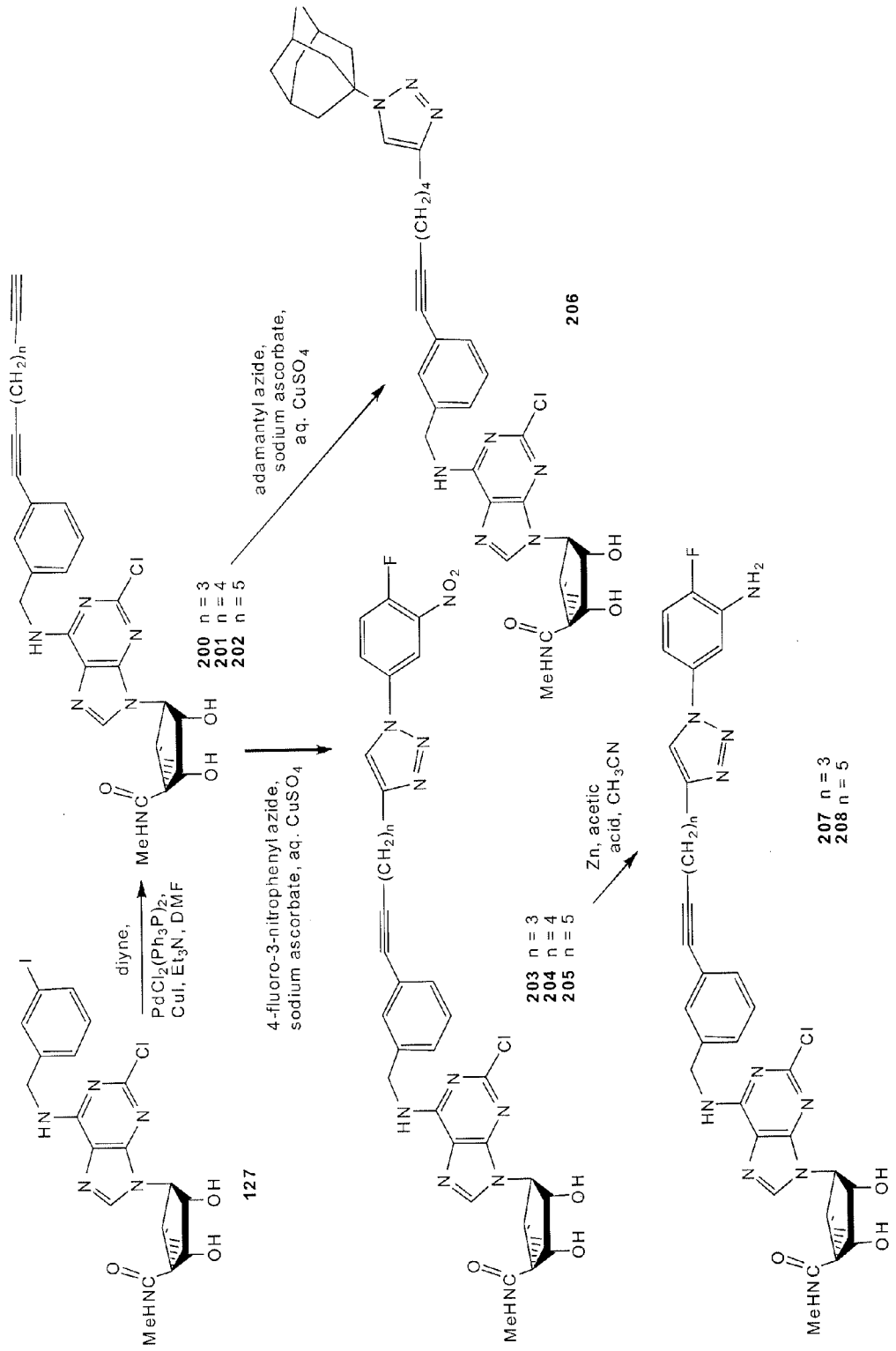
FIG. 24 illustrates a synthetic scheme to prepare $N^6$-benzyl compounds 200-208 in accordance with an embodiment of the invention.
Figure 25:
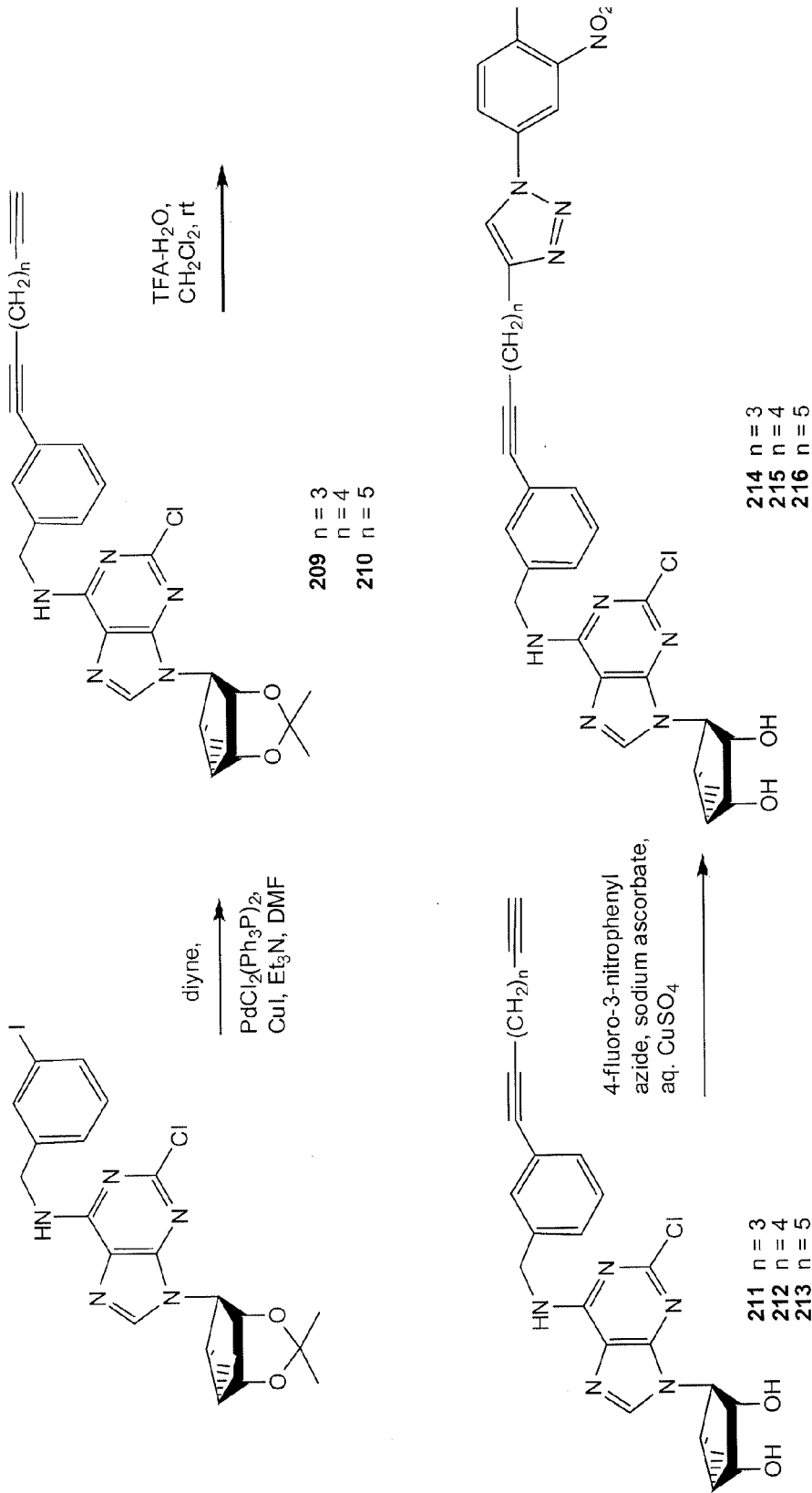
FIG. 25 illustrates a synthetic scheme to prepare $N^6$-benzyl compounds 209-216 in accordance with an embodiment of the invention.
Figure 26:
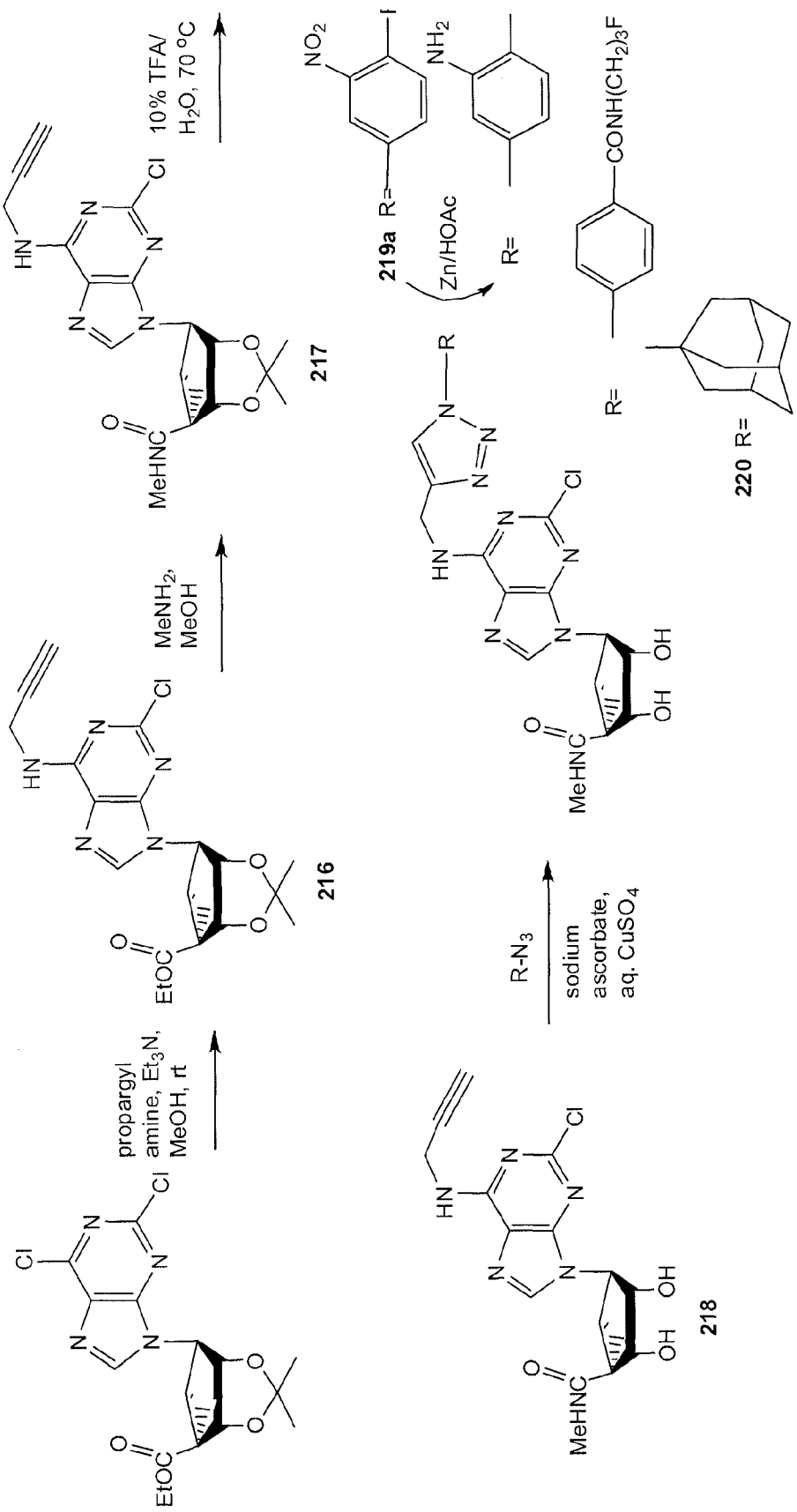
FIG. 26 illustrates a synthetic scheme to prepare $N^6$-propargyl compounds and $N^6$-triazolinyl compounds in accordance with an embodiment of the invention.
Figure 27:
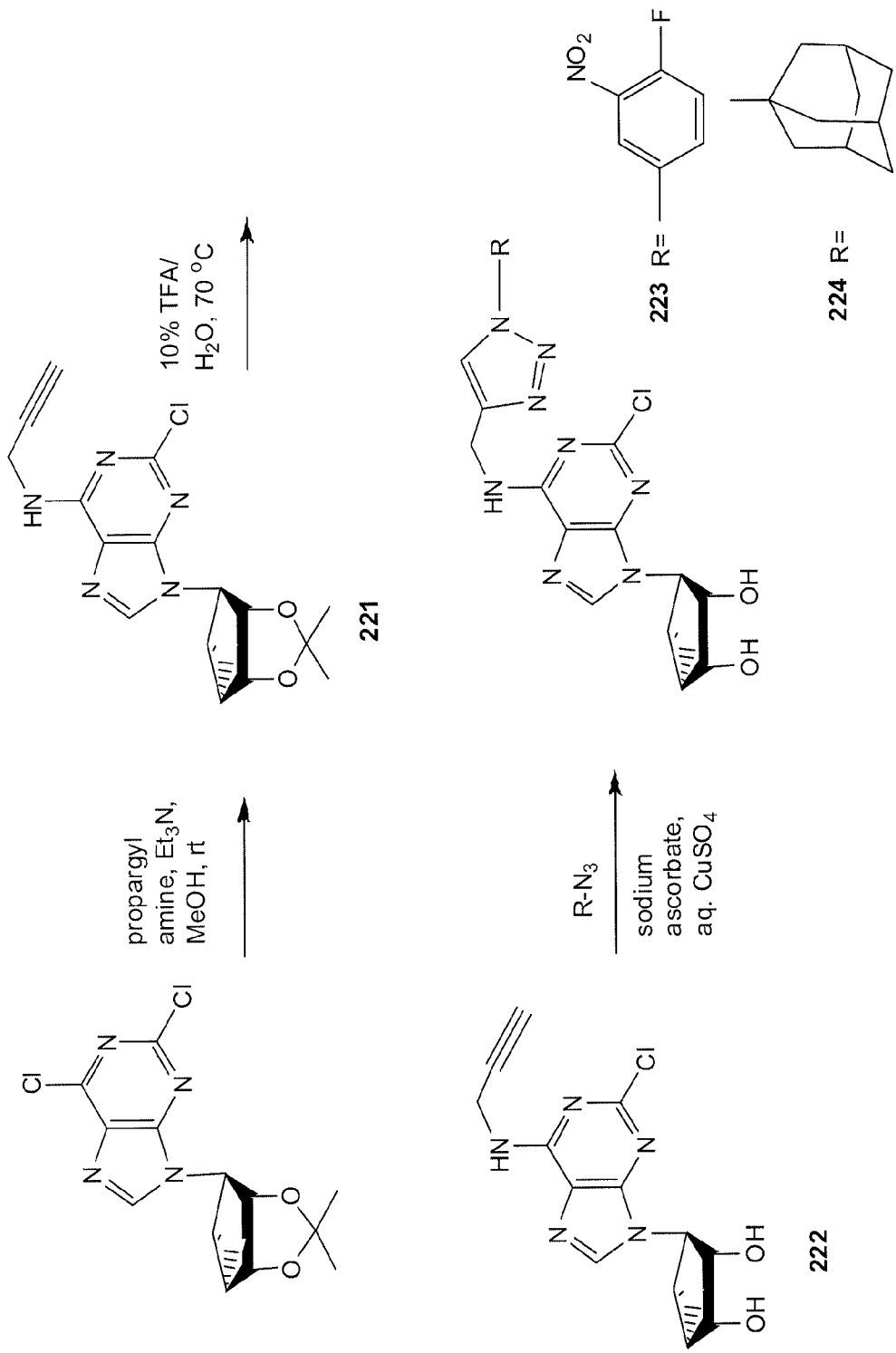
FIG. 27 illustrates a synthetic scheme to prepare additional $N^6$-propargyl compounds and $N^6$-triazolinyl compounds in accordance with an embodiment of the invention.

An isothiazolone azide derivative 32 was synthesized as shown in FIG. 10. This served as the precursor for the adenosine derivative 19. The synthesis of isothiazolone derivatives from 3-benzoylpropionic acid was reported by Tsolomitis et al., *Heterocycles*, 1987, 25, 569. An amide coupling reaction between 27 and p-toluidine formed 4-oxo-4-phenyl-N-p-tolyl-butyramide 28, which was treated with an excess of thionyl chloride to give 5-benzoyl-2-p-tolylisothiazol-3-one 29. Debenzoylation of 29 afforded 2-p-tolylisothiazol-3-one 30 in the presence of 10% aqueous sodium hydroxide in benzene, along with dithietane derivatives as by-products. Compound 30 was transformed with N-bromosuccinimide in the presence of a catalytic amount of benzoyl peroxide in carbon tetrachloride to the bromomethyl derivative 31, which upon treatment with sodium azide afforded 2-(4-azidomethylphenyl)isothiazol-3-one 32.

$^1$H NMR spectra were obtained with a Varian Gemini 300 spectrometer. When using $D_2O$ was used as a solvent, the chemical shifts are expressed as relative ppm from HOD (4.80 ppm).

The purity of the final nucleotide derivatives were determined using a Hewlett-Packard 1100 HPLC equipped with a Zorbax Eclipse 5 mm XDB-C18 analytical column (250×4.6 mm; Agilent Technologies Inc, Palo Alto, Calif.), using a linear gradient solvent system: 5 mM TBAP (tetrabutylammonium dihydrogenphosphate)-$CH_3CN$ from 80:20 to 40:60 in 20 min with a flow rate of 1 mL/min. Peaks were detected by UV absorption (254 nm) using a diode array detector. All derivatives tested for biological activity were shown to be at least 97% pure using this analytical HPLC system.

High-resolution mass measurements were performed on a Micromass/Waters LCT Premier Electrospray Time of Flight (TOF) mass spectrometer coupled with a Waters HPLC system. Unless noted otherwise, reagents and solvents were purchased from Sigma-Aldrich (St. Louis, Mo.). Solutions of the nucleoside analogues in DMSO (5 mM) were prepared for biological testing and stored at −20° C.

The rotaxane azide derivative SRfluor® 680 Azide was obtained from Molecular Targeting Technologies, Inc. (West Chester, Pa.). Alexa Fluor 488 azide and biotin(PEG)4 azide were purchased from Invitrogen Corp. (Carlsbad, Calif.). DMEM/F12 medium and 1 M Tris-HCl (pH 7.5) were purchased from Mediatech, Inc. (Herndon, Va.). Unless noted otherwise, reagents and solvents were purchased from Sigma-Aldrich (St. Louis, Mo.).

Dendrimer Synthesis

All reactions were carried out under a nitrogen atmosphere. N-ethyl-N'-dimethylaminopropylcarbodiimide hydrochloride (EDC.HCl), UDPG acid trisodium salt (UDPGA), UDPG, G2.5 PAMAM (10 wt % solution in methanol), G3 PAMAM (20 wt % solution in methanol), PAMAM dendrimers (G4, G5.5, and G6, 5 wt % solution in methanol) with an ethylenediamine core were purchased. All other reagents and solvents, except those indicated, came from Sigma-Aldrich (St. Louis, Mo.). Dialysis membranes (Spectra/Pore Membrane, MWCO 3500, flat width 18 mm) were purchased from Spectrum Laboratories (Rancho Dominguez, Calif.). Synthesis of compound 103a is described elsewhere, Klotz et al., Naunyn Schmiedegergs. *Arch. Pharmacol.* 1989, 340, 679.

Nuclear magnetic resonance (NMR) spectra were recorded on a Bruker DRX-600 spectrometer with $D_2O$ as a solvent. The chemical shifts are expressed as relative ppm from HOD (4.80). Electrospray ionization mass spectrometry (MS) and matrix-assisted laser desorption ionization (MALDI) time-of-flight MS experiments were performed on a Waters LCT Premier mass spectrometer at the Mass Spectrometry Facility, National Institute of Diabetes and Digestive and Kidney Diseases (NIDDK), NIH. The azido dendrimer precursors were analyzed on a Varian 500 MHz NMR and on a Bruker Vertex 70 FT-IR. Galbraith Laboratories (Knoxville, Tenn.) performed the element analysis.

The following examples further illustrate the invention but, of course, should not be construed as in any way limiting its scope.

Abbreviations: AR, adenosine receptor; cAMP, adenosine 3',5'-cyclic phosphate; CHO, Chinese hamster ovary; Cl-IB-MECA, 2-chloro-$N^6$-(3-iodobenzyl)-5'-N-methylcarboxamidoadenosine; DMEM, Dulbecco's modified Eagle's medium; EDC, 1-ethyl-3-(3-dimethylaminopropyl) carbodiimide; EDTA, ethylenediaminetetraacetic acid; GPCR, G protein-coupled receptor; HATU, 2-(1H-7-azabenzotriazol-1-yl)-1,1,3,3-tetramethyl uronium hexafluorophosphate methanaminium; HEK, human embryonic kidney; HOBT, 1-hydroxybenzotriazole; 1-AB-MECA, $N^6$-(3-iodo-4-aminobenzyl)-5'-N-methylcarboxamidoadenosine; IB-MECA, $N^6$-(3-iodobenzyl)-5'-N-methylcarboxamido-adenosine; NECA, 5'-N-ethylcarboxamidoadenosine; DMF, N,N-dimethylformamide; HEPES, 4-(2-hydroxyethyl)-1-piperazineethanesulfonic acid; HRMS, high resolution mass spectroscopy; TBTA, tris[(1-benzyl-1H-1,2,3-triazol-4-yl) methyl]amine; TEA, triethylamine; TLC, thin layer chromatography; DMSO, dimethylsulfoxide; IBMX, 3-isobutyl-1-methylxanthine; PAMAM, polyamidoamine; PLC, phospholipase C; UDPG, uridine-5'-diphosphoglucose; UDPGA, uridine-5'-diphosphoglucuronic acid.

Example 1

This example illustrates the synthesis of compounds in accordance with an embodiment of the invention. See FIGS. 8-10 for reaction schemes illustrating the synthesis.

(1'S, 2'R, 3'S, 4'S, 5'S)-4'-[6-(3-Chlorobenzylamino)-2-(1,6-heptadiynyl)-9H-purin-9-yl]-(1'S, 2'R, 3'S, 4'S, 5'S)-4'-[6-(3-Chlorobenzylamino)-2-(1,7-octadiynyl)-9H-purin-9-yl]-2',3'-O-isopropylidenebicyclo[3.1.0]hexane-1'-carboxylic acid N-methylamide (7)

To a solution of compound 5 (440 mg, 0.73 mmol) in anhydrous DMF (12 mL), $Pd(PPh_3)_4$ (92 mg, 0.08 mmol), CuI (30.5 mg, 0.16 mmol), 1,7-octadiyne (1.0 mL, 8.01 mmol) and then triethylamine (0.22 mL, 1.6 mmol) was added. The reaction mixture was heated at 60° C. for overnight. Solvent was evaporated under vacuum and the residue was purified on flash silica gel column chromatography ($CH_2Cl_2$:MeOH=70:1) to give the compound 7 (352 mg, 83%) as a foamy syrup. $^1H$ NMR ($CD_3OD$, 300 MHz) δ 8.11 (s, 1H), 7.43 (s, 1H), 7.26-7.33 (m, 3H), 5.74 (d, J=7.2 Hz, 1H), 5.01 (s, 1H), 4.83 (m, 1H), 2.87 (s, 3H), 2.53 (t, J=6.9 Hz, 2H), 2.34-2.31 (m, 3H), 2.10-2.15 (m, 1H), 1.71-1.84 (m, 4H), 1.54-1.57 (m, 4H), 1.40 (t, J=5.4 Hz, 1H), 1.29 (s, 3H). HRMS calculated for $C_{31}H_{34}ClN_6O_3$ $(M+H)^+$: 573.2381. Found 573.2397.

2',3'-O-isopropylidenebicyclo[3.1.0]hexane-1'-carboxylic acid N-methylamide (6)

Compound 6 (81%) was synthesized from 5 following the same procedure as for compound 7. $^1H$ NMR ($CD_3OD$, 300 MHz) δ 8.12 (s, 1H), 7.45 (s, 1H), 7.28-7.34 (m, 3H), 5.76 (d, J=6.9 Hz, 1H), 5.02 (s, 1H), 4.85-4.87 (m, 1H), 2.88 (s, 3H), 2.64 (t, J=6.9 Hz, 2H), 2.41-2.46 (m, 2H), 2.31 (t, J=2.7, 1H) 2.12-2.17 (m, 1H), 1.85-1.94 (m, 2H), 1.56 (m, 4H), 1.40-1.44 (m, 1H). 1.30 (s, 3H). HRMS calculated for $C_{30}H_{32}ClN_6O_3$ $(M+H)^+$: 559.3046. Found 559.3085.

(1'S, 2'R, 3'S, 4'S, 5'S)-4'-[6-(3-Chlorobenzylamino)-2-(1,6-heptadiynyl)-9H-purin-9-yl]-2',3'-dihydroxybicyclo[3.1.0]hexane-1'-carboxylic acid N-methylamide (8)

Compound 8 (86%) was synthesized from 6 following the same procedure as for compound 9. $^1H$ NMR ($CD_3OD$, 300 MHz) δ 8.07 (s, 1H), 7.42 (s, 1H), 7.25-7.42 (m, 3H), 5.01 (d, J=6.9 Hz, 1H), 4.84-4.87 (m, 1H), 3.98 (d, J=6.6 Hz, 1H), 2.86 (s, 3H), 2.59 (t, J=7.2 Hz, 2H), 2.36-2.44 (m, 2H), 2.28 (t, J=2.4 Hz, 1H), 2.06-2.10 (m, 1H), 1.79-1.88 (m, 3H), 1.34-1.39 (m, 1H). HRMS calculated for $C_{27}H_{28}ClN_6O_3$ $(M+H)^+$: 519.1911. Found 519.1912.

(1'S, 2'R, 3'S, 4'S, 5'S)-4'-[6-(3-Chlorobenzylamino)-2-(1,7-octadiynyl)-9H-purin-9-yl]-2',3'-dihydroxybicyclo[3.1.0]hexane-1'-carboxylic acid N-methylamide (9)

To a solution of compound 7 (350 mg, 0.61 mmol) in methanol (7 mL), 10% trifluoromethane sulfonic acid was added and heated at 70° C. for 6 h. Solvent was evaporated and the residue was purified on flash silica gel chromatography ($CH_2Cl_2$:MeOH=40:1) to give the compound 9 (295 mg, 91%) as a syrup. $^1H$ NMR ($CD_3OD$, 300 MHz) δ 8.08 (s, 1H), 7.43 (s, 1H), 7.28-7.33 (m, 3H), 5.02 (d, J=6.6 Hz, 1H), 4.80-4.82 (M, 1H), 4.00 (dd, $J_1$=1.2 Hz, $J_2$=5.7 Hz, 1H), 2.87 (s, 3H), 2.51 (t, J=6.9 Hz, 1H), 2.22-2.30 (m, 3H), 2.07-2.10 (m, 1H), 1.86 (t, J=5.1 Hz, 1H), 1.70-1.81 (m, 4H), 1.35-1.40 (m, 1H). HRMS calculated for $C_{28}H_{30}ClN_6O_3$ $(M+H)^+$: 533.2068. Found 533.2082.

(1S,2R,3S,4R,5S)-4'-(6-(3-Chlorobenzylamino)-2-(6-(1-(4-fluoro-3-nitrophenyl)-1H-1,2,3-triazol-4-yl)pent-1-ynyl)-9H-purin-9-yl)-2',3'-dihydroxybicyclo[3.1.0]hexane-1'-carboxylic acid N-methylamide (10)

Compound 10 (89%) was synthesized from 8 following same procedure as for compound 11. $^1$H NMR (CD$_3$OD, 300 MHz) δ 8.52-8.56 (m, 2H), 8.18-8.22 (m, 1H), 8.08 (s, 1H), 7.59-7.65 (m, 1H), 7.41 (s, 1H), 7.25-7.32 (m, 3H), 5.04 (d, J=5.4 Hz, 1H), 4.80-4.83 (m, 1H), 3.99 (dd, J1=0.9 Hz, J2=5.7 Hz, 1H), 3.04 (t, J=7.5 Hz, 2H), 2.87 (s, 3H), 2.60 (t, J=6.6 Hz, 2H), 2.07-2.17 (m, 3H), 1.86 (t, J=5.1 Hz, 2H), 1.38-1.45 (m, 2H), 0.89-0.96 (m, 1H). HRMS calculated for C$_{33}$H$_{31}$ClFN$_{10}$O$_5$ (M+H)$^+$: 701.2151. Found 701.2172.

(1S,2R,3S,4R,5S)-4'-(6-(3-Chlorobenzylamino)-2-(6-(1-(4-fluoro-3-nitrophenyl)-1H-1,2,3-triazol-4-yphex-1-ynyl)-9H-purin-9-yl)-2',3'-dihydroxybicyclo[3.1.0]hexane-1'-carboxylic acid N-methylamide (11)

To a mixture of compound 9 (34 mg, 0.063 mmol) and 4-fluoro-3-nitro-phenyl azide (16.2 mg, 0.088 mmol) in THF/H$_2$O 3:1 (2 mL), was added freshly prepared 1M sodium ascorbate (51 μL, 0.05 mmol) followed by 7.5% aqueous copper sulfate pentahydrate solution (42 μL, 0.012 mmol) and stirred for over night at room temperature. Solvent was evaporated and the residue was purified on flash silica gel column chromatography (CH$_2$Cl$_2$:MeOH=45:1) to give the clicked product 11 (42 mg, 94%) as a syrup. $^1$H NMR (CD$_3$OD, 300 MHz) δ 8.57-8.58 (m, 1H), 8.49 (s, 1H), 8.20-8.25 (m, 1H), 8.09 (s, 1H), 7.60-7.67 (m, 1H), 7.40 (s, 1H), 7.20-7.32 (m, 3H), 5.03 (d, J=6.6 Hz, 1H), 4.84-4.87 (m, 1H), 3.99 (d, J=6.3 Hz, 1H), 2.91 (t, J=7.5 Hz, 2H), 2.87 (s, 3H), 2.56 (t, J=6.9 Hz, 2H), 1.96-2.11 (m, 3H), 1.75-1.87 (m, 3H), 1.31-1.40 (m, 2H). HRMS calculated for C$_{34}$H$_{33}$ClFN$_{10}$O$_5$ (M+H)$^+$: 715.2308. Found 715.2347.

(1S,2R,3S,4R,5S)-4'-(6-(3-Chlorobenzylamino)-2-(6-(1-(4-amino-phenyl)-1H-1,2,3-triazol-4-yl)hex-1-ynyl)-9H-purin-9-yl)-2',3'-dihydroxybicyclo[3.1.0]hexane-1'-carboxylic acid N-methylamide (12)

To a mixture of compound 9 (4.46 mg, 0.008 mmol) and 4-amino-phenylazide (2 mg, 0.011 mmol) in a mixture of t-butanol (0.5 mL) and water (0.5 mL), was added TBTA (1 mg, 0.001 mmol) and freshly prepared sodium ascorbate (8.3 μL, 0.008 mmol) followed by copper sulfate (8.3 μL, 0.003 mmol). The reaction mixture was stirred at room temperature for overnight, solvent was evaporated and the residue was purified on flash silica gel column chromatography (CH$_2$Cl$_2$:MeOH=30:1) to give the compound 12 (4 mg, 72%) as a syrup. $^1$H NMR (CD$_3$OD, 300 MHz) δ 8.08 (s, 1H), 8.07 (s, 1H), 7.23-7.41 (m, 6H), 6.74 (d, J=8.7 Hz, 2H), 5.01 (d, J=6.9 Hz, 1H), 4.78-4.82 (m, 1H), 3.96 (d, J=6.0 Hz, 1H), 2.82-2.86 (m, 5H), 2.53 (t, J=6.9 Hz, 2H), 2.06-2.16 (m, 2H), 1.93-1.98 (m, 2H), 1.71-1.87 (m, 4H), 1.29-1.39 (m, 1H). HRMS calculated for C$_{34}$H$_{35}$ClN$_{10}$O$_3$Na (M+Na)$^+$: 689.2480. Found 689.2465.

(1S,2R,3S,4R,5S)-4'-(6-(3-Chlorobenzylamino)-2-(6-(1-(4-carboxyl-phenyl)-1H-1,2,3-triazol-4-yl)hex-1-ynyl)-9H-purin-9-yl)-2',3'-dihydroxybicyclo[3.1.0]hexane-1'-carboxylic acid N-methylamide (13)

Compound 13 (81%) was synthesized from 9 following the same procedure as for compound 12. $^1$H NMR (CD$_3$OD, 300 MHz) δ 8.39 (s, 1H), 8.09-8.14 (m, 3H), 7.81-7.84 (m, 2H), 7.22-7.44 (m, 4H), 5.04 (d, J=6.6 Hz, 1H), 4.83-4.85 (m, 1H), 3.99 (d, J=6.6 Hz, 1H), 2.89-2.94 (m, 5H), 2.57 (t, J=6.6 Hz, 2H), 1.98-2.14 (m, 4H), 1.77-1.90 (m, 4H), 1.38-1.43 (m, 1H). HRMS calculated for C$_{35}$H$_{33}$ClN$_9$O$_5$ (M–H)$^+$: 694.2293. Found 694.2311.

(1S,2R,3S,4R,5S)-6-(3-Chlorobenzylamino)-4-(2-(6-(4-(2-bromoacetyl)phenyl)-1H-1,2,3-triazol-4-yphex-1-ynyl)-9H-purin-9-yl)-2',3'-dihydroxybicyclo[3.1.0]hexane-1'-carboxylic acid N-methylamide (14)

Compound 14 (79%) was synthesized from 9 following same procedure as for compound 11. $^1$H NMR (CD$_3$OD, 300 MHz) δ 8.43 (s, 1H), 8.33 (s, 1H), 8.07-8.15 (m, 4H), 7.21-7.42 (m, 4H), 5.01 (d, J=6.6 Hz, 1H), 4.77-4.82 (m, 1H), 4.70 (s, 2H), 3.96 (d, J=6.9 Hz, 1H), 2.86-2.92 (m, 5H), 2.41 (t, J=5.1 Hz, 2H), 1.93-2.10 (m, 4H), 1.74-1.87 (m, 4H), 1.35-1.40 (m, 1H). HRMS calculated for C$_{36}$H$_{35}$ClBrN$_9$O$_4$Na (M+Na)$^+$: 796.1738. Found 796.1713.

(1S,2R,3S,4R,5S)-6-(3-Chlorobenzylamino)-(2-(6-(1-(4-acetamidoethyl)-1H-1,2,3-triazol-4-yl)hex-1-ynyl)-9H-purin-9-yl)-2',3'-dihydroxybicyclo[3.1.0]hexane-1'-carboxylic acid N-methylamide (15)

Compound 15 (86%) was synthesized from 9 following same procedure as for compound 11. $^1$H NMR (CD$_3$OD, 300 MHz) δ 8.09 (s, 1H), 7.78 (s, 1H), 7.43 (s, 1H), 7.27-7.33 (m, 3H), 5.03 (d, J=5.1 Hz, 1H), 4.83-86 (m, 1H), 4.47 (t, J=5.7 Hz, 2H), 4.01 (d, J=6.6 Hz, 1H), 3.62 (t, J=5.7 Hz, 2H), 2.87 (s, 3H), 2.79 (t, J=7.5 Hz, 2H), 2.53 (t, J=7.2 Hz, 2H), 2.07-2.10 (m, 1H), 1.85-1.93 (m, 5H), 1.69-1.74 (m, 2H), 1.36-1.41 (m, 1H). HRMS calculated for C$_{32}$H$_{38}$ClN$_{10}$O$_4$ (M+H)$^+$: 661.2766. Found 661.2751.

(1S,2R,3S,4R,5S)-6-(3-Chlorobenzylamino)-(2-(6-(1-(4-aminobutyl)-1H-1,2,3-triazol-4-yl)hex-1-ynyl)-9H-purin-9-yl)-2',3'-dihydroxybicyclo[3.1.0]hexane-1'-carboxylic acid N-methylamide (16)

Compound 16 (73%) was synthesized from 9 following same procedure as for compound 12. $^1$H NMR (CD$_3$OD, 300 MHz) δ 8.11 (s, 1H), 7.81 (s, 1H), 7.45 (s, 1H), 7.28-7.34 (m, 3H), 5.06 (d, J=6.3 Hz, 1H), 4.80-4.83 (m, 1H), 4.42 (t, J=6.6 Hz, 2H), 4.01 (d, J=6.6 Hz, 1H), 2.85-2.88 (m, 5H), 2.79-2.84 (m, 4H), 2.54 (t, J=7.2 Hz, 2H), 2.08-2.12 (m, 1H), 1.86-1.99 (m, 5H), 1.66-1.78 (m, 2H), 1.54-1.62 (m, 2H), 1.38-1.43 (m, 1H). HRMS calculated for C$_{32}$H$_{40}$ClN$_{10}$O$_3$ (M+H)$^+$: 647.2973. Found 647.2968.

(1S,2R,3S,4R,5S)-6-(3-Chlorobenzylamino)-(2-(6-(1-(4-acetamidobutyl)-1H-1,2,3-triazol-4-yl)hex-1-ynyl)-9H-purin-9-yl)-2',3'-dihydroxybicyclo[3.1.0]hexane-1'-carboxylic acid N-methylamide (17)

To a solution of compound 16 (1.79 mg, 0.002 mmol) in anhydrous DMF (0.5 mL), acetic acid N-hydroxysuccinimide ester (1 mg, 0.006 mmol) was added and the mixture stirred at room temperature for overnight. Solvent was evaporated and the residue was purified by preparative TLC(CH$_2$Cl$_2$:MeOH=25:1) to give the compound 17 as a syrup (1.26 mg, 66%). $^1$H NMR (CD$_3$OD, 300 MHz) δ 8.11 (s, 1H), 7.80 (s, 1H), 7.44 (s, 1H), 7.27-7.33 (m, 3H), 5.04 (d, J=6.3 Hz, 1H), 4.83-4.85 (m, 1H), 4.39 (t, J=6.9 Hz, 2H), 3.70 (t, J=3.9 Hz, 4H), 3.59 (m, 4H), 2.87 (s, 3H), 2.78-2.86 (m, 2H), 2.48-2.57

(m, 2H), 1.93 (s, 3H), 1.85-1.91 (m, 2H), 1.68-1.79 (m, 2H), 1.39-1.52 (m, 2H), 1.23-1.43 (m, 2H). HRMS calculated for $C_{34}H_{41}ClN_{10}O_4Na$ (M+Na)$^+$: 711.2898. Found 711.2917.

(1S,2R,3S,4R,5S)-6-(3-Chlorobenzylamino)-(2-(6-(1-(adamantyl)-1H-1,2,3-triazol-4-yl)hex-1-ynyl)-9H-purin-9-yl)-2',3'-dihydroxybicyclo[3.1.0]hexane-1'-carboxylic acid N-methylamide (18)

Compound 18 (76%) was synthesized from 9 following same procedure as for compound 11. $^1$H NMR (CD$_3$OD, 300 MHz) δ 8.09 (s, 1H), 7.81 (s, 1H), 7.44 (s, 1H), 7.25-7.33 (m, 3H), 5.03 (d, J=6.6 Hz, 1H), 4.83-4.85 (m, 1H), 3.98 (d, J=6.0 Hz, 1H), 2.86 (s, 3H), 2.79 (t, J=7.2 Hz, 2H), 2.51 (t, J=6.9 Hz, 2H), 2.16 (s, 9H), 2.06-2.10 (m, 1H), 1.68-1.95 (m, 13H), 1.36-1.40 (m, 1H). HRMS calculated for $C_{38}H_{45}ClN_9O_3$ (M+H)$^+$: 710.3334. Found 710.3352.

(1S,2R,3S,4R,5S)-6-(3-Chlorobenzylamino)-(2-(1-(4-3-oxoisothiazol-2(3H)-yl)benzyl-1H-1,2,3-triazol-4-yphex-1-ynyl)-9H-purin-9-yl)-2',3'-dihydroxybicyclo[3.1.0]hexane-β-carboxylic acid N-methylamide (19)

Compound 19 (81%) was synthesized from 9 following same procedure as for compound 11. $^1$H NMR (CD$_3$OD, 300 MHz) δ 8.56 (d, J=6.3 Hz, 1H), 8.08 (s, 1H), 7.83 (s, 1H), 7.53-7.56 (m, 2H), 7.39-7.42 (m, 2H), 7.25-7.30 (m, 4H), 6.29 (d, J=6.3 Hz, 1H), 5.6 (s, 2H), 5.02 (d, J=6.9 Hz, 1H), 4.80-4.83 (m, 1H), 3.97 (d, J=6.0 Hz, 1H), 2.86 (s, 3H), 2.80 (t, J=7.2 Hz, 2H), 2.50 (t, J=7.2 Hz, 2H), 2.06-2.10 (m, 1H), 1.84-1.92 (m, 4H), 1.67-1.74 (m, 2H), 1.35-1.40 (m, 1H). HRMS calculated for $C_{38}H_{38}ClSN_{10}O_4$ (M+H)$^+$: 765.2487. Found 765.2461.

(1S,2R,3S,4R,5S)-6-(3-Chlorobenzylamino)-(2-(6-(1-(6-(5-(3aS,4S,6aR)-oxohexahydro-1H-thieno[3,4-d]imidazol-4-yl)pentanamido)hexyl-1H-1,2,3-triazol-4-yl)hex-1-ynyl)-9H-purin-9-yl)-2',3'-dihydroxybicyclo[3.1.0]hexane-1'-carboxylic acid N-methylamide (20)

Compound 20 (73%) was synthesized from 9 following same procedure as for compound 12. $^1$H NMR (CD$_3$OD, 300 MHz) δ 8.08 (s, 1H), 7.77 (s, 1H), 7.42 (s, 1H), 7.23-7.31 (m, 3H), 5.02 (d, J=6.3 Hz, 1H), 4.83-4.86 (m, 1H), 4.45-4.49 (m, 1H), 4.26-4.35 (m, 3H), 3.98 (d, J=7.2 Hz, 1H), 3.65-3.69 (m, 3H), 3.54-3.57 (m, 3H), 3.03-3.24 (m, 4H), 2.85 (s, 3H), 2.78 (t, J=7.5 Hz, 2H), 2.51 (t, J=7.2 Hz, 2H), 2.06-2.28 (m, 6H), 1.81-1.89 (m, 6H), 1.60-1.72 (m, 6H), 1.34-1.46 (m, 2H). HRMS calculated for $C_{44}H_{57}ClN_{12}O_5SNa$ (M+Na)$^+$: 923.3882. Found 923.3887.

1S,2R,3S,4R,5S)-6-(3-Chlorobenzylamino)-(2-(6-(1-(7-oxo-7-(6-(5-(3aS,4S,6aR)-oxohexahydro-1H-thieno[3,4-d]imidazol-4-yl)pentanamido)hexylamino)heptyl)-1H-1,2,3-triazol-4-yl)hex-1-ynyl)-9H-purin-9-yl)-2',3'-dihydroxybicyclo[3.1.0]hexane-1'-carboxylic acid N-methylamide (21)

Compound 21 (82%) was synthesized from 9 following same procedure as for compound 12. $^1$H NMR (CD$_3$OD, 300 MHz) δ 8.03 (s, 1H), 7.81 (s, 1H), 7.46 (s, 1H), 7.29-7.35 (m, 3H), 5.05 (d, J=6.5 Hz, 1H), 4.80-4.85 (m, 1H), 4.42-4.46 (m, 4H), 3.99 (d, J=6.9 Hz, 1H), 3.79-3.85 (m, 8H), 3.56-3.62 (m, 8H), 3.15-3.26 (m, 4H), 2.89 (s, 3H), 2.23-2.57 (m, 6H), 1.03-1.91 (bm, 28H). HRMS calculated for $C_{55}H_{78}ClN_{13}O_{10}SNa$ (M+Na)$^+$: 1170.5302. Found 1170.5288.

2-(6-Amino-3-imino-4,5-disulfonato-3H-xanthen-9-yl)-5-(6-(4-(6-(6-3-chlorobenzylamino)-9-((1S,2R,3S,4R,5S)-3,4-dihydroxy-5-(methylcarbamoyl)bicycle[3.1.0]hexane-2-yl)-9H-purin-2-yl)hex-5-ynyl)-1H-1,2,3-triazol-1-yl)hexylcarbamoyl)benzoate (23)

Compound 23 (76%) was synthesized from 9 following same procedure as for compound 12. $^1$H NMR (CD$_3$OD, 300 MHz) δ 8.56 (s, 1H), 8.07 (s, 1H), 7.83 (s, 1H), 7.26-7.43 (m, 4H), 7.09-7.12 (m, 2H), 6.90 (d, J=6.9 Hz, 2H), 5.75 (d, J=6.7 Hz, 1H), 5.57 (d, J=6.8 Hz, 1H), 4.98 (d, J=6.6 Hz, 1H), 4.80-4.84 (m, 1H), 4.13 (t, J=3.6 Hz, 2H), 3.98 (d, J=7.2 Hz, 1H), 3.69-3.72 (m, 4H), 3.59-3.64 (m, 4H), 2.89 (s, 3H), 2.50-2.55 (m, 4H), 2.19-2.32 (m, 4H), 1.21-1.46 (m, 7H). HRMS calculated for $C_{55}H_{54}ClN_{12}O_{13}S_2$ (M+H)$^+$: 1189.3063. Found 1189.3038.

(1S,2R,3S,4R,5S)-6-(3-Chlorobenzylamino)-(2-(1,6-bis(4-isothiocyante-phenyl)-1H-bis(1,2,3-triazol-4-yl)hex-1-ynyl)-9H-purin-9-yl)-2',3'-dihydroxybicyclo[3.1.0]hexane-1'-carboxylic acid N-methylamide (25)

To a mixture of compound 9 (17 mg, 0.031 mmol) and 4-azidophenyl isothiocyante (7.8 mg, 0.044 mmol) in in THF/H$_2$O 3:1 (1.2 mL), was added freshly prepared 1M sodium ascorbate (26 μL, 0.025 mmol) followed by 7.5% aqueous copper sulfate pentahydrate solution (21 μL, 0.006 mmol) and stirred for 2 d at room temperature. Solvent was evaporated and the residue was purified on flash silica gel column chromatography (CH$_2$Cl$_2$:MeOH=20:1) to give an unusual clicked product 25 (21 mg, 75%) as a syrup. $^1$H NMR (CD$_3$OD, 300 MHz) δ 8.29 (s, 1H), 8.12 (s, 1H), 7.71 (d, J=8.7 Hz, 2H), 7.63 (d, J=9.0 Hz, 2H), 7.50 (d, J=6.6 Hz, 2H), 7.41 (s, 1H), 7.23-7.30 (m, 3H), 7.08 (d, J=6.6 Hz, 2H), 5.02 (d, J=5.2 Hz, 1H), 4.79-4.81 (m, 1H), 3.97 (d, J=6.6 Hz, 1H), 2.83-2.91 (m, 5H), 2.55 (t, J=6.9 Hz, 2H), 1.97-2.09 (m, 4H), 1.74-1.86 (m, 4H), 1.39-1.47 (m, 1H). HRMS calculated for $C_{41}H_{40}ClN_{14}O_3S$ (M-CS)$^+$: 843.2817. Found 843.2812.

(1S,2R,3S,4R,5S)-6-(3-Chlorobenzylamino)-(2-(6-(1-(4-isothiocyante-phenyl)-1H-1,2,3-triazol-4-yl)hex-1-ynyl)-9H-purin-9-yl)-2',3'-dihydroxybicyclo[3.1.0]hexane-1'-carboxylic acid N-methylamide (26)

To a mixture of compound 9 (4.22 mg, 0.007 mmol) and 4-isothiocyante-phenylazide (2 mg, 0.011 mmol) in a mixture of t-butanol (0.3 mL) and water (0.3 mL), was added TBTA (1 mg, 0.001 mmol) and freshly prepared sodium ascorbate (7.9 μL, 0.007 mmol) followed by copper sulfate (7.9 μL, 0.002 mmol). The reaction mixture was stirred at room temperature for overnight. The starting material and product came in same Rf value in TLC. Solvent was evaporated and the residue was purified on flash silica gel column chromatography (CH$_2$Cl$_2$:MeOH=25:1) to give the compound 26 (3.8 mg, 69%) as a syrup, no diclicked product was detected. $^1$H NMR (CD$_3$OD, 300 MHz) δ 8.35 (s, 1H), 8.09 (s, 1H), 7.83 (d, J=6.9 Hz, 2H), 7.40-7.43 (m, 3H), 7.24-7.32 (m, 3H), 5.02 (d, J=6.3 Hz, 1H), 4.83-4.85 (m, 1H), 3.97 (d, J=6.3 Hz, 1H), 2.87-2.92 (m, 5I-1), 2.55 (t, J=6.9 Hz, 2H), 1.97-2.13 (m, 4H), 1.87 (t, J=4.5

Hz, 2H), 1.74-1.83 (m, 2H), 1.38-1.41 (m, 1H). HRMS calculated for $C_{35}H_{34}ClN_{10}O_3S$ (M+H)$^+$: 709.2225. Found 709.2236.

4-Oxo-4-phenyl-N-p-tolyl-butyramide (28)

EDC (347 mg, 1.81 mmol) and HOBT (254 mg, 1.88 mmol) were added to mixture of p-toluidine (129 mg, 1.20 mmol) and 3-benzoylpropionic acid 27 (218 mg, 1.21 mmol) in 1,4-dioxane (3 mL) at room temperature. It was stirred for 20 minutes and then added triethylamine (0.5 mL, 3.59 mmol). The reaction mixture was stirred for 20 h at room temperature and the solvent was evaporated under vacuum. The residue was purified by flash silica gel column chromatography (hexane:ethyl acetate=3:1 to 2:1) yielded the compound 28 (252 mg, 78%). $^1$H-NMR (CDCl$_3$, 300 MHz) δ 2.30 (s, 3H), 2.80 (t, J=6.3 Hz, 2H), 3.45 (t, J=6.3 Hz, 2H), 7.10 (d, J=8.4 Hz, 2H), 7.39 (d, J=8.4 Hz, 2H), 7.47 (m, 2H), 7.58 (m, 1H), 7.99 (m, 1H).

5-Benzoyl-2-p-tolylisothiazol-3-one (29)

A solution of 4-oxo-4-phenyl-N-p-tolyl-butyramide 28 (252 mg, 0.944 mmol) in thionyl chloride (1 mL) was stirred for 16 h at room temperature. Excess thionyl chloride was removed under vacuum and the residue was purified by flash silica gel column chromatography (hexane:ethyl acetate=10:1 to 4:1) to give the compound 29 (216 mg, 77%). $^1$H-1-NMR (CDCl$_3$, 300 MHz) δ 2.40 (s, 3H), 6.82 (s, 1H), 7.28 (m, 2H), 7.54 (m, 4H), 7.71 (m, 1H), 7.96 (m, 2H). HRMS: calculated for $C_{17}H_{14}NO_2S$ (M+H)$^+$296.0745. Found 296.0762.

2-p-Tolylisothiazol-3-one (30)

Aqueous sodium hydroxide (4 mL, 10%) was added to the solution of 5-benzoyl-2-p-tolylisothiazol-3-one 29 (203 mg, 0.678 mmol) in benzene (9 mL), and the mixture was stirred for 3 d at room temperature. The reaction mixture was added water (20 mL) and extracted with ethyl acetate. The combined organic layer was dried (MgSO$_4$), filtered and evaporated. The residue was purified by flash silica gel column chromatography (hexane:ethyl acetate=2:1 to 1:1) and gave the compound 30 (77 mg, 59%). $^1$H-1-NMR (CDCl$_3$, 300 MHz) δ 2.38 (s, 3H), 6.32 (d, J=6.6 Hz, 1H), 7.25 (d, J=8.1 Hz, 2H), 7.44 (d, J=8.1 Hz, 2H), 8.14 (d, J=6.6 Hz, 1H). HRMS: calculated for $C_{10}H_{10}NOS$ (M+H)$^+$192.0483. Found 192.0494.

2-(4-Bromomethylphenyl)isothiazol-3-one (31)

Catalytic amount of benzoyl peroxide (4 mg) was added to a solution of 2-p-tolylisothiazol-3-one 30 (123 mg, 0.643 mmol), and N-bromosuccinimide (121 mg, 0.673 mmol) in carbon tetrachloride (8 mL), which was refluxed for 2 h and then cooled to room temperature. Solvent was evaporated under low pressure and the residue was purified by flash silica gel column chromatography (methylene chloride:methanol=50:1 to 20:1), afforded the compound 31 (182 mg, 93%). $^1$H-NMR (CDCl$_3$, 300 MHz) δ 4.50 (s, 2H), 6.33 (d, J=6.3 Hz, 1H), 7.47 (d, J=8.4 Hz, 2H), 7.59 (d, J=8.4 Hz, 2H), 8.16 (d, J=6.3 Hz, 1H). HRMS: calculated for $C_{10}H_9NOSBr$ (M+H)$^+$269.9588. Found 269.9593.

2-(4-Azidomethylphenyl)isothiazol-3-one (32)

Sodium azide (6.0 mg, 0.0923 mmol) was added to a solution of 2-(4-bromomethylphenyl)isothiazol-3-one 31 (18.2 mg, 0.0674 mmol) in DMF (1 mL) and stirred for 20 h at room temperature. Water (10 mL) was added and the mixture was extracted with diethyl ether. The combined organic layer was dried (MgSO$_4$), filtered and evaporated. The residue was purified on flash silica gel column chromatography (hexane: ethyl acetate=4:1 to 1:1), afforded the desired compound 32 (11.7 mg, 75%). $^1$H-NMR (CDCl$_3$, 300 MHz) δ 4.38 (s, 2H), 6.34 (d, J=6.3 Hz, 1H), 7.41 (d, J=8.4 Hz, 2H), 7.64 (d, J=8.4 Hz, 2H), 8.17 (d, J=6.3 Hz, 1H). HRMS: Found 233.0496. Calcd for $C_{10}H_9N_4OS$ (M+H)$^+$233.0497.

Example 2

This example illustrates some of the properties of the compounds in accordance within an embodiment of the invention.

Receptor Binding and Functional Assays

[$^3$H]Adenosine-5'-N-methyluronamide (36, [$^3$H]NECA, 42.6 Ci/mmol) was obtained from Perkin Elmer. [$^3$H](2-[p-(2-Carboxyethyl)phenyl-ethylamino]-5'-N-ethylcarboxamido-adenosine) (37, [$^3$H]CGS21680, 40.5 Ci/mmol) and [$^{125}$I]N$^6$-(4-amino-3-iodobenzyl)adenosine-5'-N-methyluronamide (38, [$^{125}$I]I-AB-MECA, 2200 Ci/mmol) were purchased from Perkin-Elmer Life and Analytical Science (Boston, Mass.). Test compounds were prepared as 5 mM stock solutions in DMSO and stored frozen at −20° C.

Cell Culture and Membrane Preparation:

CHO cells stably expressing the recombinant hA$_1$ and hA$_3$Rs, and HEK-293 cells stably expressing the hA$_{2A}$AR were cultured in Dulbecco's modified Eagle medium (DMEM) and F12 (1:1) supplemented with 10% fetal bovine serum, 100 units/mL penicillin, 100 μg/mL streptomycin, and 2 mmol/mL glutamine. In addition, 800 μg/mL geneticin was added to the A$_{2A}$ media, while 500 μg/mL hygromycin was added to the A$_1$ and A$_3$ media. After harvesting, cells were homogenized and suspended in PBS. Cells were then centrifuged at 240 g for 5 min, and the pellet was resuspended in 50 mM Tris-HCl buffer (pH 7.5) containing 10 mM MgCl$_2$. The suspension was homogenized and was then ultra-centrifuged at 14,330 g for 30 min at 4° C. The resultant pellets were resuspended in Tris buffer, incubated with adenosine deaminase (3 units/mL) for 30 min at 37° C. The suspension was homogenized with an electric homogenizer for 10 sec, pipetted into 1 mL vials and then stored at −80° C. until the binding experiments were conducted. The protein concentration was measured using the BCA Protein Assay Kit from Pierce Biotechnology, Inc. (Rockford, Ill.).

Binding Assays:

Into each tube in the binding assay was added 50 μL of increasing concentrations of the test ligand in Tris-HCl buffer (50 mM, pH 7.5) containing 10 mM MgCl$_2$, 50 μl, of the appropriate agonist radioligand, and finally 100 μL of membrane suspension. For the A$_1$AR (22 μg of protein/tube) the radioligand used was [$^3$H]36 (final concentration of 3.5 nM). For the A$_{2A}$AR (20 μg/tube) the radioligand used was [$^3$H]37 (10 nM). For the A$_3$AR (21 μg/tube) the radioligand used was [$^{125}$I]38 (0.34 nM). Nonspecific binding was determined using a final concentration of 10 μM unlabeled 36 diluted with the buffer. The mixtures were incubated at 25° C. for 60 min in a shaking water bath. Binding reactions were terminated by filtration through Brandel GF/B filters under a reduced pressure using a M-24 cell harvester (Brandel, Gaithersburg, Md.). Filters were washed three times with 3 mL of 50 mM ice-cold Tris-HCl buffer (pH 7.5). Filters for A$_1$ and A$_{2A}$AR binding were placed in scintillation vials containing 5 mL of Hydrofluor scintillation buffer and counted using a Perkin Elmer Liquid Scintillation Analyzer (Tri-Carb 2810TR). Filters for $A_3AR$ binding were counted using a Packard Cobra II γ-counter. The $K_i$ values were determined using GraphPad Prism for all assays.

Cyclic AMP Accumulation Assay:

Intracellular cyclic AMP levels were measured with a competitive protein binding method. Nordstedt, C., et al., *Anal. Biochem.*, 1990, 189 231; Post, S. R., et al., *Methods Mol. Biol.*, 2000, 126, 363. CHO cells that expressed the recombinant human $A_3AR$ were harvested by trypsinization. After centrifugation and resuspended in medium, cells were planted in 24-well plates in 1.0 mL medium. After 24 h, the medium was removed and cells were washed three times with 1 mL DMEM, containing 50 mM HEPES, pH 7.4. Cells were then treated with the agonist NECA and/or test compound in the presence of rolipram (10 µM) and adenosine deaminase (3 units/mL). After 45 min forskolin (10 µM) was added to the medium, and incubation was continued for an additional 15 min. The reaction was terminated by removing the supernatant, and cells were lysed upon the addition of 200ł of 0.1 M ice-cold HCl. The cell lysate was resuspended and stored at −20° C. For determination of cyclic AMP production, protein kinase A (PKA) was incubated with [$^3$H]cyclic AMP (2 nM) in $K_2HPO_4$/EDTA buffer ($K_2HPO_4$, 150 mM; EDTA, 10 mM), 20 µL of the cell lysate, and 30 µL 0.1 M HCl or 50 µL of cyclic AMP solution (0-16 pmol/200 µL for standard curve). Bound radioactivity was separated by rapid filtration through Whatman GF/C filters and washed once with cold buffer. Bound radioactivity was measured by liquid scintillation spectrometry.

TABLE 1

Potency of a series of (N)-methanocarba adenosine derivatives at three subtypes of human ARs.

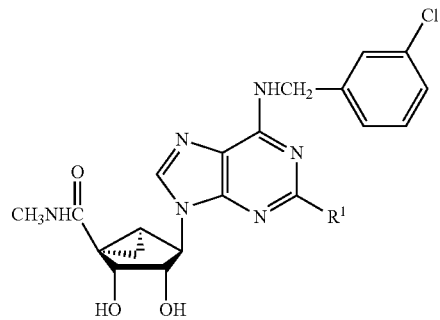

1-3, 8, 9, 25

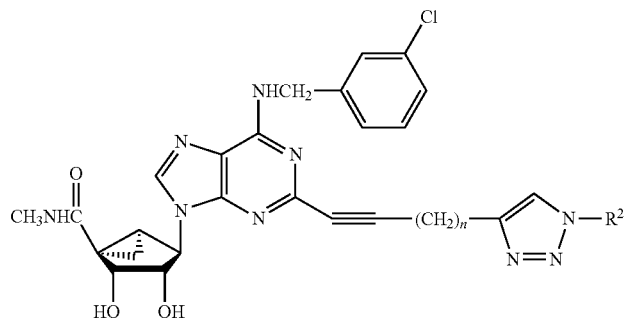

10-23, 26

| Compd. | Structure | Affinity ($K_i$, nM) or % inhibition[a] | | |
|---|---|---|---|---|
| | | $A_1$ | $A_{2A}$ | $A_3$ |
| | $R^1$ | | | |
| 1[b,c] | C≡C(CH$_2$)$_2$CONH(CH$_2$)$_2$NH—CO—(CH$_2$)$_5$Cy5 | (36 ± 3%) | 4730 ± 1020 | 17.2 ± 3.1 |
| 2[b,c] | C≡C(CH$_2$)$_2$CONH(CH$_2$)$_2$NH-biotin | (1 ± 1%) | (51 ± 2%) | 36.4 ± 5.6 |
| 3[b,c] | C≡C(CH$_2$)$_2$CONH(CH$_2$)$_2$NH—CO(CH$_2$)$_5$NH-biotin | (12 ± 4%) | (47 ± 11%) | 57.7 ± 16.2 |
| 25[e] | (structure with bis-triazole-NCS) | (4 ± 2%) | (40 ± 3%) | 8.8 ± 1.3 |

TABLE 1-continued

| # | n | R² | | | |
|---|---|---|---|---|---|
| 8 | | C≡C(CH₂)₃C≡CH | (36 ± 4%) | 4330 ± 500 | 23.6 ± 3.9 |
| 9 | | C≡C(CH₂)₄C≡CH | (31 ± 2%) | 7040 ± 1430 | 29.4 ± 9.8 |
| 10 | 3 | 3-nitro-4-fluorophenyl | (10 ± 3%) | (39 ± 4%) | 26.0 ± 8.2 |
| 11[e] | 4 | 3-nitro-4-fluorophenyl | (8 ± 4%) | 6730 ± 280 | 10.6 ± 3.8 |
| 12 | 4 | 4-aminophenyl | (3 ± 1%) | 5490 ± 1150 | 87.1 ± 13.1 |
| 13 | 4 | 4-carboxyphenyl | (0 ± 0%) | (40 ± 1%) | 180 ± 23 |
| 26 | 4 | 4-isothiocyanatophenyl | (2 ± 11%) | (28 ± 4%) | 37.5 ± 16.0 |
| 14[e] | 4 | 4-(α-Br-phenacyl) | (12 ± 3%) | 5740 ± 730 | 9.6 ± 1.3 |
| 15 | 4 | (CH₂)₂NHCOCH₃ | (12 ± 4%) | 2440 ± 320 | 22.3 ± 1.6 |
| 16 | 4 | (CH₂)₄NH₂ | (13 ± 3%) | 1630 ± 350 | 47.0 ± 1.8 |
| 17 | 4 | (CH₂)₄NHCOCH₃ | (17 ± 1%) | 7240 ± 510 | 89.5 ± 12.6 |
| 18[e] | 4 | 1-adamantyl | (22 ± 2%) | 3280 ± 700 | 6.5 ± 0.5 |
| 19 | 4 | (see structure) | (15 ± 3%) | (49 ± 1%) | 102 ± 25 |
| 20[d] | 4 | —(CH₂)₆NH-biotin | (0 ± 0%) | (27 ± 1%) | 285 ± 54 |
| 21[d] | 4 | —(CH₂)₆CONH(CH₂)₂[O(CH₂)]₄NH-biotin | (0 ± 0%) | (19 ± 5%) | 235 ± 43 |
| 22 | 4 | Rotaxane derivative | (0 ± 0%) | (2 ± 1%) | 239 ± 43 |
| 23[d] | 4 | (CH₂)₆NHCO-Alexa Fluor | (0 ± 0%) | (23 ± 5%) | 416 ± 45 |

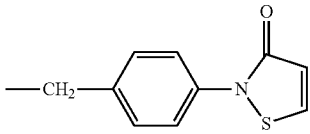

[a]All experiments were done on CHO or HEK293 (A₂ₐ only) cells stably expressing one of four subtypes of human ARs. The binding affinity for A₁, A₂ₐ and A₃ARs was expressed as $K_i$ values (n = 3-5) and was determined by using agonist radioligands ([³H]36; [³H]37; or [¹²⁵I]38; respectively), unless noted.
A percent in parentheses refers to inhibition of radioligand binding at 10 μM.
[b]Values from Tosh 1 (Tosh, et al., "Functionalized congeners of A₃ adenosine receptor-selective nucleosides containing a bicycle[3.1.0]hexane ring system," J. Med. Chem., 2009, 52:7580-7592) and Tosh 2 (Tosh, et al., "2- Dialkynyl derivatives of (N)-methanocarba nucleosides: "Clickable" A₃ adenosine receptor-selective agonists," Bioorg. Med. Chem., 2010, 18:508-517).
[c]Structure given in Chart 1.
[d]Structure given in Scheme 1.
[e]11, MRS5223; 14, MRS5226; 15, MRS5233; 18, MRS5224; 25, MRS5225.

TABLE 2

Maximal efficacy of (N)-methanocarba adenosine derivatives in a functional assay at the A₃Ar.

| Compound | % Inhibition of cAMP formation[a] at hA₃ AR |
|---|---|
| IB-MECA | 99 ± 6 |
| Cl-IB-MECA | 97 |
| 36, NECA | 100 |
| 1[b] | 94.4 ± 9.6 |
| 2[b] | 84.5 ± 12.0 |
| 3[b] | 107 ± 18 |
| 25 | 83.6 ± 7.2 |
| 8 | 18.3 ± 7.6 |
| 9 | 60.2 ± 17.0 |
| 10 | ND |
| 11 | 116 ± 22 |
| 12 | 44.3 ± 2.4 |
| 13 | 83.4 ± 13.1 |
| 26 | 19.5 ± 14.5 |
| 14 | 109 ± 12 |
| 15 | 93.6 ± 17.7 |
| 16 | 64.4 ± 12.4 |
| 17 | 59.7 ± 19.2 |
| 18 | 27.8 ± 17.4 |
| 19 | 75.9 ± 16.5 |
| 20 | 55.6 ± 12.5 |
| 21 | 41.8 ± 11.3 |
| 22 | 111 ± 18 |
| 23 | 37.8 ± 14.6 |

[a]The efficacy at the human A₃AR was determined by inhibition of forskolin-stimulated cyclic AMP production in AR-transfected CHO cells, as described in the text. At a concentration on of 10 μM, in comparison to the maximal effect of a full agonist NECA at 10 μM. Data are expressed as mean ± standard error (n = 3). ND, not determined.
[b]Values from Tosh et al.⁹

Example 3

This example illustrates a method of preparing dendrimer conjugates in accordance with another embodiment of the invention. See FIGS. 11-14.

G4 PAMAM, Conjugated with 6-heptynoic acid (115)

Freshly prepared aqueous sodium ascorbate (1 M, 42 μL, 42.1 μmmol) was added to a mixture of G4 PAMAM dendrimer 113 (6.74 mg, 0.42 μmol) and 6-heptynoic acid (1.33 mg, 10.5 μmol) in a mixture of t-butanol (0.3 mL) and water (0.3 mL), then 7.5% aqueous cupric sulfate (70 μL, 20.8 μmmol) was added. The reaction mixture was stirred at room temperature overnight, and the product was purified by dialysis in water. The mixture was lyophilized to yield compound 115 (5.45 mg, 68%) as a white foamy solid. MALDI-MS: calcd. 19,029. Found 18,928.

G4 PAMAM, Conjugated with A₃AR Agonist 103a and 6-heptynoic Acid (107)

Freshly prepared aqueous sodium ascorbate (1 M, 31 μL, 31 μmmol) was added to a mixture of compound 115 (5.45 mg, 0.28 μmol) and compound 103a (4.13 mg, 7.74 mol) in a mixture of t-butanol (0.3 mL) and water (0.3 mL), then 7.5% aqueous cupric sulfate (51 μl, 14.3 μmol) was added. The reaction mixture was stirred at room temperature overnight, and the product was purified by dialysis in water. The mixture was lyophilized to yield compound 107 (5.8 mg, 60%) as a white foamy solid. ¹H NMR (DMSO-d₆, 600 MHz) δ 8.51 (s), 8.14 (s), 7.61 (s), 7.31-7.41 (m), 5.46 (s), 5.68-5.95 (m), 3.86 (s), 2.66 (s), 2.21 (s), 1.8 (s), 1.61 (bs), 1.11-1.29 (m). MALDI-MS: calcd. 33,852. Found 34,088.

G4 PAMAM, Conjugated with A$_3$AR Agonist 103a (106)

The procedure used for compound 107 was followed to synthesize compound 106 (69%) from 103a. $^1$H NMR (DMSO-d$_6$, 400 MHz) δ 8.50 (bs), 8.15 (bs), 7.60 (s), 7.29-7.59 (m), 5.44 (s), 4.67-5.05 (m), 4.16 (s), 3.86 (s), 2.78 (s), 2.67 (s), 2.08-2.23 (m), 1.82 (s), 1.61 (s), 0.98-1.30 (m). MALDI-MS: calcd. 49,991. Found 50,844.

G4 PAMAM, Conjugated with UDPGA (117)

EDC.HCl (12.5 mg, 65.2 μmol) was added to a solution of compound 105 (15.3 mg, 1.01 μmol and UDPGA trisodium salt 116 (22.9 mg, 35.43 mop in dimethylsulfoxide (DMSO), then 0.1 M 2-(N-morpholino)ethanesulfonic acid buffer (140 μL) was added. 0.1 M HCl was used to adjust the pH of the reaction mixture to 4.5-5.0. The reaction mixture was stirred at room temperature overnight, and the product was purified by extensive dialysis followed by lyophilization to yield compound 117 (22 mg, 64%). $^1$H NMR (DMSO-d$_6$, 400 MHz) δ 8.19 (s), 7.86-8.14 (m), 6.55 (m), 5.80 (s), 5.67 (s), 5.38-5.47 (m), 4.07 (s), 3.97 (s), 3.63 (br s), 3.25 (s), 3.12 (s), 2.91 (s), 2.69 (s), 2.24 (s). MALDI-MS: calcd. 33,060. Found 33,036.

G4 PAMAM, Conjugated with UDPGA and A$_3$AR Agonist 103a (108)

The procedure used for compound 107 was followed to synthesize compound 108 (66%) from compound 117. MALDI-MS: calcd. 50,092. Found 50,610.

G2.5 PAMAM, Conjugated with A$_3$AR Agonist 119 (109)

The procedure used for compound 117 was followed to synthesize compound 109 (54%) from dendrimer 118 and compound 119. $^1$H NMR (D$_2$O, 600 MHz) δ 7.98 (br s), 6.88 (br s), 4.56 (br s), 3.85 (br s), 3.55 (br s), 3.45 (br s), 3.16-3.36 (m), 3.16 (br s), 3.08 (br s), 2.56-2.98 (m), 2.54 (s), 2.24-2.48 (m), 1.92 (br s), 1.68 (br s). MALDI-MS: calcd. 10,598. Found 10,783.

G2.5 PAMAM, Conjugated with A$_3$AR Agonist 120 (110)

The procedure used for compound 117 was followed to synthesize compound 110 (67%) from dendrimer 118 and compound 120. $^1$H NMR (DMSO-d$_6$, 600 MHz) δ 8.11 (s), 7.85-8.01 (m), 7.58 (s), 7.36 (s), 7.18-7.32 (m), 5.06-5.21 (m), 4.88-4.93 (m), 4.65 (s), 4.59 (s), 3.86-3.91 (m), 3.07 (s), 2.65 (s), 2.39 (s), 2.21 (s), 1.85 (s), 1.74 (br s), 1.59 (br s), 1.21-1.33 (m), 1.03 (br s). MALDI-MS: calcd. 8370. Found 8369.

G3 PAMAM, Conjugated with A$_3$AR Agonist 122 (1H)

The procedure used for compound 117 was followed to synthesize compound 111 (71%) from dendrimer 121 and compound 122. $^1$H NMR (DMSO-d$_6$, 600 MHz) δ 8.88 (s), 8.11 (s), 7.73-8.05 (m), 7.58 (s), 7.32 (s), 7.13-7.28 (m), 5.43 (s), 5.03-5.21 (br s), 4.87-4.96 (s), 4.85 (s), 4.67 (s), 4.61 (s), 3.89 (s), 3.06 (s), 2.82 (s), 2.65 (s), 2.34-2.46 (m), 2.19 (s), 1.83 (s), 1.69-1.78 (m), 1.61 (s), 1.29 (s). MALDI-MS: calcd. 13,694. Found 13,304.

G4 PAMAM, Conjugated with A$_3$AR Agonist 124 (112)

HATU (4.67 mg, 12.28 μmol) was added to a mixture of compound 124 (6.72 mg, 12.35 mop and dendrimer 123 (2.73 mg, 12.28 mmol) in dry DMF (0.5 mL), then DIPEA (2.15 μL, 12.22 mol) was added. The reaction mixture was stirred at room temperature overnight, extensively dialyzed with water, then lyophilized to yield compound 112 (5.5 mg, 61%). $^1$H NMR (DMSO-d$_6$, 400 MHz) δ 8.46 (br s), 8.10 (s), 7.79-7.93 (m), 7.60 (s), 7.27-7.36 (m), 5.45 (s), 4.67-4.93 (m), 3.87 (s), 3.08 (s), 2.86 (s), 2.66 (s), 2.41 (s), 2.19 (s), 1.78 (s), 1.61 (s), 1.23 (t, J=24 Hz), 0.80-0.89 (m). MALDI-MS: calcd. 47,495. Found 47,985.

Imidazole-1-sulfonyl azide hydrochloride (126)

A modification of a published procedure was used (19). A suspension of 6.53 g NaN$_3$ (25, 100 mmol, Aldrich, >99.5%) and 100 mL acetonitrile (Aldrich, 99.8% anhydrous) in a 500-mL round-bottom flask was cooled in an ice water bath under a flow of nitrogen. Then was added 8.15 mL sulfuryl chloride (100 mmol, TCI American, >98.0%) in 20 mL anhydrous acetonitrile drop-wise to the ice-cooled suspension. The mixture was stirred overnight at room temperature, after which we cooled the white suspension to –0° C. with ice water and added 13.03 g imidazole (191 mmol, TCI America, >98.0%). The resulting white slurry was warmed to room temperature, then stirred for 3 h. It was diluted with ethyl acetate (200 mL) and separated and discarded the aqueous layer. The organic layer was washed twice with deionized water (2×100 mL), then twice with saturated aqueous NaHCO$_3$ (2×100 mL). It was dried over anhydrous MgSO$_4$ overnight and filtered. Ethanolic HCl solution (196 mmol) was added drop-wise to the filtrate while stirring at ice-water temperature. After the addition of –3 mL, a large amount of white solid appeared. The mixture was kept in an ice bath for 15 min, then at room temperature for 30 min, after which it was filtered. The filter cake was washed with ethyl acetate (3×100 mL) to obtain 126 as a colorless solid (8.65 g, 49.9%), m.p. 99-101° C. IR (KBr) 2173, 1383 and 1160 cm$^{-1}$. $^1$H NMR (500 MHz, D$_2$O) δ 7.61 (dd), 8.02 (dd), 9.39 (dd); $^{13}$C NMR (125. MHz, D$_2$O) δ=120.0, 123.5, 137.6. Element Analysis Calculated C, 17.19; H, 1.92; N, 33.41. Found: C, 17.38; H, 1.98; N, 32.97.

Synthesis of Fully Azido-Derivatized PAMAM (G4) (113)

Anhydrous methanol (10 mL, Aldrich, >99.8%) and 18.15 g G4 PAMAM dendrimer (123, Dendritech, 14.93 w/w % in methanol, [NH$_2$]=12.2 mmol) were added to a 250-mL round-bottom flask. 3.12 g K$_2$CO$_3$ (Aldrich, >99.0%, 22.6 mmol) and 31.4 mg CuSO$_4$.5H$_2$O (Aldrich, 98.0%, 0.126 mmol) were then added, causing the solution to take on a pale bluish color. 2.73 g imidazole-1-sulfonyl azide hydrochloride (126, 13.1 mmol) was added to the reaction mixture, and it was stirred at room temperature overnight. The mixture was then dialyzed against deionized water for 7 d, during which the water was changed every 2 h for the first 2 d and thereafter every 4 h. After lyophilization, 2.51 g azide-derivatized G4 dendrimer. The structure was confirmed by HNMR. Element analysis: PAMAM-G4: calculated: C, 52.81; H, 8.48; N, 24.70, O, 14.01; fully azide-derivatized G4 PAMAM calculated: C, 47.03; H, 7.15; N, 33.31, O, 12.49. Found: C, 49.91; H, 7.55; N, 28.07, O: 13.12. The element analyses indicated that 98.0% of primary amines were replaced with azides.

Synthesis of Partially Azido-Derivatized PAMAM (G4) (105)

Anhydrous methanol (5 mL, Aldrich, >99.8%) and 5.13 g G4 PAMAM dendrimer (123, Dendritech, 14.93 w/w % in methanol, [NH$_2$]=3.45 mmol) were added to a 100-mL round-bottom flask. 0.803 g K$_2$CO$_3$ (Aldrich, >99.0%, 5.81 mmol) and 17.2 mg CuSO$_4$.5H$_2$O (Aldrich, 98.0%, 0.069 mmol) were then added; the solution took on a pale-bluish color. 0.43 g imidazole-1-sulfonyl azide hydrochloride (126, 2.05 mmol) was added to the reaction mixture, which was stirred at room temperature overnight. The mixture was then dialyzed against deionized water for 7 d, changing the water every 2 h during the first 2 d and every 4 h thereafter. After lyophilization, 0.45 g partially azide-derivatized G4 dendrimer was collected. Elemental analysis of the partially azide-derivatized G4 PAMAM found C, 49.91; H, 7.55; N, 28.07; O: 13.12. Results of the element analysis were compared with the composition of the G4 PAMAM dendrimer and found that 47.2% of the primary amines were replaced with azides, corresponding to ~31 amines per dendrimer in 64 terminal positions.

Example 4

This example illustrates some of the properties of compounds in accordance with an embodiment of the invention.
Biological Methods: P2Y$_{14}$ Receptor
Materials.
3-isobutyl-1-methyl-xanthine was purchased from Sigma-Aldrich and [$^3$H]adenine from American Radiolabeled Chemicals (St. Louis, Mo.). All cell culture medium and serum were obtained from Gibco (Invitrogen, Carlsbad, Calif.).
Cell Culture.
C6 glioma cells were generated stably expressing the human P2Y$_{14}$—R(P2Y$_{14}$—C6 cells) as previously described by Fricks et al. (35). P2Y$_{14}$—C6 cells were cultured in Dulbecco's modified Eagle's medium (DMEM) supplemented with 5% fetal bovine serum, 1% Geneticin (Gibco BRL Life Technologies, Inc.), and 1% antibiotic-antimocotic (Gibco) at 37° C. in a 5% CO$_2$ environment.
Accumulation of adenosine 3',5'-cyclic phosphate (cAMP).
P2Y$_{14}$—C6 cells were grown in 24-well plates and incubated them with 1 mCi [$^3$H]adenine/well in serum-free DMEM for at least 2 h prior to assay. The assays were initiated by adding HEPES-buffered, serum-free DMEM containing 200 mM 3-isobutyl-1-methyl-xanthine and 30 mM forskolin, with or without drugs, and incubation continued for 15 min at 37° C. Incubations were terminated by aspirating the medium and adding 450 mL ice-cold 5% trichloroacetic acid. [$^3$H]cAMP was isolated by sequential Dowex and alumina chromatography and quantified by liquid scintillation counting as previously described by Harden et al. (20).
Data Analysis.
The concentrations of the dendrimer-ligand complexes were measured by the concentration of the dendrimer, not the attached ligand. EC$_{50}$ and apparent K$_i$ values were determined with Prism software (GraphPad, San Diego, Calif.); they are presented as mean±SE. The number of nucleoside moieties on a given dendrimer that are accessible to receptors is uncertain; the data are therefore shown as apparent K$_i$ values. All experiments were repeated at least three times.
Biological Methods: ARs
Receptor-Binding and Functional Assays.
[$^3$H]adenosine-5'-N-methyluronamide ([$^3$H]NECA, 42.6 Ci/mmol) was obtained from PerkinElmer Life and Analytical Science (Boston, Mass.). [$^3$H](2-[p-(2-carboxyethyl)phenyl-ethylamino]-5'-N-ethylcarboxamido-adenosine) ([$^3$H]CGS21680, 40.5 Ci/mmol) and [$^{125}$I]N$^6$-(4-amino-3-iodobenzyl)adenosine-5'-N-methyluronamide ([$^{125}$I]I-AB-MECA, 2200 Ci/mmol) were purchased from PerkinElmer. Test compounds were prepared as 5-mM stock solutions in DMSO and stored frozen at −20° C.
Cell Culture and Membrane Preparation.
Chinese hamster ovary (CHO) cells were generated by stably expressing the recombinant hA$_1$ and hA$_3$ and human embryonic kidney (HEK) 293 cells stably expressing the hA$_{2A}$AR in DMEM and F12 (1:1) supplemented with 10% fetal bovine serum, 100 units/mL penicillin, 100 µg/mL streptomycin, and 2 µmol/mL glutamine. 800 µg/mL Geneticin were added to the A$_{2A}$ media and 500 µg/mL hygromycin to the A$_1$ and A$_3$ media. After harvesting the cells, they were homogenized with an electric homogenizer for 10 sec, pipetted them into 1-mL vials, and then stored them at −80° C. until the binding experiments were conducted. The protein concentration was measured with a BCA Protein Assay Kit from Pierce Biotechnology (Rockford, Ill.).
Binding Assays.
Each tube in the binding assay contained 50 µL of increasing concentrations of the test ligand in Tris-HCl buffer (50 mM, pH 7.5) containing 10 mM MgCl$_2$, 50 µL of the appropriate agonist radioligand, and 100 µL membrane suspension, added sequentially. For the A$_1$-AR (20 µg protein/tube), the radioligand [$^3$H]NECA was used (~3.5 nM, precise final concentration is calculated for each experiment). For the A$_{2A}$AR (20 µg/tube), the radioligand [$^3$H]CGS21680 was used (~10 nM). For the A$_3$AR (21 µg/tube), the radioligand [$^{125}$I]I-AB-MECA (~0.3 nM) was used. Nonspecific binding was determined with a final concentration of 10 µM unlabeled NECA diluted with the buffer. The mixtures were incubated at 25° C. for 60 min in a shaking water bath. The binding reactions were terminated by filtration through Brandel GF/B filters under a reduced pressure with a M-24 cell harvester (Brandel, Gaithersburg, Md.). Filters were washed three times with 3 mL 50-mM ice-cold Tris-HCl buffer (pH 7.5). The filters were then placed for A$_1$ and A$_{2A}$AR binding in scintillation vials containing 5 mL Hydrofluor scintillation buffer and counted with a PerkinElmer Liquid Scintillation Analyzer (Tri-Carb 2810TR). The filters were counted for A$_3$AR binding with a Packard Cobra II γ-counter (PerkinElmer). The K$_i$ values were determined with GraphPad Prism for all assays.
Accumulation of cAMP.
To determine cAMP production, protein kinase A was incubated with [$^3$H]cAMP (2 nM) in K$_2$HPO$_4$/EDTA buffer (K$_2$HPO$_4$, 150 mM; EDTA, 10 mM), 204 cell lysate, and 30 µL 0.1 M HCl or 50 µL cAMP solution (0-16 µmol/200 µL for standard curve). Bound radioactivity was separated by rapid filtration through Whatman GF/C filters and washed the filters once with cold buffer. Bound radioactivity was measured with liquid scintillation spectrometry.

TABLE 3
Potency of a series of nucleoside-dendrimer conjugates at three subtypes of human ARs.
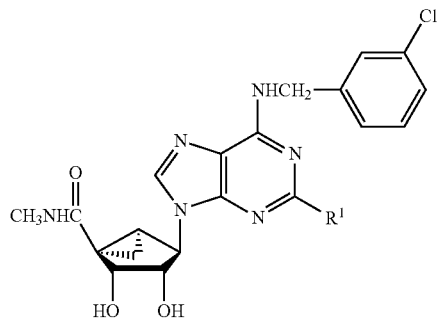
102, 103a, 104b
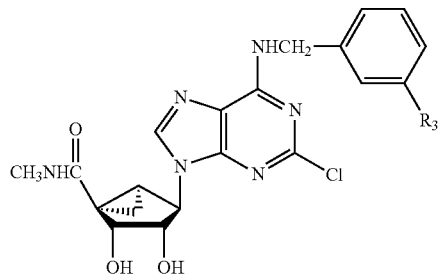
104c
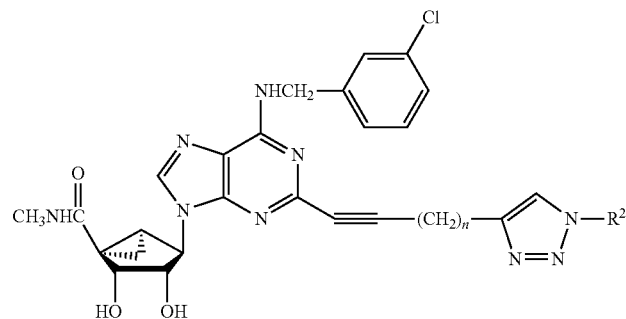
104a, 105-112
| Compd | Structure, $R^1$, $R^2$, or $R^3$ | Affinity ($K_i$, nM) or % inhibition[a] | | |
|---|---|---|---|---|
| | | $A_1$ | $A_{2A}$ | $A_3$ |
| Model compounds | | | | |
| 101[b] IB-MECA | | 51 | 2900 | 1.8 |
| 102[b,c] | $R^1$ = Cl | 260 ± 60[h] | 2300 ± 100 | 0.29 ± 0.04 |
| 103a[b,c] | $R^1$ = C C(CH$_2$)$_4$C CH | (31 ± 2%) at 10 μM | 7040 ± 1430 | 29.4 ± 9.8 |
| 104a[b,c] | $R^2$ = (CH$_2$)$_2$NHCOCH$_3$ | (12 ± 4%) at 10 μM | 2440 ± 320 | 22.3 ± 1.6 |
| 104b[b] | $R^1$ = C≡C(CH$_2$)$_2$CH$_3$ | 1040 ± 80 | (80%) at 10 μM | 0.82 ± 0.20 |

TABLE 3-continued

| | | | | |
|---|---|---|---|---|
| 104c[b] | $R^3 = C \equiv C(CH_2)_4CONH(CH_2)_2NHCOCH_3$ | 181 ± 22 | (80%) at 10 μM | 228 ± 0.54 |

Dendrimer derivatives

| | | | | |
|---|---|---|---|---|
| 105[d] | G4 dendrimer with $(NH_2)_{32}$ and $(N_3)_{32}$ | NA | NA | NA |
| 106[c] | Dendrimer conjugate structure | 22.6 ± 6.9 | 32.2 ± 6.4 | 0.14 ± 0.09 |
| 107[c] | Dendrimer conjugate structure | 35.1 ± 7.5 | 34.4 ± 1.8 | 0.32 ± 0.03 |
| 108[c] | Dendrimer conjugate structure | 78 ± 31 | 584 ± 48 | 39.5 ± 11.8 |
| 109 | Dendrimer conjugate structure | ND | (27 ± 7%) at 10 μM | 31.4 ± 2.8 |

TABLE 3-continued

| # | Structure | | | |
|---|---|---|---|---|
| 110 | (compound with NHCH₂-phenyl-alkyne, (CH₂)₃—CONH—(CH₂)₂—NHCO—G2.5, (CO₂H)₂₇, n=5) | 77 | (3 ± 2%) at 1 μM | 41.7 ± 6.4 |
| 111[c] | (compound with NHCH₂-phenyl-alkyne, (CH₂)₃—CONH—G3, (NH₂)₁₉, n=13) | 7.1 | 5750 ± 1600 | 17.6 ± 2.8 |
| 112 | (compound with 3-Cl-benzyl NHCH₂, alkyne-(CH₂)₂—CONH—G4, n=64) | 1.92 ± 1.25 | 727 ± 168 | 11.8 ± 2.2 |

[a]All experiments were done on CHO or HEK293 (A$_{2A}$ only) cells stably expressing one of four subtypes of human ARs. The binding affinity for A$_1$, A$_{2A}$, and A$_3$ARs was expressed as K$_i$ values (n = 3-5) and was determined by using agonist radioligands ([$^3$H]NECA, [$^3$H]CGS21680, or [$^{125}$I]I-AB-MECA, respectively), unless noted. A percentage in parentheses refers to inhibition of radioligand binding at the indicated concentration. The concentrations of the dendrimer-ligand complexes were measured by the concentration of the dendrimer, not the ligand. Therefore, all binding K$_i$ values of dendrimers are expressed as K$_{iapp}$ values.
[b]Affinity values from Tosh et al. and Melman et al., Bioorg. Med. Chem. Lett., 18, 2813-2819.
[c]102, MRS3558; 103a, MRS5221; 104a, MRS5233; 106, MRS5246; 107, MRS5247; 108, MRS5259; 111, MRS5216.
[d]Compound 105 is a dendrimer precursor of 108 and is similar to the dendrimer precursor of 106 and 107.
NA—not active in inhibition of radioligand binding (<10%) at 1 μM.

TABLE 4

Maximal efficacy of (N)-methanocarba adenosine derivatives in a functional assay at the A$_3$AR.

| Compound | Concentration (μM) | % Inhibition of cAMP accumulation[a] at the hA$_3$AR |
|---|---|---|
| IB-MECA | 1.0 | 99 ± 6 |
| Cl-IB-MECA | 1.0 | 97 |
| NECA | 1.0 | 100 |
| 103a | 10 | 60.2 ± 17.0 |
| 104a[b] | 10 | 93.6 ± 17.7 |
| 105 | 1.0 | 1.7 ± 1.4 |
| 106 | 0.1 | 98.7 ± 14.3 |
| 107 | 0.1 | 91.4 ± 20.2 |
| 108 | 0.1 | 111 ± 20 |
| 109[c] | 1.0 | 88.2 ± 15.1 |
| 110 | 1.0 | 91.3 ± 12.3 |
| 111 | 1.0 | 101 ± 10 |
| 112 | 0.1 | 92.1 ± 21.2 |

[a]The efficacy at the human A$_3$AR was determined by inhibition of forskolin-stimulated cyclic AMP production in AR-transfected CHO cells, as described in the text. Percent inhibition is shown at the indicated concentration, in comparison to the maximal effect of a full agonist NECA at 1 μM. Data are expressed as mean ± standard error (n = 3-5). ND, not determined.
[b]Values from Tosh et al.

EC$_{50}$ values were determined with full curves for compounds 107 (0.12±0.03 nM), 108 (1.36 nM), and 111 (2.93±0.37 nM). FIGS. 19-23 show additional conjugates and their binding affinities to adenosine receptors.

Example 5

This example illustrates the synthesis of compounds in accordance with an embodiment of the invention. See FIGS. 24-27 for reaction schemes illustrating the synthesis.

(1S,2R,3S,4R,5S)-4-[2-Chloro-6-{3-(1,6-heptadiynylbenzylamino)}-9H-purin—9-yl]-2,3-dihydroxybicyclo[3.1.0]hexane-1-carboxylic acid N-methylamide (200)

To a solution of compound 127 (50 mg, 0.09 mmol) in anhydrous DMF (2 mL), $PdCl_2(PPh_3)_2$ (12.6 mg, 0.01 mmol), CuI (1.7 mg, 0.008 mmol), 1,6-heptadiyne (0.1 mL, 0.9 mmol) and then triethylamine (0.12 mL, 0.89 mmol) were added and stirred overnight at room temperature. Solvent was evaporated under vacuum, and the residue was purified on flash silica gel column chromatography ($CH_2Cl_2$:MeOH=60:1) to give compound 200 (38 mg, 81%) as syrup. $^1$H NMR ($CDCl_3$, 400 MHz) δ 7.8 (s, 1H), 7.42 (s, 1H), 7.24-7.30 (m, 3H), 5.03 (d, J=6.0 Hz, 1H), 4.84 (s, 1H), 4.79 (br s, 1H), 4.13 (d, J=6.4 Hz, 1H), 2.94 (s, 3H), 2.55 (t, J=7.2 Hz, 2H), 2.36-2.41 (m, 2H), 2.18-2.22 (m, 1H), 2.00 (t, J=2.8 Hz, 1H), 1.68 (t, J=9.2 Hz, 1H), 1.85-1.79 (m, 2H), 1.37-1.41 (m, 1H). HRMS calculated for $C_{27}H_{28}ClN_6O_3$ $(M+H)^+$: 519.1911. Found 519.1930.

(1S,2R,3S,4R,5S)-4-[2-Chloro-6-{3-(1,7-octadiynyl)benzylamino}-9H-purin-9-yl]-2,3-dihydroxybicyclo[3.1.0]hexane-1-carboxylic acid N-methylamide (201)

Compound 201 (85%) was synthesized from compound 127 and 1,7-octadiyne following the same procedure as for compound 200. $^1$H NMR ($CD_3OD$, 400 MHz) δ 8.04 (s, 1H), 7.40 (s, 1H), 7.26-7.34 (m, 3H), 5.08 (d, J=6.8 Hz, 1H), 4.81 (s, 1H), 4.73 (br s, 2H), 4.60 (br s, 2H), 4.01 (d, J=6.4 Hz, 1H), 2.87 (s, 3H), 2.43 (t, J=6.8 Hz, 2H), 2.21-2.26 (m, 2H), 2.05-2.08 (m, 1H), 1.68-1.71 (m, 1H), 1.38-1.40 (m, 1H). HRMS calculated for $C_{28}H_{30}ClN_6O_3$ $(M+H)^+$: 533.2068. Found 533.2070.

(1S,2R,3S,4R,5S)-4-[2-Chloro-6-{3-(1,8-nonadiynyl)}-9H-purin-9-yl]-2,3-dihydroxybicyclo[3.1.0]hexane-1-carboxylic acid N-methylamide (202)

Compound 202 (79%) was synthesized from compound 127 and 1,8-nonadiyne following the same procedure as for compound 200. $^1$H NMR ($CDCl_3$, 400 MHz) δ 7.92 (s, 1H), 7.43 (s, 1H), 7.25-7.32 (m, 3H), 5.10 (d, J=6.6 Hz, 1H), 4.85 (s, 1H), 4.78 (br s, 2H), 4.15 (d, J=6.3 Hz, 1H), 2.93 (s, 3H), 2.42 (t, J=6.0 Hz, 2H), 2.22-2.23 (m, 2H), 1.97 (t, J=2.8 Hz, 1H), 1.71-1.78 (m, 2H), 1.58-1.61 (m, 6H), 1.48-1.52 (m, 1H). HRMS calculated for $C_{29}H_{32}ClN_6O_3$ $(M+H)^+$: 547.2224. Found 547.2239.

(1S,2R,3S,4R,5S)-4-(2-Chloro-6-(3-(5-(1-(4-fluoro-3-nitrophenyl)-1H-1,2,3-triazol-4-yl)pent-1-ynyl)benzylamino)-9H-purin-9-yl)-2,3-dihydroxybicyclo[3.1.0]hexane-1-carboxylic acid-N-methylamide (203)

4-Fluoro-3-nitro-phenylazide (9.3 mg, 0.051 mmol) and the click catalyst TBTA (36) (1 mg, 0.001 mmol) were added to a solution of compound 200 (19 mg, 0.036 mmol) in t-butanol (0.6 mL)-$CH_2Cl_2$ (0.6 mL)-water (0.6 mL) at room temperature. Freshly prepared 1M solution of sodium ascorbate (36.6 µL) followed by 7.5% solution of copper sulfate (60.7 µL, 0.018 mmol) was also added into the reaction mixture and stirred at room temperature overnight. Solvent was evaporated, and the residue was purified on flash silica gel column chromatography ($CH_2Cl_2$:MeOH=40:1) to give compound 203 (23 mg, 90%) as a syrup. $^1$H NMR ($CD_3OD$, 400 MHz) δ 8.53-8.62 (m, 1H), 8.49 (s, 1H), 8.22-8.19 (m, 1H), 8.04 (s, 1H), 7.60-7.67 (m, 2H), 7.39-23 (m, 3H), 5.05 (d, J=5.6 Hz, 1H), 4.81 (s, 1H), 4.71 (br s, 2H), 4.00 (d, J=6.8 Hz, 1H), 2.98 (t, J=7.6 Hz, 2H), 2.86 (s, 3H), 2.53 (t, J=6.8 Hz, 2H), 2.02-2.08 (m, 3H), 1.82 (t, J=4.8 Hz, 1H), 1.36-1.39 (m, 1H). HRMS calculated for $C_{33}H_{31}ClFN_8O_3$ $(M+H)^+$: 701.2151. Found 701.2175.

(1S,2R,3S,4R,5S)-4-(2-Chloro-6-(3-(6-(1-(4-fluoro-3-nitrophenyl)-1H-1,2,3-triazol-4-yl)hex-1-ynyl)benzylamino)-9H-purin-9-yl)-2,3-dihydroxybicyclo[3.1.0]hexane-1-carboxylic acid-N-methylamide (204)

Compound 204 (94%) was synthesized from compound 201 following the same procedure as for compound 203. $^1$H NMR ($CD_3OD$, 400 MHz) δ 8.65-8.58 (m, 1H), 8.45 (s, 1H), 8.23-8.19 (m, 1H), 8.03 (s, 1H), 7.65 (t, J=8.8 Hz, 1H), 7.41 (s, 1H), 7.33-7.25 (m, 2H), 5.07 (d, J=6.8 Hz, 1H), 4.80 (s, 1H), 4.72 (br s, 2H), 4.00 (d, J=6.8 Hz, 1H), 2.87 (s, 3H), 2.51 (t, J=6.8 Hz, 2H), 2.07-2.04 (m, 1H), 1.97-1.91 (m, 2H), 1.82 (t, J=5.2 Hz, 2H), 1.74-1.69 (m, 2H), 1.39-1.35 (m, 1H). HRMS calculated for $C_{34}H_{33}ClFN_{10}O_5$ $(M+H)^+$: 715.2308. Found 715.2302.

(1S,2R,3S,4R,5S)-4-(2-Chloro-6-(3-(7-(1-(4-fluoro-3-nitrophenyl)-1H-1,2,3-triazol-4-yl)hept-1-ynyl)benzylamino)-9H-purin-9-yl)-2,3-dihydroxybicyclo[3.1.0]hexane-1-carboxylic acid-N-methylamide (205)

Compound 205 (96%) was synthesized from compound 202 following the same procedure as for compound 203. $^1$H NMR ($CD_3OD$, 400 MHz) δ 8.55-8.59 (m, 1H), 8.41 (s, 1H), 8.16-8.12 (m, 1H), 8.03 (s, 1H), 7.60 (t, J=9.2 Hz, 1H), 7.36 (s, 1H), 7.30-7.20 (m, 2H), 5.08 (d, J=6.4 Hz, 1H), 4.80 (s, 1H), 4.69 (br s, 2H), 4.01 (d, J=6.4 Hz, 1H), 2.87-2.82 (m, 5H), 2.44 (t, J=6.4 Hz, 2H), 2.08-2.05 (m, 1H), 1.84-1.81 (m, 3H), 1.68-1.58 (m, 4H), 1.39-1.38 (m, 1H). HRMS calculated for $C_{35}H_{35}ClFN_{10}O_5$ $(M+H)^+$: 729.2464. Found 729.2463.

(1S,2R,3S,4R,5S)-4-(2-Chloro-6-(3-(6-(1-(adamantyl)-1H-1,2,3-triazol-4-yl)hex-1-ynyl)benzylamino)-9H-purin-9-yl)-2,3-dihydroxybicyclo[3.1.0]hexane-1-carboxylic acid-N-methylamide (206)

Compound 206 (93%) was synthesized from compound 201 following the same procedure as for compound 203. $^1$H NMR ($CD_3OD$, 400 MHz) δ 8.04 (s, 1H), 7.40 (s, 1H), 7.35-7.26 (m, 3H), 5.09 (d, J=6.8 Hz, 1H), 4.82 (s, 1H), 4.73 (s, 2H), 4.02 (d, J=6.8 Hz, 1H), 2.87 (s, 1H), 2.44 (t, J=6.8 Hz, 2H), 2.26-2.21 (m, 3H), 2.17 (m, 8H), 2.08-2.05 (m, 1H), 1.82 (t, J=4.8 Hz, 1H), 1.70-1.69 (m, 10H), 1.39-1.36 (m, 1H), 0.94-0.88 (m, 1H). HRMS calculated for $C_{38}H_{45}ClN_9O_3$ $(M+H)^+$: 710.3257. Found 710.3248.

(1S,2R,3S,4R,5S)-4-(2-Chloro-6-(3-(5-(1-(4-fluoro-3-amino-phenyl)-1H-1,2,3-triazol-4-yl)pent-1-ynyl)benzylamino)-9H-purin-9-yl)-2,3-dihydroxybicyclo[3.1.0]hexane-1-carboxylic acid-N-methylamide (207)

Zinc dust (3 mg, 0.045 mmol) was added to a solution of compound 203 (5 mg, 0.007 mmol) in acetonitrile (0.5 mL)- acetic acid (0.5 mL) at 0° C. After addition, the reaction mixture was brought to room temperature and stirred for 2 h under the same conditions. The reaction mixture was filtered on a Celite bed, and the filtrate was evaporated under vacuum. The residue was purified on flash silica gel column chromatography ($CH_2Cl_2$: MeOH=20:1) to give compound 207 (3 mg, 62%). $^1$H NMR ($CD_3OD$, 400 MHz) δ 8.65-8.58 (m, 1H), (1S,2R,3S,4R,5S)-4-(2-Chloro-6-(3-(7-(1-(4-fluoro-3-amino-phenyl)-1H-1,2,3-triazol-4-yl)hept-1-ynyl) benzylamino)-9H-purin-9-yl)-2,3-dihydroxybicyclo [3.1.0]hexane-1-carboxylic acid-N-methylamide (208)

Compound 208 (64%) was synthesized from compound 205 following the same procedure as for compound 207. $^1$H NMR ($CD_3OD$, 400 MHz) δ 8.12 (s, 1H), 8.03 (s, 1H), 7.38 (s, 1H), 7.32-7.21 (m, 4H), 7.06-7.02 (m, 1H), 6.90-6.86 (m, 1H), 5.08 (d, J=7.2 Hz, 1H), 4.80 (s, 1H), 4.70 (br s, 2H), 4.01 (d, J=6.4 Hz, 1H), 2.87 (s, 3H), 2.80 (t, J=7.2 Hz, 2H), 2.44 (t, J=6.8 Hz, 2H), 2.02-2.09 (m, 1H), 1.83-1.78 (m, 2H), 1.68-1.54 (m, 5H), 0.89-0.93 (m, 1H). HRMS calculated for $C_{40}H_{37}ClFN_8O$ (M+H)$^+$: 699.2763. Found 699.2745.

(1R,2R,3S,4R,5S)-4-(2-Chloro-6-(3-(hepta-1,6-diynyl)benzylamino)-9H-purin-9-yl) 2,3-O-isopropylidine-bicyclo[3.1.0]hexane (209)

$PdCl_2(PPh_3)_2$ (29.7 mg, 0.04 mmol), CuI (8.0 mg, 0.04 mmol), and 1,6-heptadiyne (0.24 mL, 2.11 mmol) followed by triethylamine (60 μL, 0.41 mmol) were added to a solution of (1R,2R,3S,4R,5S)-4-(2-chloro-6-(3-iodobenzylamino)-9H-purin-9-yl) 2,3-O-isopropylidine-bicyclo[3.1.0]hexane (114 mg, 0.211 mmol) in anhydrous DMF (2 mL), and the reaction mixture was stirred overnight at room temperature. Solvent was evaporated under vacuum, and the residue was purified on flash silica gel column chromatography (hexane: ethyl acetate=2:1) to give compound 209 (83 mg, 78%) as foamy syrup. $^1$H NMR ($CDCl_3$, 400 MHz) δ 7.72 (s, 1H), 7.42 (s, 1H), 7.28-7.42 (m, 3H), 6.31 (br s, 1H), 5.35 (t, J=6.0 Hz, 1H), 4.98 (s, 1H), 4.81 (br s, 2H), 4.65 (d, J=7.6 Hz, 1H), 2.55 (t, J=7.2 Hz, 2H), 2.38 (dd, $J_1$=2.8 Hz, $J_2$=3.2 Hz, 2H), 2.08-2.14 (m, 1H), 1.99 (t, J=2.8 Hz, 1H), 1.82-1.85 (m, 2H), 1.64-1.67 (m, 2H), 1.56 (s, 3H), 1.26 (s, 3H), 0.93-1.00 (m, 1H). HRMS calculated for $C_{28}H_{29}ClN_5O_2$ (M+H)$^+$: 502.2032. Found 502.2029.

(1R,2R,3S,4R,5S)-4-(2-Chloro-6-(3-(nona-1,8-diynyl)benzylamino)-9H-purin-9-yl) 2,3-O-isopropylidene-bicyclo[3.1.0]hexane (210)

Compound 21 (80%) was synthesized from (1R,2R,3S,4R, 5S)-4-(2-chloro-6-(3-iodobenzylamino)-9H-purin-9-yl) 2,3-O-isopropylidine-bicyclo[3.1.0]hexane and 1,8-nonadiyne following the same procedure as for compound 209. $^1$H NMR ($CDCl_3$, 400 MHz) δ 7.71 (s, 1H), 7.42 (s, 1H), 7.27-7.34 (m, 3H), 6.33 (br s, 1H), 5.35 (t, J=6.4 Hz, 1H), 4.98 (s, 1H), 4.80 (br s, 2H), 4.64 (d, J=7.2 Hz, 1H), 2.41 (t, J=3.6 Hz, 2H), 2.28-2.21 (m, 3H), 2.14-2.08 (m, 1H), 1.97-1.96 (t, J=2.8 Hz, 1H), 1.54-1.68 (m, 10H), 1.26 (s, 3H), 0.88-0.99 (m, 1H). HRMS calculated for $C_{30}H_{33}ClN_5O_2$ (M+H)$^+$: 530.2323. Found 530.2315.

(1R,2R,3S,4R,5S)-4-(2-Chloro-6-(3-(hepta-1,6-diynyl)benzylamino)-9H-purin-9-yl) bicyclo[3.1.0]hexane-2,3-diol (211)

A solution of compound 209 (92 mg, 0.18 mmol) in $CH_2Cl_2$ (4 mL) and trifluoromethane sulfonic acid-water (2:1), (3 mL) was stirred at room temperature overnight. Solvent was evaporated, and the residue was purified on flash silica gel chromatography ($CH_2Cl_2$:MeOH=70:1) to give compound 211 (77 mg, 92%) as a syrup. $^1$H NMR ($CDCl_3$, 400 MHz) δ 7.80 (s, 1H), 7.42 (s, 1H), 7.29-7.35 (m, 3H), 6.41 (br s, 1H), 4.87 (s, 1H), 4.81 (br s, 2H), 4.02 (d, J=6.4 Hz, 1H), 4.00 (s, 1H), 2.69 (d, J=6.3 Hz, 1H), 2.56 (t, J=6.8 Hz, 2H), 2.36-2.41 (m, 2H), 2.03-2.08 (m, 1H), 2.00 (t, J=2.8 Hz, 1H), 1.85-1.82 (m, 2H), 1.68-1.64 (m, 1H), 1.26-1.30 (m, 2H), 0.90-0.80 (m, 1H). HRMS calculated for $C_{25}H_{25}ClN_5O_2$ (M+H)$^+$: 462.1697. Found 462.1696.

(1R,2R,3S,4R,5S)-4-(2-Chloro-6-(3-(octa-1,7-diynyl)benzylamino)-9H-purin-9-yl) bicyclo[3.1.0]hexane-2,3-diol (212)

$PdCl_2(PPh_3)_2$ (5.7 mg, 0.008 mmol), CuI (1.0 mg, 0.005 mmol), and 1,7-octadiyne (27 μL, 0.2 mmol) followed by triethylamine (57 pt, 0.4 mmol) were added to a solution of compound (1R,2R,3S,4R,5S)-4-(2-chloro-6-(3-iodobenzylamino)-9H-purin-9-yl) 2,3-O-isopropylidine-bicyclo[3.1.0] hexane (20.4 mg, 0.04 mmol) in anhydrous DMF (1.2 mL) and the reaction mixture was stirred overnight at room temperature. Solvent was evaporated under vacuum, and the residue was roughly purified on flash silica gel column chromatography and the obtained product was dissolved in $CH_2Cl_2$ (3 mL) and 2 mL of trifluoromethane sulfonic acid-water (2:1) were added into it and stirred at room temperature overnight. Solvent was evaporated, and the residue was purified on flash silica gel chromatography ($CH_2Cl_2$:MeOH=60: 1) to give compound 212 (12.6 mg, 70%) as a syrup. $^1$H NMR ($CDCl_3$, 400 MHz) δ 7.80 (s, 1H), 7.42 (s, 1H), 7.35-7.29 (m, 3H), 6.43 (br s, 1H), 4.88 (s, 1H), 4.80 (br s, 2H), 4.03 (d, J=7.2 Hz, 1H), 3.97 (s, 1H), 2.64 (m, 1H), 2.45 (t, J=6.4 Hz, 2H), 2.29-2.26 (m, 3H), 2.08-2.06 (m, 1H), 1.98 (t, J=2.4 Hz, 1H), 1.71-1.66 (m, 3H), 1.28-1.31 (m, 1H), 0.86-0.82 (m, 1H). HRMS calculated for $C_{26}H_{27}ClN_5O_2$ (M+H)+$^+$: 476.1853. Found 476.1869.

(1R,2R,3S,4R,5S)-4-(2-Chloro-6-(3-(nona-1,8-diynyl)benzylamino)-9H-purin-9-yl) bicyclo[3.1.0]hexane-2,3-diol (213)

Compound 213 (89%) was synthesized from compound 210 following the same procedure as for compound 211. $^1$H NMR ($CD_3OD$, 400 MHz) δ 8.15 (s, 1H), 7.40 (s, 1H), 7.26-7.33 (m, 3H), 4.80 (s, 1H), 4.74-4.69 (m, 1H), 4.60 (br s, 2H), 3.92 (d, J=6.4 Hz, 1H), 2.41 (t, J=6.4 Hz, 2H), 2.18-2.19 (m, 3H), 2.01-1.96 (m, 1H), 1.70-1.65 (m, 1H), 1.59-1.50 (m, 6H), 1.34-1.30 (m, 1H), 0.80-0.74 (m, 1H). HRMS calculated for $C_{27}H_{29}ClN_5O_2$ (M+H)$^+$: 490.2010. Found 490.2000.

(1R,2R,3S,4R,5S)-4-(2-Chloro-6-(3-(5-(1-(4-fluoro-3-nitrophenyl)-1H-1,2,3-triazol-4-yl)pent-1-ynyl) benzylamino)-9H-purin-9-yl)-bicyclo[3.1.0]hexane-2,3-diol (214)

4-Fluoro-3-nitro-phenylazide (7.5 mg, 0.041 mmol) and TBTA (1 mg, 0.001 mmol) were added to a solution of compound 211 (13.5 mg, 0.029 mmol) in $CH_2Cl_2$-t-butanol (0.6 mL)-water (0.6 mL) at room temperature. Freshly prepared 1M solution of sodium ascorbate (29.2 μL) followed by 7.5% solution of copper sulfate (48 μL, 0.015 mmol) was also added into the reaction mixture stirred at room temperature overnight. Solvent was evaporated, and the residue was purified on flash silica gel column chromatography ($CH_2Cl_2$: MeOH=45:1) to give compound 214 (17 mg, 91%) as a syrup.

¹H NMR (CD₃OD, 400 MHz) δ 861-8.59 (m, 1H), 8.49 (s, 1H), 8.23-8.19 (m, 1H), 8.14 (s, 1H), 7.65 (t, J=9.2 Hz, 1H), 7.39 (s, 1H), 7.33-7.24 (m, 3H), 4.79 (s, 1H), 4.72-4.70 (m, 3H), 3.90 (d, J=6.4 Hz, 1H), 2.99 (t, J=7.6 Hz, 2H), 2.53 (t, J=6.8 Hz, 2H), 2.08-1.96 (m, 3H), 1.69-1.65 (m, 1H), 1.33-1.30 (m, 1H), 0.79-0.75 (m, 1H). HRMS calculated for $C_{31}H_{28}ClFN_9O_4$ (M+H)⁺: 644.1937. Found 644.1962.

(1R,2R,3S,4R,5S)-4-(2-Chloro-6-(3-(6-(1-(4-fluoro-3-nitrophenyl)-1H-1,2,3-triazol-4-yl)hex-1-ynyl) benzylamino)-9H-purin-9-yl)-bicyclo[3.1.0]hexane-2,3-diol (215)

Compound 215 (95%) was synthesized from compound 212 following the same procedure as for compound 214. ¹H NMR (CDCl₃, 400 MHz) δ 8.44-8.39 (m, 1H), 8.07-8.11 (m, 1H), 7.83 (s, 1H), 7.77 (s, 1H), 7.51-7.43 (m, 2H), 7.33-7.26 (m, 3H), 6.58 (br s, 1H), 4.87 (s, 1H), 4.79 (br s, 2H), 4.15 (s, 1H), 4.02 (d, J=6.8 Hz, 1H), 2.89 (t, J=7.6 Hz, 2H), 2.49 (t, J=6.8 Hz, 2H), 2.08-2.04 (m, 1H), 1.96-1.90 (m, 2H), 1.76-1.64 (m, 3H), 1.31-1.28 (m, 1H), 0.79-0.85 (m, 1H). HRMS calculated for $C_{32}H_{30}ClFN_9O_4$ (M+H)⁺: 658.2093. Found 658.2124.

(1R,2R,3S,4R,5S)-4-(2-Chloro-6-(3-(7-(1-(4-fluoro-3-nitrophenyl)-1H-1,2,3-triazol-4-yl)hept-1-ynyl) benzylamino)-9H-purin-9-yl)bicyclo[3.1.0]hexane-2,3-diol (216)

Compound 216 (91%) was synthesized from compound 213 following the same procedure as for compound 214. ¹H NMR (CD₃OD, 400 MHz) δ 8.56-8.54 (m, 1H), 8.40 (s, 1H), 8.13-8.18 (m, 2H), 7.60 (t, J=8.8 Hz, 1H), 7.37 (s, 1H), 7.30 (d, J=6.8 Hz, 1H), 7.24-7.21 (m, 2H), 4.79 (s, 1H), 4.72-4.69 (m, 3H), 3.90 (d, J=6.4 Hz, 1H), 2.84 (t, J=7.2 Hz, 2H), 2.45 (t, J=6.8 Hz, 2H), 2.01-1.95 (m, 1H), 1.86-1.79 (m, 2H), 1.68-1.58 (m, 5H), 1.33-1.30 (m, 1H), 0.82-0.72 (m, 1H). HRMS calculated for $C_{33}H_{32}ClFN_9O_4$ (M+H)⁺: 672.2250. Found 672.2245.

(1S,2R,3S,4R,5S)-Ethyl-4-(2-chloro-6-(prop-2-ynylamino)-9H-purin-9-yl)-2,3-O-isopropylidine-bicyclo[3.1.0]hexane-1-carboxylate (216)

Propargylamine (0.5 mL, 7.5 mmol) and triethylamine (2.1 mL, 15 mmol) were added to a solution of compound 28 (620 mg, 0.14 mmol) in anhydrous methanol (10 mL) and stirred overnight at room temperature. Solvent was evaporated, and the residue was purified on flash silica gel column chromatography (hexane:ethyl acetate=1:1) to give compound 216 (511 mg, 79%) as a syrup. ¹H NMR (CDCl₃, 400 MHz) δ 7.73 (s, 1H), 6.20 (br s, 1H), 5.89 (d, J=7.0 Hz, 1H), 4.88 (s, 1H), 4.74 (d, J=7.1 Hz, 1H), 4.47 (br s, 2H), 4.32-4.28 (m, 2H), 4.27-4.13 (m, 1H), 2.32 (s, 1H), 2.24-2.20 (m, 1H), 1.76-1.72 (m, 1H), 1.68 (s, 3H), 1.57-1.53 (m, 4H), 1.36 (t, J=7.2 Hz, 3H), 1.30-1.25 (m, 1H). HRMS calculated for $C_{20}H_{23}ClN_5O_4$ (M+H)⁺: 432.1367. Found 432.1362.

(1S,2R,3S,4R,5S)-4-(2-Chloro-6-(prop-2-ynylamino)-9H-purin-9-yl)-2,3-O-isopropylidine-N-methyl bicyclo[3.1.0]hexane-1-carboxamide (217)

Methylamine (40% solution, 3 mL) was added to a solution of compound 216 (244 mg, 0.56 mmol) in methanol (9 mL) and stirred for 2 d at room temperature. Solvent was evaporated under vacuum, and the residue was purified on flash silica gel column chromatography (CH₂Cl₂:MeOH=70:1) to give compound 217 (148 mg, 63%) as a syrup. ¹H NMR (CD₃OD, 400 MHz) δ 8.08 (s, 1H), 5.75 (d, J=7.2 Hz, 1H), 4.97 (s, 1H), 4.84 (d, J=6.8 Hz, 1H), 4.35 (br s, 2H), 2.86 (s, 3H), 2.63 (t, J=2.4 Hz, 1H), 2.15-2.11 (m, 1H), 1.57-1.54 (m, 4H), 1.40 (t, J=5.2 Hz, 1H), 1.29 (s, 3H). HRMS calculated for $C_{19}H_{21}ClN_6O_3$ (M+H)⁺: 416.1364. Found 416.1374.

(1S,2R,3S,4R,5S)-4-(2-Chloro-6-(prop-2-ynylamino)-9H-purin-9-yl)-2,3-dihydroxy-N-methylbicyclo[3.1.0]hexane-1-carboxamide (218)

10% Trifluoroacetic acid (3 mL) was added to a solution of compound 217 (70 mg, 0.167 mmol) in methanol (4 mL) and heated at 70° C. overnight. Solvent was evaporated under vacuum, and the residue was purified on flash silica gel column chromatography (CH₂Cl₂:MeOH=40:1) to give compound 218 (55 mg, 87%) as a syrup. ¹H NMR (CD₃OD, 400 MHz) δ 8.06 (s, 1H), 5.09 (d, J=5.6 Hz, 1H), 4.8 (s, 1H), 4.36 (br s, 2H), 4.01 (d, J=6.4 Hz, 1H), 2.88 (s, 3H), 2.63 (t, J=2.4 Hz, 1H), 2.08-2.04 (m, 1H), 1.82 (t, J=4.8 Hz, 1H), 1.40-1.37 (m, 1H). HRMS calculated for $C_{16}H_{18}ClN_6O_3$ (M+H)⁺: 377.1129. Found 377.1124.

(1S,2R,3S,4R,5S)-4-(2-Chloro-6-((1-(4-fluoro-3-nitrophenyl)-1H-1,2,3-triazol-4-yl)methylamino)-9H-purin-9-yl)-2,3-dihydroxy-N-methylbicyclo[3.1.0]hexane-1-carboxamide (219a)

4-Fluoro-3-nitro-phenylazide (9.7 mg, 0.053 mmol) and TBTA (1 mg, 0.001 mmol) were added to a solution of compound 218 (14.4 mg, 0.038 mmol) in t-butanol (0.8 mL)-water (0.8 mL) at room temperature. Freshly prepared 1M solution of sodium ascorbate (38.2 μL) followed by 7.5% solution of copper sulfate (63 μL, 0.019 mmol) was also added into the reaction mixture stirred at room temperature overnight. Solvent was evaporated, and the residue was purified on flash silica gel column chromatography (CH₂Cl₂:MeOH=30:1) to give compound 219a (19 mg, 92%) as a syrup. ¹H NMR (CD₃OD, 400 MHz) δ 8.62-8.61 (m, 2H), 8.27-8.24 (m, 1H), 8.06 (s, 1H), 7.69-7.64 (m, 1H), 5.08 (d, J=6.8 Hz, 1H), 4.94 (br s, 2H), 4.81 (s, 1H), 4.01 (d, J=6.0 Hz, 1H), 2.87 (s, 3H), 2.07-2.04 (m, 1H), 1.82 (t, J=4.8 Hz, 1H), 1.39-1.37 (m, 1H). HRMS calculated for $C_{22}H_{21}ClFN_{10}O_5$ (M+H)⁺: 559.1369. Found 559.1346.

(1S,2R,3S,4R,5S)-4-(2-Chloro-6-((1-(adamantyl)-1H-1,2,3-triazol-4-yl)methylamino)-9H-purin-9-yl)-2,3-dihydroxy-N-methylbicyclo[3.1.0]hexane-1-carboxamide (220)

Compound 220 (95%) was synthesized from compound 218 following the same procedure as for compound 219. ¹H NMR (CD₃OD, 400 MHz) δ 8.04 (s, 1H), 8.03 (s, 1H), 5.08 (d, J=6.8 Hz, 1H), 4.82 (s, 2H), 4.01 (d, J=6.4 Hz, 1H), 2.87 (s, 3H), 2.25 (s, 9H), 2.07-2.04 (m, 1H), 1.84-1.81 (m, 7H), 1.40-1.36 (m, 1H). HRMS calculated for $C_{26}H_{33}ClN_9O_3$ (M+H)⁺: 554.2395. Found 554.2383.

(1R,2R,3R,4R,5S)-4-(2-Chloro-6-(prop-2-ynylamino)-9H-purin-9-yl) 2,3-O-isopropylidene-bicyclo[3.1.0]hexane (221)

Propargylamine (47 μL, 0.7 mmol) and triethylamine (0.28 mL, 1.9 mmol) were added to a solution of compound 34 (50 mg, 0.14 mmol) in anhydrous methanol (2 mL) and stirred overnight at room temperature. Solvent was evaporated, and the residue was purified on flash silica gel column chromatography (hexane:ethyl acetate=1:1) to give compound 221 (45 mg, 85%) as a syrup. $^1$H NMR (CD$_3$OD, 300 MHz) δ 7.80 (s, 1H), 6.25 (br s, 1H), 5.34 (t, J=5.7 Hz, 1H), 4.98 (s, 1H), 4.64 (d, J=7.2 Hz, 1H), 4.48 (s, 2H), 2.03-2.12 (m, 1H), 1.78 (s, 1H), 1.62-1.67 (m, 1H), 1.54 (s, 3H), 1.25 (s, 3H), 0.88-0.98 (m, 2H). HRMS calculated for C$_{17}$H$_{19}$ClN$_5$O$_2$ (M+H)$^+$: 360.1227. Found 360.1218.

(1R,2R,3S,4R,5S)-4-(2-Chloro-6-(prop-2-ynylamino)-9H-purin-9-yl) bicycle[3.1.0]hexane-2,3-diol (222)

A solution of compound 221 (40 mg, 0.11 mmol) in methanol (3 mL) and 10% trifluoromethane sulfonic acid-water (3 mL) was heated at 70° C. overnight. Solvent was evaporated, and the residue was purified on flash silica gel chromatography (CH$_2$Cl$_2$:MeOH=50:1) to give compound 222 (33 mg, 93%) as a syrup. $^1$H NMR (CD$_3$OD, 300 MHz) δ 8.15 (s, 1H), 4.79 (s, 1H), 4.70 (t, J=6.0 Hz, 1H), 4.36 (s, 2H), 3.89 (d, J=6.6 Hz, 1H), 2.62 (s, 1H), 1.95-2.01 (m, 1H), 1.62-1.68 (m, 1H), 1.28-1.32 (m, 1H), 0.72-0.79 (m, 1H). HRMS calculated for C$_{14}$H$_{15}$ClN$_5$O$_2$ (M+H)$^+$: 320.0914. Found 320.0898.

(1R,2R,3S,4R,5S)-4-(2-Chloro-6-β1-(4-fluoro-3-nitrophenyl)-1H-1,2,3-triazol-4-yl)methylamino)-9H-purin-9-yl)bicyclo[3.1.0]hexane-2,3-diol (223)

4-Fluoro-3-nitro-phenylazide (9.88 mg, 0.054 mmol) and TBTA (1 mg, 0.001 mmol) were added to a solution of compound 222 (12.4 mg, 0.038 mmol) in t-butanol (0.6 mL)-water (0.6 mL) at room temperature. A freshly prepared 1M solution of sodium ascorbate (38.7 µL) followed by 7.5% solution of copper sulfate (51.6 µL, 0.015 mmol) were also added to the reaction mixture, which was then stirred at room temperature overnight. Solvent was evaporated, and the residue was purified on flash silica gel column chromatography (CH$_2$Cl$_2$:MeOH=30:1) to give compound 223 (18 mg, 96%) as a syrup. $^1$H NMR (CD$_3$OD, 300 MHz) δ 8.60-8.64 (m, 2H), 8.22-8.27 (m, 1H), 8.15 (s, 1H), 7.62-7.68 (m, 1H), 4.79 (s, 1H), 4.70 (t, J=5.1 Hz, 1H), 4.37 (s, 2H), 3.88 (d, J=6.6 Hz, 1H), 2.62 (t, J=2.4 Hz, 1H), 1.95-1.99 (m, 1H), 1.62-1.68 (m, 1H), 1.26-1.32 (m, 1H), 0.72-0.79 (m, 1H). HRMS calculated for C$_{20}$H$_{18}$ClFN$_9$O$_4$ (M+H)$^+$: 502.1154. Found 502.1150.

(1R,2R,3S,4R,5S)-4-(2-Chloro-6-(1-admantyl-1H-1,2,3-triazol-4-yl)methylamino)-9H-purin-9-yl)bicyclo[3.1.0]hexane-2,3-diol (224)

Compound 224 (92%) was prepared from compound 222 following the same method for compound 223. $^1$H NMR (CD$_3$OD, 300 MHz) δ 8.13 (s, 1H), 8.02 (s, 1H), 4.81-4.84 (m, 2H), 4.79 (s, 1H), 4.70 (t, J=6.0 Hz, 1H), 3.89 (d, J=6.0 Hz, 1H), 2.24 (s, 10H), 1.95-1.97 (m, 1H), 1.82 (s, 6H), 1.63-1.66 (m, 1H), 1.28-1.32 (m, 1H), 0.73-0.77 (m, 1H). HRMS calculated for C$_{24}$H$_{30}$ClN$_8$O$_2$ (M+H)$^+$: 497.2180. Found 497.2164.

Example 6

Figure 28A:
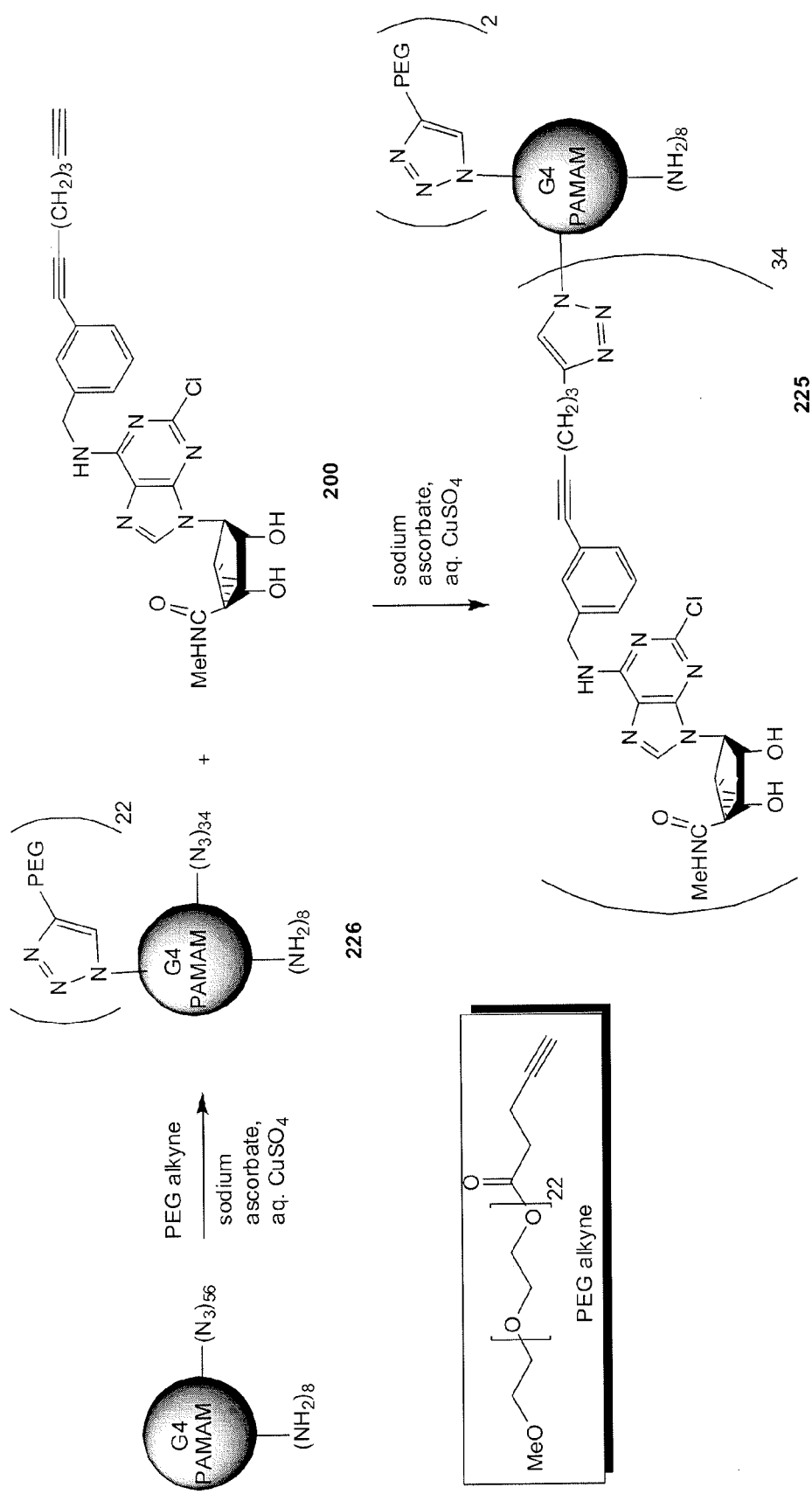
FIGS. 28A and 28B illustrate a synthetic scheme to prepare dendrimer conjugates 225 and 227 in accordance with an embodiment of the invention.
Figure 28B:
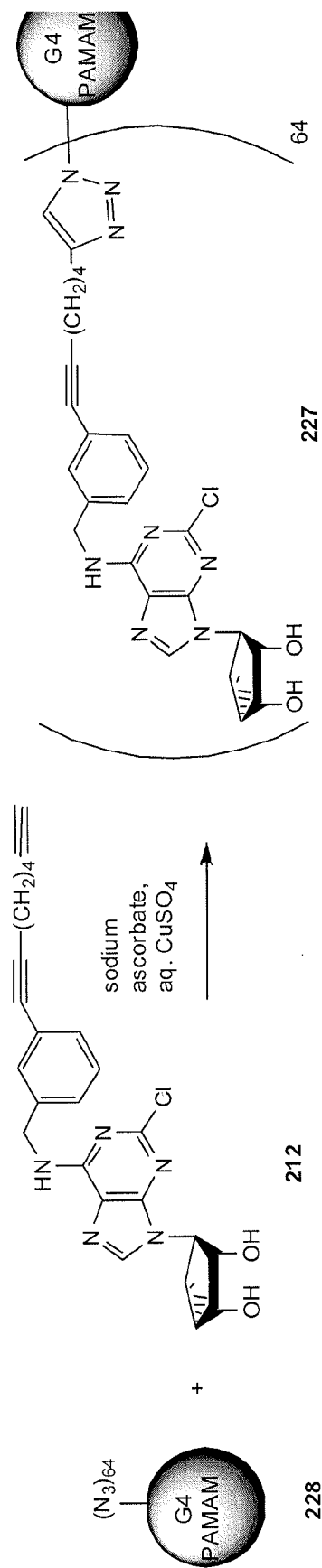
Figure 29:
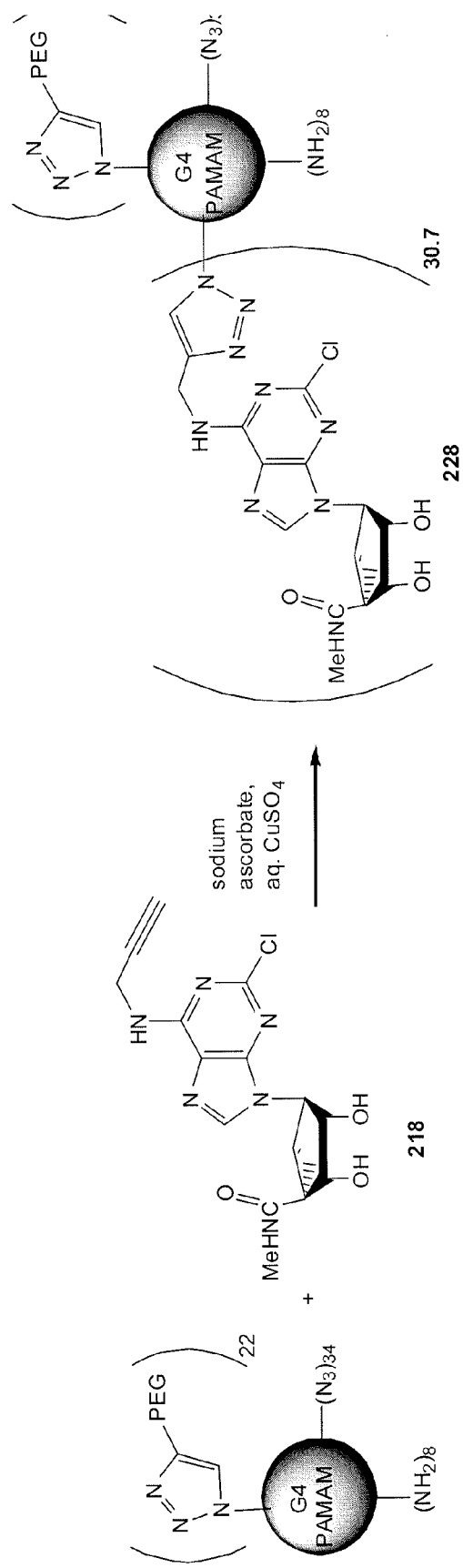
FIG. 29 illustrates a synthetic scheme to prepare a dendrimer conjugate 228 in accordance with an embodiment of the invention.

This example illustrates the synthesis of compounds in accordance with an embodiment of the invention. See FIGS. 28A, 28B, and 29 for reaction schemes illustrating the synthesis.

G4 PAMAM, Conjugated with Compound 9 and PEG (225)

Freshly prepared aqueous sodium ascorbate (1 M, 22 µL) was added to a mixture of PEG-azide dendrimer (226, 15 mg, 0.25 mop and compound 2 (5.7 mg, 10.98 mop in a mixture of DMSO (0.7 mL) and water (0.7 mL), followed by addition of 7.5% aqueous cupric sulfate (146 µL, 43.93 µmol). The reaction mixture was stirred at room temperature overnight, and the product was purified by extensive dialysis in water for 2 d. The mixture was lyophilized to give compound 225 (14 mg, 72%) as a colorless foamy solid. ESI-MS: calcd. 77501. Found 77512.

G4 PAMAM, Conjugated with Compound 212 (227)

Freshly prepared aqueous sodium ascorbate (1 M, 90 µL) was added to a mixture of azido dendrimer 228 (5.6 mg, 0.35 mop and compound 212 (10.7 mg, 22.4 mmol) in a mixture of DMSO (0.6 mL) and water (0.6 mL), followed by addition of 7.5% aqueous cupric sulfate (150 µL, 44.8 µmol). The reaction mixture was stirred at room temperature overnight, and the product was purified by extensive dialysis in water for 2 d. The mixture was lyophilized to give compound 227 (12.9 mg, 79%) as a white foamy solid. ESI-MS: calcd. 46343. Found 46024.

G4 PAMAM, Conjugated with Compound 218 and PEG (228)

Compound 228 (63%) was prepared from compound 218 following the same method for compound 225. $^1$H NMR (CD$_3$OD, 400 MHz) δ 8.13 (s, 1H).

Example 7

This example illustrates some of the properties of the compounds in accordance with an embodiment of the invention.

TABLE 1

Potency of a series of (N)-methanocarba adenosine derivatives at three subtypes of human ARs.

| Compd | n | AR Affinity Ki, nM or (% inhibition)$^a$ | | |
|---|---|---|---|---|
| | | A$_1$ | A$_{2A}$ | A$_3$ |
| 127 | — | 136 ± 22 | 784 ± 97 | 1.5 ± 0.2 |
| 200 | 3 | 104 ± 24 | 4950 ± 960 | 8.1 ± 3.1 |
| 201 | 4 | 1490 ± 230 | (19.7 ± 2.4%) | 113 ± 24 |
| 202 | 5 | (47.7 ± 6.1%) | (7.0 ± 4.3%) | 87.2 ± 49 |
| 203 | 3 | 37.4 ± 12.0 | 1960 ± 50 | 3.2 ± 1.1 |
| 204 | 4 | 2420 ± 230 | (28.6 ± 5.7%) | 71.7 ± 54 |
| 205 | 5 | 1290 ± 290 | (25.2 ± 12.6%) | 30.1 ± 13 |
| 206 | 4 | 1720 ± 240 | (17.0 ± 8.7%) | 21.8 ± 5.3 |
| 207 | 3 | | | 14.3 ± 2.3 |
| 208 | 5 | | | 47.6 ± 11.3 |
| 212 | 4 | (48.5 ± 5.1%) | (44.1 ± 5.4%) | 2500 ± 640 |
| 214 | 3 | (11.0 ± 9.4%) | (16.7 ± 10.7%) | 897 ± 20 |
| 215 | 4 | (24.3 ± 3.0%) | (8.2 ± 4.6%) | 933 ± 720 |
| 216 | 5 | (29.5 ± 8.4%) | (18.0 ± 9.7%) | 521 ± 250 |
| 218 | — | | | 1.9 |
| 219a | — | (38.0 ± 14.8%) | (19.3 ± 10.1%) | 9.1 ± 1.9 |
| 219b | — | | | 13.4 |
| 219c | — | | | ~30 |
| 220 | — | (38.4 ± 0.5%) | (4.9 ± 3.6%) | 38.1 ± 14.4 |
| 222 | — | 5870 ± 830 | (28.3 ± 2.8%) | 302 ± 26 |
| 223 | — | (44.7 ± 16%) | (19.2 ± 3.9%) | 388 ± 170 |
| 224 | — | (38.6 ± 5.0%) | (22.5 ± 7.3%) | 2190 ± 160 |
| 225 | 3 | 41.4 ± 5.3 | (47.6 ± 5.9%)$^b$ | 1.5 ± 0.2 |
| 227 | 4 | 37.9 ± 3.7 | 283 ± 130 | 7.7 ± 3.3 |
| 228 | — | 1110 ± 170 | | 13.0 ± 1.3 |

$^a$All experiments were done on CHO or HEK293 (A$_{2A}$ only) cells stably expressing one of four subtypes of human ARs. The binding affinity for A$_1$, A$_{2A}$ and A$_3$ARs was expressed as K$_i$ values (n = 3-5) and was determined by using agonist radioligands ([$^3$H]45; [$^3$H]46; or [$^{125}$I]47; respectively), unless noted. A percent in parentheses refers to inhibition of radioligand binding at 10 µM, unless noted.
$^b$Percent inhibition of radioligand binding at 1 µM.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula (I):

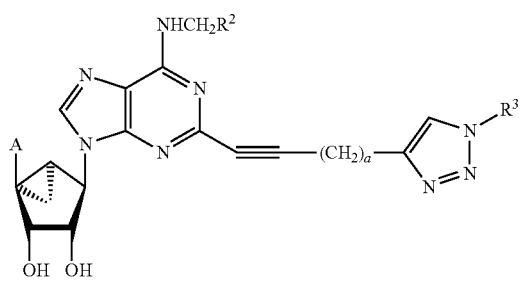

(I)

wherein A is hydrogen or —CONHR$^1$,

R$^1$ is selected from the group consisting of hydrogen, C$_1$-C$_6$ alkyl, C$_2$-C$_6$ alkenyl, C$_2$-C$_6$ alkynyl, C$_3$-C$_8$ cycloalkyl, and C$_6$-C$_{10}$ aryl, R$^2$ is a phenyl group optionally substituted with one or more halogen atoms, a is an integer of 2 to 10, R$^3$ is selected from the group consisting of phenyl optionally substituted with 1, 2, 3, 4, or 5 substituents selected from the group consisting of halogen, NO$_2$, NR$^4$R$^5$, COOH, COR$^6$, C$_1$-C$_6$ alkyl, C$_3$-C$_8$ cycloalkyl, adamantyl, C$_6$-C$_{10}$ aryl, isothiocyanato, heteroaryl, and heterocyclyl; benzyl optionally substituted with 1, 2, 3, 4, or 5 substituents selected from the group consisting of halogen, NO$_2$, NR$^4$R$^5$, COR$^6$, C$_1$-C$_6$ alkyl, C$_3$-C$_8$ cycloalkyl, adamantyl, C$_6$-C$_{10}$ aryl, heteroaryl, and heterocyclyl, R$^4$ and R$^5$ are independently hydrogen or C$_1$-C$_6$ alkyl, and R$^6$ is C$_1$-C$_6$ alkyl optionally substituted with halogen, or a pharmaceutically acceptable salt thereof.

2. The compound or salt of claim 1, wherein A is —CONHR$^1$.

3. The compound or salt of claim 2, wherein A is —CONHCH$_3$.

4. The compound or salt of claim 1, wherein R$^2$ is 3-halophenyl.

5. The compound or salt of claim 1, wherein a is 3 or 4.

6. The compound or salt of claim 1, wherein R$^3$ is phenyl substituted with 1, 2, 3, 4, or 5 substituents selected from the group consisting of halogen, NO$_2$, NR$^4$R$^5$, COOH, COR$^6$, C$_1$-C$_6$ alkyl, C$_3$-C$_8$ cycloalkyl, adamantyl, C$_6$-C$_{10}$ aryl, 4-isothiocyanato, heteroaryl, and heterocyclyl.

7. The compound or salt of claim 6, wherein R$^3$ is phenyl substituted with a substituent or substituents selected from the group consisting of 3-nitro-4-fluoro, 4-amino, 4-carboxy, 4-bromoacetyl, adamantyl, and 4-isothiocyanato.

8. The compound or salt of claim 1, wherein R$^3$ is benzyl substituted with 1, 2, 3, 4, or 5 substituents selected from the group consisting of halogen, NO$_2$, NR$^4$R$^5$, COR$^6$, C$_1$-C$_6$ alkyl, C$_3$-C$_8$ cycloalkyl, adamantyl, C$_6$-C$_{10}$ aryl, heteroaryl, and heterocyclyl.

9. The compound or salt of claim 8, wherein R$^3$ is benzyl substituted with heterocyclyl.

10. A pharmaceutical composition comprising the compound or salt of claim 1 and a pharmaceutically acceptable carrier.

11. A method of reducing intraocular pressure in a mammal comprising administering to the mammal an effective amount of a compound or salt of claim 1.

12. The compound or salt of claim 2, wherein R$^2$ is 3-halophenyl.

13. The compound or salt of claim 2, wherein a is 3 or 4.

14. The compound or salt of claim 6, wherein R$^3$ is 3-nitro-4-fluorophenyl, 4-nitro-4-fluorophenyl, 4-aminophenyl, 4-carboxyphenyl, and 4-isothiocyanatophenyl, or 4-α-bromophenacyl), R$^2$ is 3-chlorophenyl, a is 3 or 4, and A is —CONHCH$_3$.

15. A compound of the formula (I):

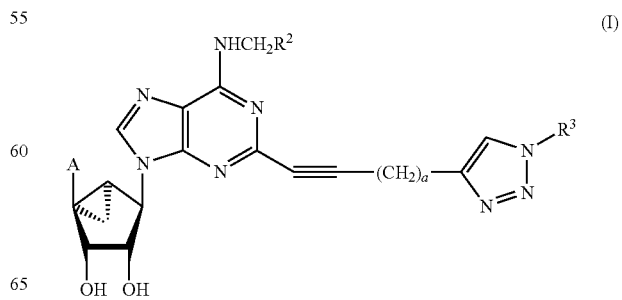

(I)

wherein $R^2$ is 3-chlorophenyl, $R^3$ is 1-adamantyl or 4-3-oxoisothiazol-2(3H)-yl)benzyl, a is 4, and A is —CONHCH$_3$, or a pharmaceutically acceptable salt thereof.

16. A pharmaceutical composition comprising a compound or salt of claim 14 and a pharmaceutically acceptable carrier.

17. A pharmaceutical composition comprising a compound or salt of claim 15 and a pharmaceutically acceptable carrier.

18. A method of reducing intraocular pressure in a mammal comprising administering to the mammal an effective amount of a compound or salt of claim 14.

19. A method of reducing intraocular pressure in a mammal comprising administering to the mammal an effective amount of a compound or salt of claim 15.

* * * * *